(12) United States Patent
Becker et al.

(10) Patent No.: US 8,692,001 B2
(45) Date of Patent: Apr. 8, 2014

(54) SULFONAMIDES FOR THE MODULATION OF PKM2

(75) Inventors: Oren M. Becker, Mevasseret Zion (IL); Alina Shitrit, Tel-Aviv (IL); Nili Schutz, Herzlia (IL); Efrat Ben-Zeev, Kiryat Motzkin (IL); Avihai Yacovan, Gedera (IL); Rachel Ozeri, Gimzo (IL); Tzofit Kehat, Hod-Hasharon (IL); Sima Mirilashvili, Lod (IL); Alex Aizikovich, Rehovot (IL); Daniel Sherman, Jerusalem (IL); Vered Behar, Moshav Bet Zayit (IL); Osnat Kashtan, Kadima (IL)

(73) Assignee: Dynamix Pharmaceuticals Ltd., Rehovot (IL)

( * ) Notice: Subject to any disclaimer, the term of this patent is extended or adjusted under 35 U.S.C. 154(b) by 0 days.

(21) Appl. No.: 13/281,929

(22) Filed: Oct. 26, 2011

(65) Prior Publication Data

US 2012/0108631 A1 May 3, 2012

Related U.S. Application Data

(60) Provisional application No. 61/455,885, filed on Oct. 27, 2010, provisional application No. 61/518,775, filed on May 10, 2011, provisional application No. 61/519,655, filed on May 25, 2011.

(51) Int. Cl.
 *C07D 405/02* (2006.01)
 *A61K 31/405* (2006.01)
(52) U.S. Cl.
 USPC .......................................... 548/454; 514/415
(58) Field of Classification Search
 USPC .......................................... 548/454; 514/415
 See application file for complete search history.

(56) References Cited

U.S. PATENT DOCUMENTS

| 2011/0046083 A1 | 2/2011 | Cantley et al. |
| 2011/0195958 A1 | 8/2011 | Thomas et al. |

FOREIGN PATENT DOCUMENTS

| EP | 0673937 A1 | 9/1995 |
| GB | 2041371 A | 9/1980 |
| JP | 11222435 A | 8/1999 |
| WO | WO-9910320 A1 | 3/1999 |
| WO | WO-0138584 A2 | 5/2001 |
| WO | WO-2004106339 A2 | 12/2004 |
| WO | WO-2004106340 A2 | 12/2004 |
| WO | WO-2008072794 A1 | 6/2008 |
| WO | WO-2009034547 A2 | 3/2009 |
| WO | WO-2009149192 A1 | 12/2009 |
| WO | WO-2010042867 A2 | 4/2010 |
| WO | WO-2010118063 A2 | 10/2010 |
| WO | WO-2010129596 A1 | 11/2010 |
| WO | WO-2011002816 A1 | 1/2011 |
| WO | WO-2011002817 A1 | 1/2011 |

OTHER PUBLICATIONS

STN results, Goldfarb, US Patent Application Publication 20090163545 (2009).*

* cited by examiner

*Primary Examiner* — Yong Chu
*Assistant Examiner* — Sonya Wright
(74) *Attorney, Agent, or Firm* — Mintz Levin Cohn Ferris Glovsky and Popeo, P.C.

(57) ABSTRACT

The invention relates to sulfonamide compounds and methods for activating PKM2. The compounds and methods are useful in treating or preventing a disease or disorder selected from cancer, cell proliferative disorder, inflammatory disorder, metabolic disorder, and immune system disorder.

20 Claims, 3 Drawing Sheets

SULFONAMIDES FOR THE MODULATION OF PKM2

RELATED APPLICATIONS

This application claims priority under 35 U.S.C. 119(e) to U.S Provisional Application Nos. 61/455,885, filed Oct. 27, 2010; 61/518,775, filed May 10, 2011; and 61/519,655, filed May 25, 2011. The entire teachings of the above applications are incorporated herein by reference.

BACKGROUND OF THE INVENTION

Tumor development is associated with major metabolic changes. In the 1920s, Otto Warburg observed that cancer cells have high glucose consumption and lactate production even in the presence of oxygen (a process termed aerobic glycolysis). Recent research has demonstrated that these metabolic differences drive tumor growth. By modulating their metabolic processes, cancer cells are able to divert sugars, fats and other energy sources away from energy production to satisfy the ever growing demands of uncontrolled proliferation.

Pyruvate Kinase (PK) is a metabolic enzyme that catalyzes the transfer of a phosphate group from phosphoenol pyruvate to ADP, to produce pyruvate and ATP during glycolysis. There are four PK isozymes—the L and the R isozymes are expressed in liver and red blood cells, respectively; the M1 isozyme is expressed in most adult cells, and the M2 isoenzyme—an M2 splice variant (PKM2)—is exclusively expressed during embryonic development and in cancer cells.

While PKM1 is a constitutively active enzyme, PKM2 undergoes a transformation from an energy efficient tetrametic form to an 'energy inefficient' dither form. The main effector that balances the dimer-tetramer ratio of PKM2 in tissues is fructose 1,6-bisphosphate (FBP), a glycolysis intermediate product upstream of PKM2.

PKM2 is a key mediator of the Warburg effect in cancer cells leading to lower energy production and an abundance of building blocks for tumor replication and growth. There is thus a need in the art for, inter alia, modulators of the metabolism of proliferating cells.

SUMMARY OF THE INVENTION

Compounds according to embodiments of the present invention modulate the metabolism of proliferating cells (e.g., cancer cells or lymphocytes, such as B or T cells). For example, in some embodiments, compounds of the invention are useful in the modulation (e.g., activation) of PKM2. Compounds of the present invention are useful as pharmaceutical agents. The compounds may be used without limitation, for example, as anti-cancer, anti-proliferative, anti-inflammatory and/or immunosuppressive agents, for treating mammals, such as for treating humans. Compounds of the present invention may be useful for modulating the metabolism of proliferating cells in a disease or disorder. Such diseases and disorders include, without limitation, cancers, cell proliferative disorders, inflammatory disorders, metabolic disorders, and immune system disorders. Compounds of the invention may be useful for regulating (e.g., activating) a PKM2 involved in a disease or disorder, such as a cancer.

Compounds of the invention include compound of Formula IA:

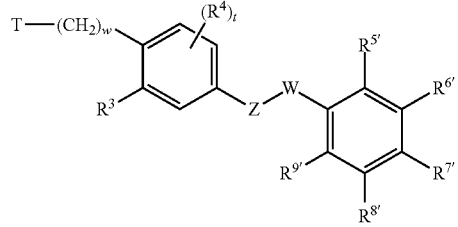

Formula IA or a salt, solvate, hydrate, or prodrug thereof, wherein:

Z is selected from the group consisting of CO, $SO_2$, O, S, and $NR^a$; and
  (i) when Z is CO or $SO_2$,
    W is either absent or is selected from the group consisting of $O(CH_2)_k$, $NR^b(CH_2)_k$, $(CH_2)_k$, $(CH_2)_kO$, $(CH_2)_kS$ and $(CH_2)_kNR^b$, wherein k is 0, 1, 2 or 3, or
  (ii) when Z is O, S, or $NR^a$,
    W is selected from the group consisting of $(CH_2)_kCO$ and $(CH_2)_kSO_2$, wherein k is 0, 1, 2, or 3,
    wherein $R^a$ and $R^b$ are, each independently selected from the group consisting of hydrogen, linear or branched $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ cycloalkenyl, and heterocycloalkyl;

T is selected from the group consisting of $NR^2COR^1$ and $NR^2S(O)_2R^1$;

$R^1$ is selected from the group consisting of a linear or branched $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ cycloalkenyl, heterocycloalkyl, aryl and heteroaryl,
  wherein said alkyl, alkenyl, alkynyl, cycloalkyl, cycloalkenyl, heterocycloalkyl, aryl and heteroaryl are unsubstituted or substituted with one or more $R^c$, $R^c$ is independently at each occurrence selected from the group consisting of linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, aryloxy, linear or branched $C_1$-$C_6$ haloalkoxy, linear or branched $C_1$-$C_6$ alkylsulfonyl, linear or branched $C_1$-$C_6$ thioalkyl, thioaryl, $C_3$-$C_8$ cycloalkyl, $C_3$-$C_8$ cycloalkenyl, aryl, heteroaryl, heterocycloalkyl, hydroxyl, cyano, nitro, halogen, $COR^d$, $COOR^d$, $CONR^dR^e$, $NHCOR^d$, and $NR^dR^e$;

$R^d$ and $R^e$ are, each independently selected from the group consisting of linear or branched, $C_1$-$C_6$ alkyl, linear or branched $C_2$-$C_6$ alkenyl, $C_2$-$C_6$ alkynyl, $C_3$-$C_8$ cycloalkyl, $C_3$-$C_8$ cycloalkenyl, heterocycloalkyl, aryl, and heteroaryl;

$R^2$ and $R^3$ are either
  (i) each independently selected from the group consisting of hydrogen, halogen, nitro, linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, $C_3$-$C_8$ cycloalkyl, $C_3$-$C_8$ cycloalkenyl, and heterocycloalkyl; or
  (ii) $R^2$ and $R^3$, together with the atoms to which they are attached, form a five to seven membered heterocycloalkyl or heteroaryl, wherein said ring is unsubstituted or substituted with one or more $R^m$, $R^m$ is selected from the group consisting of halogen, linear or branched $C_1$-$C_6$ alkyl, linear or branched $C_2$-$C_6$ alkenyl, linear or branched $C_2$-$C_6$ alkynyl, linear or branched $C_1$-$C_6$ alkoxy, linear or branched $C_1$-$C_6$ haloalkyl, benzyloxy, $NR^dR^e$, $NHCOR^d$, and $SO_2R^d$;

$R^4$ is selected from the group consisting of halogen, linear or branched $C_1$-$C_6$ alkyl, linear or branched $C_2$-$C_6$ alkenyl, linear or branched $C_2$-$C_6$ alkynyl, and heteroalkyl, wherein said alkyl, alkenyl, alkynyl, and heteroalkyl are unsubstituted or substituted with one or more $R^f$, $R^f$ is independently at each occurrence selected from the group consisting of linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, aryloxy, linear or branched $C_1$-$C_6$ haloalkoxy, linear or branched $C_1$-$C_6$ alkylsulfonyl, linear or branched, $C_1$-$C_6$ thioalkyl, thioaryl, $C_3$-$C_8$ cycloalkyl, $C_3$-$C_8$ alkenyl, aryl, heteroaryl, heterocycloalkyl, hydroxyl, cyano, amino, nitro, halogen, $COR^g$, $COOR^g$, $CONR^gR^h$, $NHCOR^g$, and $NR^gR^h$;

$R^g$ and $R^h$ are, each independently selected from a group consisting of hydrogen, linear or branched $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ cycloalkenyl, heterocycloalkyl, aryl and heteroaryl;

t is 0, 1, 2 or 3;

$R^{5'}$, $R^{6'}$, $R^{7'}$, $R^{8'}$ and $R^{9'}$ are, each independently, selected from hydrogen, linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, benzyloxy, aryloxy, linear or branched $C_1$-$C_6$ haloalkoxy, linear or branched $C_1$-$C_6$ alkylsulfonyl, linear or branched $C_1$-$C_6$ thioalkyl or thioaryl, $C_3$-$C_8$ cycloalkyl, $C_3$-$C_8$ cycloalkenyl, aryl, heteroaryl, heterocycloalkyl, hydroxyl, cyano, amino, nitro, halogen, $COR^i$, $COOR^i$, $CONR^iR^j$, $NHCOR^i$, and $NR^iR^j$;

$R^i$ and $R^j$ are, each independently, hydrogen or a group selected from a linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, $C_3$-$C_8$ cycloalkyl, $C_3$-$C_8$ cycloalkenyl, or heterocycloalkyl, aryl and heteroaryl, wherein said alkyl, alkenyl, alkynyl, cycloalkyl, cycloalkenyl, heterocycloalkyl, aryl, and heteroaryl are unsubstituted or substituted with one or more $R^k$, $R^k$ is selected from halogen or hydroxyl, or two of $R^{5'}$, $R^{6'}$, $R^{7'}$, $R^{8'}$ and $R^{9'}$, together with the atoms to which they are attached, form a $C_5$-$C_7$ cycloalkyl, heterocycloalkyl, aryl or heteroaryl, wherein said heterocycloalkyl ring is unsubstituted or substituted with one or more $R^{m1}$ selected from $C_1$-$C_6$alkyl and $S(O)_p(C_1$-$C_6$ alkyl);

w is 0 or 1, p is 0, 1, or 2;

with the proviso that when Z is CO and $R^2$ and $R^3$, together with the atoms to which they are attached, do not form a five to seven membered ring then W is not $NR^b(CH_2)_k$.

In one aspect, compounds of the invention include a compound of Formula IA, wherein Z is selected from $SO_2$ or $NR^a$ and (i) when Z is $SO_2$, W is either absent or $NR^b$ and (ii) when Z is $NR^a$, W is $SO_2$.

Compounds of the invention include a compound of Formula IIA:

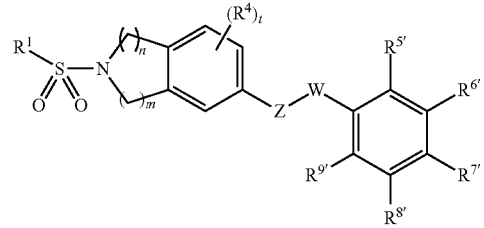

(IIA)

or a salt, solvate, hydrate or prodrug thereof, wherein:

Z is $SO_2$ and W is absent;

m is 0, 1, 2, 3, or 4;

n is 0, 1, 2, 3 or 4, thereby forming a five to seven membered heteroaryl or a five to seven membered heterocycloalkyl ring, wherein the five to seven membered heteroaryl or heterocycloalkyl ring is unsubstituted or substituted with one or more $R^m$, $R^m$ is selected from the group consisting of linear or branched $C_1$-$C_6$ alkyl, linear or branched $C_2$-$C_6$ alkenyl, and linear or branched $C_2$-$C_6$ alkynyl;

$R^1$ is selected from the group consisting of a linear or branched $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ cycloalkenyl, heterocycloalkyl, aryl and heteroaryl, wherein said alkyl, alkenyl, alkynyl, cycloalkyl, cycloalkenyl, heterocycloalkyl, aryl and heteroaryl are unsubstituted or substituted with one or more Rc, $R^c$ is independently at each occurrence selected from the group consisting of linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, aryloxy, linear or branched $C_1$-$C_6$ haloalkoxy, linear or branched $C_1$-$C_6$ alkylsulfonyl, linear or branched $C_1$-$C_6$ thioalkyl, thioaryl, $C_3$-$C_8$ cycloalkyl, $C_3$-$C_8$ cycloalkenyl, aryl, heteroaryl, heterocycloalkyl, hydroxyl, cyano, nitro, halogen, $COR^d$, $COOR^d$, $CONR^dR^e$, $NHCOR^d$, and $NR^dR^e$;

$R^d$ and $R^e$ are, each independently selected from the group consisting of linear or branched, $C_1$-$C_6$ alkyl, linear or branched $C_2$-$C_6$ alkenyl, $C_2$-$C_6$ alkynyl, $C_3$-$C_8$ cycloalkyl, $C_3$-$C_8$ cycloalkenyl, heterocycloalkyl, aryl, and heteroaryl;

$R^4$ is selected from the group consisting of halogen, linear or branched $C_1$-$C_6$ alkyl, linear or branched $C_2$-$C_6$ alkenyl, linear or branched $C_2$-$C_6$ alkynyl, and heteroalkyl, wherein said alkyl, alkenyl, alkynyl, and heteroalkyl are unsubstituted or substituted with one or more $R^f$, $R^f$ is independently at each occurrence selected from the group consisting of linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, aryloxy, linear or branched $C_1$-$C_6$ haloalkoxy, linear or branched $C_1$-$C_6$ alkylsulfonyl, linear or branched, $C_1$-$C_6$ thioalkyl, thioaryl, $C_3$-$C_8$ cycloalkyl, $C_3$-$C_8$ alkenyl, aryl, heteroaryl, heterocycloalkyl, hydroxyl, cyano, amino, nitro, halogen, $COR^g$, $COOR^g$, $CONR^gR^h$, $NHCOR^g$, and $NR^gR^h$;

$R^g$ and $R^h$ are, each independently selected from a group consisting of hydrogen, linear or branched $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ cycloalkenyl, heterocycloalkyl, aryl and heteroaryl;

t is 0, 1, 2 or 3;

$R^{5'}, R^{6'}, R^{7'}, R^{8'}$ and $R^{9'}$ are, each independently, selected from hydrogen, linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, benzyloxy, aryloxy, linear or branched $C_1$-$C_6$ haloalkoxy, linear or branched $C_1$-$C_6$ alkylsulfonyl, linear or branched $C_1$-$C_6$ thioalkyl or thioaryl, $C_3$-$C_8$ cycloalkyl, $C_3$-$C_8$ cycloalkenyl, aryl, heteroaryl, heterocycloalkyl, hydroxyl, cyano, amino, nitro, halogen, $COR^i$, $COOR^i$, $CONR^iR^j$, $NHCOR^i$, and $NR^iR^j$;

$R^i$ and Rj are, each independently, hydrogen or a group selected from a linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, $C_3$-$C_8$ cycloalkyl, $C_3$-$C_8$ cycloalkenyl, or heterocycloalkyl, aryl and heteroaryl, wherein said alkyl, alkenyl, alkynyl, cycloalkyl, cycloalkenyl, heterocycloalkyl, aryl, and heteroaryl are unsubstituted or substituted with one or more $R^k$, $R^k$ is selected from halogen or hydroxyl, or two of $R^{5'}, R^{6'}, R^{7'}, R^{8'}$ and $R^{9'}$, together with the atoms to which they are attached, form a $C_5$-$C_7$ cycloalkyl, heterocycloalkyl, aryl or heteroaryl, wherein said heterocycloalkyl ring is unsubstituted or substituted with one or more $R^{m1}$ selected from $C_1$-$C_6$ alkyl and $S(O)_p(C_1$-$C_6$ alkyl);

w is 0 or 1; and p is 0, 1, or 2.

Compounds of the invention include compounds of Formula IIB:

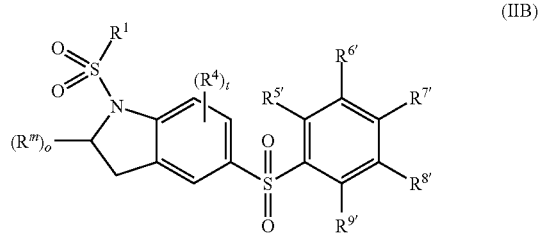

(IIB)

or a salt, solvate, hydrate, or prodrug thereof, wherein $R^m$ is 0 or 1.

Compounds of the invention include compounds of Formula IID:

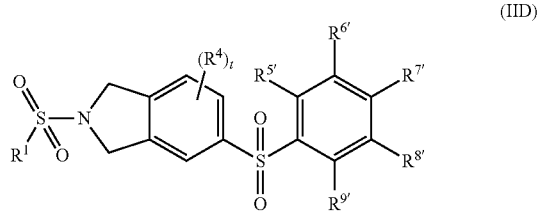

(IID)

or a salt, solvate, hydrate, or prodrug thereof.

In one aspect, embodiments of the invention are drawn to a compound according to any one of formulae described herein, wherein (i) $R^{6'}$ and $R^{7'}$ or $R^{7'}$ and $R^{8'}$ together with the atoms to which they are attached form a $C_5$-$C_7$ heterocycloalkyl ring, wherein said heterocycloalkyl ring is unsubstituted or substituted with $C_1$-$C_6$ alkyl or $S(O)_p(C_1$-$C_6$ alkyl) and the remaining $R_{6'}$ or $R_{8'}$ is selected from hydrogen, linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, benzyloxy, aryloxy, linear or branched $C_1$-$C_6$ haloalkoxy, linear or branched $C_1$-$C_6$ alkylsulfonyl, linear or branched $C_1$-$C_6$ thioalkyl, thioaryl, $C_3$-$C_8$ cycloalkyl, $C_3$-$C_8$ cycloalkenyl, aryl, heteroaryl, heterocycloalkyl, hydroxyl, cyano, amino, nitro, halogen, $COR^i$, $COOR^i$, $CONR^iR^j$, $NHCOR^i$, and $NR^iR^j$ or (ii) at least one of $R^{6'}, R^{7'}$, or $R^{8'}$ is $C_1$-$C_6$ alkoxy.

In one aspect, embodiments of the invention are drawn to a compound according to any one of formulae described herein, wherein $R^{6'}$ and $R^{7'}$ or $R^{7'}$ and $R^{8'}$ together with the atoms to which they are attached form a 1,4-dioxane ring. In one aspect, embodiments of the invention are drawn to a compound of the invention, wherein remaining $R^{6'}$ or $R^{8'}$ and $R^{5'}$ and $R^{9'}$ are each hydrogen.

In one aspect, embodiments of the invention are drawn to a compound according to any one of formulae described herein, wherein $R^1$ is selected from $C_1$-$C_6$ alkyl, $C_2$-$C_6$ alkenyl, $C_2$-$C_6$ alkynyl, $C_1$-$C_6$ haloalkyl, aryl, heteroaryl, $C_3$-$C_8$ cycloalkyl, and $C_3$-$C_8$ cycloalkenyl. In one aspect, embodiments of the invention are drawn to a compound of the invention, wherein $R^1$ is selected from $C_1$-$C_6$ alkyl and aryl, wherein said aryl is unsubstituted or substituted with one or more $R^c$.

In one aspect, embodiments of the invention are drawn to a compound according to any one of formulae described herein, wherein t is 0.

Embodiments of the invention include a compound according to any one of formulae described herein, wherein the compound is a compound of Table 1 or Table 2.

Embodiments of the invention include a pharmaceutical composition comprising a compound according to any one of formulae or compounds described herein and at least one pharmaceutically acceptable carrier or excipient.

Embodiments of the invention include a solvate of a compound according to any one of formulae or compounds described herein.

Embodiments of the invention also include a hydrate of a compound according to any one of the formulae or compounds described herein.

Embodiments of the invention also include a salt of a compound according to any one of the formulae or compounds described herein.

Embodiments of the invention also include an acid addition salt of a compound according to any one of the formulae or compounds described herein e.g., hydrochloride salt.

Embodiments of the invention also include a prodrug of a compound according to any one of the formulae or compounds described herein.

Embodiments of the invention also include a pharmaceutically acceptable salt of a compound according to any one of the formulae or compounds described herein.

Embodiments of the invention include any of the compounds listed in Tables 1 and 2 or a salt, solvate, hydrate, or prodrug thereof. In some embodiments, the compound in Tables 1 or 2 is one that activates PKM2 by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more.

Embodiments of the invention include pharmaceutical compositions comprising one of the foregoing compounds and at least one pharmaceutically acceptable carrier or excipient. The foregoing pharmaceutical compositions, where applicable, may be prepared with pure or essentially pure enantiomeric compounds according to embodiments of the invention, having an enantiopurity of at least 90% enantiomeric excess (EE), preferably at least 95% EE, more preferably at least 98% EE, and most preferably at least 99% EE. Alternatively, the foregoing pharmaceutical compositions, where applicable, may be prepared as mixture of enantiomeric forms of the compounds (e.g., as a racemic mixture or as a mixture of enantiomers with a ratio of 60:40, 70:30, 80:20 or 90:10 between two enantiomeric forms).

Embodiments of the invention include the foregoing compounds that activate PKM2 by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more.

In one aspect, a compound according to any of the formulae or compounds disclosed herein may be used as a pharmaceutical agent. For example, the foregoing compounds are used as anti-cancer, anti-proliferative, anti-inflammatory, and/or immunosuppressive agents for treating humans and/or animals, such as for treating humans and/or other mammals, preferably humans.

Embodiments of the invention include a compound according to any one of the formulae or compounds disclosed herein in the manufacture of a medicament to treat or prevent a disease or disorder that is modulated by PKM2 activation. For example, a compound according to embodiments of the invention may be used in the manufacture of a medicament to be used as an anti-cancer, anti-proliferative, anti-inflammatory, and/or immunosuppressive agent.

Embodiments of the invention include a compound according to any one of formulae or compounds described herein or a pharmaceutical composition comprising a compound according to any one of formulae or compounds described herein in the manufacture of a medicament for preventing or treating a disease or disorder selected from cancer, cell proliferative disorder, inflammatory disorder, metabolic disorder, and immune system disorder.

Embodiments of the invention include methods of treating or preventing cancers and/or cell proliferation disorders in a subject by administering a pharmaceutical composition that includes an effective amount of one of the compounds of any of the formulae or compounds described herein. For example, the cancer or cell proliferation disorder is cancer, pre-cancer or a hyperproliferative disorder. In some embodiments, the foregoing methods are monotherapies for preventing or treating cancer and/or cell proliferation disorder. In some embodiments, the cancer and/or cell proliferation disorder is a cell proliferative disorder of the hematologic system (e.g., leukemia or lymphoma). In some embodiments, the cancer and/or a cell proliferation disorder is of the lung, colon, pancreas, prostate, skin, ovary, or breast. In some embodiments, the pharmaceutical composition is administered as a chronic therapy or a maintenance therapy.

In some embodiments, the pharmaceutical composition is administered as part of a combination therapy comprising an additional therapy. In some embodiments, the foregoing methods are part of a combination therapy with other therapeutic agents (e.g., a cancer metabolism modulators, targeted agent or a cytotoxic agent) and/or non-drug therapies (e.g., surgery, immunotherapy or radiation treatment). In some embodiments of the combination therapy, the additional therapy is conducted substantially simultaneously or concurrently with the pharmaceutical composition's administration. In some embodiments, the administration of the pharmaceutical composition is conducted prior to the additional therapy of the combination therapy. In some embodiments, the administration of the pharmaceutical composition is conducted subsequent to the additional therapy. In some embodiments, the pharmaceutical composition is administered chronically (e.g., as part of a maintenance therapy). In some embodiments, the cancer and/or cell proliferation disorder is a cell proliferative disorder of the hematologic system (e.g., leukemia or lymphoma). In some embodiments, the cancer and/or cell proliferation disorder is a cell proliferative disorder of the lung (e.g., lung cancer). In some embodiments, the cancer and/or cell proliferation disorder is a cell proliferative disorder of the colon (e.g., colon cancer). In some embodiments, the cancer and/or cell proliferation disorder is a cell proliferative disorder of the pancreas (e.g., pancreatic cancer). In some embodiments, the cancer and/or cell proliferation disorder is a cell proliferative disorder of the prostate (e.g., prostate cancer). In some embodiments, the cancer and/or cell proliferation disorder is a cell proliferative disorder of the skin (e.g., skin cancer). In some embodiments, the cancer and/or cell proliferation disorder is a cell proliferative disorder of the ovary (e.g., ovarian cancer). In some embodiments, the cancer and/or cell proliferation disorder is a cell proliferative disorder of the breast (e.g., breast cancer).

In some embodiments, the invention includes a method of regulating immune system activity in a subject comprising administering a pharmaceutical composition that includes an effective amount of one of the compounds of any of the formulae or compounds described herein. For example, modulating immune system activity includes modulating autoimmune diseases such as transplant rejection (e.g., kidney, heart, lung, liver, pancreas, skin, host versus graft reaction (HVGR), etc.), rheumatoid arthritis, and amyotrophic lateral sclerosis. Another aspect of the invention includes use of a compound of the invention in the manufacture of a medicament to regulate immune system activity. In some embodiments, the compound is administered before the onset of immune system irregularity. In other embodiments, the compound is administered after the onset of immune system irregularity.

In some embodiments, the invention includes a method of preventing or treating an inflammatory disease in a subject comprising administering a pharmaceutical composition that includes an effective amount of one of the compounds of any of the formulae or compounds described herein.

In some embodiments, the administration of the compound is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In some embodiments, the compound is administered with a pharmaceutically acceptable carrier.

In one aspect, embodiments of the invention are drawn to methods of activating PKM2 by contacting PKM2 with a compound according to embodiments of the present invention or a salt, solvate, hydrate, or prodrug thereof. In some embodiments, PKM2 is activated by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more. In some embodiments, the PKM2 activated is in a cell, e.g., a human cell.

It is contemplated that whenever appropriate, any embodiment of the invention can be combined with one or more other embodiments of the invention, even though the embodiments are described under different aspects of the invention.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the examples and figures.

DETAILED DESCRIPTION OF THE INVENTION

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present specification will control.

Compounds of the invention modulate the metabolism of proliferating cells (e.g., cancer cells or lymphocytes, such as B or T cells). Compounds of the invention may be useful as pharmaceutical agents for modulating the metabolism of proliferating cells in a disease or disorder. Such diseases and disorders include, without limitation, cancers, cell proliferative disorders, inflammatory disorders, metabolic disorders, and immune system disorders. For example, the compounds may be useful as anti-cancer, anti-proliferative, anti-inflammatory and/or immunosuppressive agents, for treating mammals, such as for treating humans.

Figure 1:
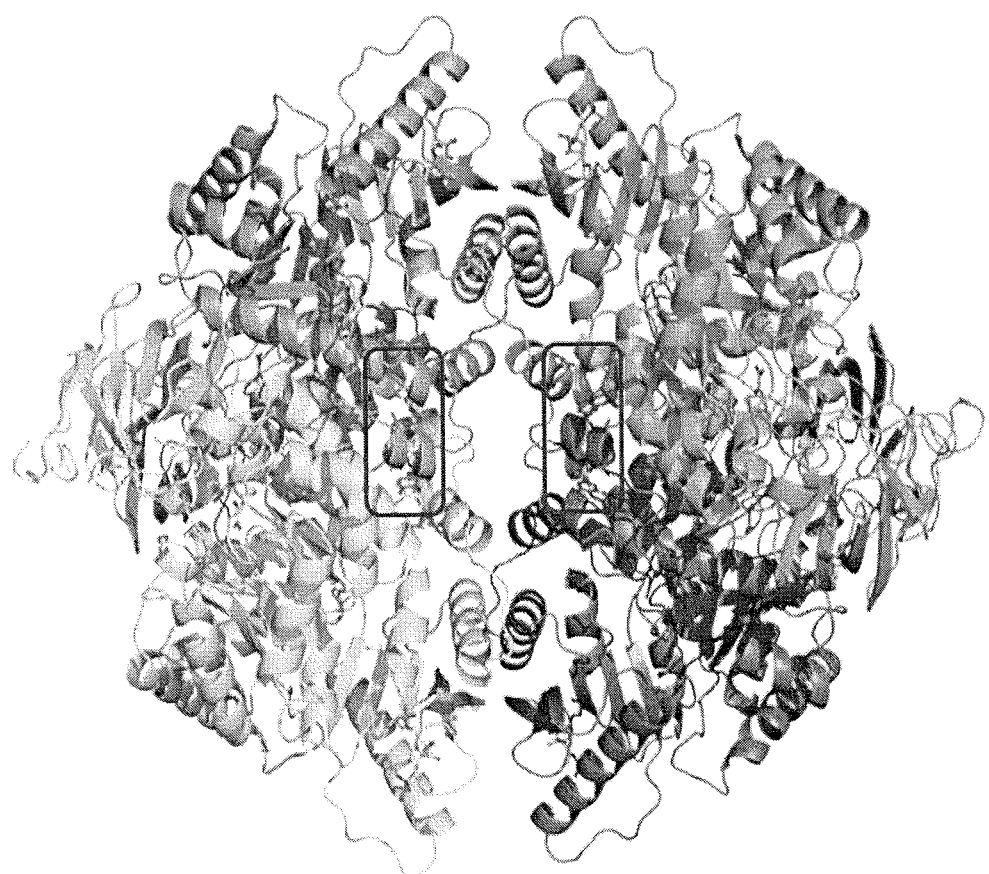
FIG. 1 shows the crystal structure of a complex of PKM2 in the active tetrameric state with the compound 5-((2,3-dihydrobenzo[b][1,4] dioxin-6-yl)sulfonyl)-2-methyl-1-(methylsulfonyl)indoline. The compound is shown in boxes.

Without wishing to be bound by theory, PKM2 is a key mediator of the Warburg effect in cancer cells, leading to lower energy production and an abundance of building blocks for tumor replication and growth. Thus, it is believed that activating PKM2 may be an important way to treat or prevent cancers and proliferative diseases. Compounds of the invention are useful in the activation of PKM2. For example, and without wishing to be bound by theory, compounds according to certain embodiments of the invention stabilize the active tetrameric form of PKM2, as shown in FIG. 1. The compounds of the invention are useful as pharmaceutical agents, for example, as therapeutic agents for treating humans and animals. The compounds may be used without limitation, for example, as anti-cancer or other cell proliferation-related disorders.

In one aspect, compounds of the invention include compounds of Formula I or a salt, solvate, hydrate, or prodrug thereof:

Formula I

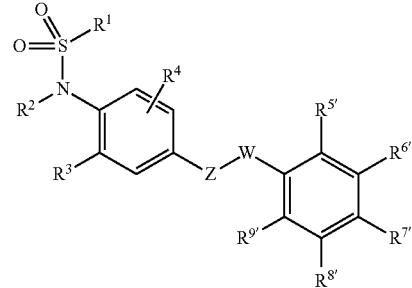

wherein:
Z is selected from CO, $SO_2$, O, S, or $NR^a$; and
(i) when Z is CO or $SO_2$,
W is either absent or is selected from the group consisting of $O(CH_2)_k$, $NR^b(CH_2)_k$, $(CH_2)_k$, $(CH_2)_kO$, $(CH_2)_kS$ and $(CH_2)_kNR^b$, wherein k is between 1 and 3, or
(ii) when Z is O, S, or $NR^a$,
W is selected from the group consisting of $(CH_2)_kCO$ and $(CH_2)_kSO_2$, wherein k is between 1 and 3,
$R^a$ and $R^b$ are, each independently, hydrogen or a group selected from a linear or branched, saturated or unsaturated $C_1$-$C_6$ alkyl, a saturated or unsaturated $C_3$-$C_6$ cycloalkyl or heterocycloalkyl;
$R^1$ is selected from the group consisting of a linear or branched, saturated or unsaturated $C_1$-$C_6$ alkyl, a saturated or unsaturated $C_3$-$C_8$ cycloalkyl or heterocycloalkyl, an aryl and heteroaryl,
wherein said alkyl, cycloalkyl, heterocycloalkyl, aryl or heteroaryl is unsubstituted or substituted with one or more $R^c$,
$R^c$ is independently at each occurrence selected from the group consisting of linear or branched, saturated or unsaturated $C_1$-$C_6$ alkyl; linear or branched, saturated or unsaturated $C_1$-$C_6$ haloalkyl; linear or branched, saturated or unsaturated $C_1$-$C_6$ alkoxy or aryloxy; linear or branched, saturated or unsaturated $C_1$-$C_6$ haloalkoxy; linear or branched, saturated or unsaturated $C_1$-$C_6$ alkylsulfonyl; linear or branched, saturated or unsaturated $C_1$-$C_6$ thioalkyl or thioaryl; saturated or unsaturated $C_3$-$C_8$ cycloalkyl; aryl; heteroaryl; heterocycloalkyl; hydroxyl; cyano; amino; nitro; halogen; $COR^d$; $COOR^d$; $CONR^dR^e$; $NHCOR^d$, and $NR^dR^e$;
$R^d$ and $R^e$ are, each independently, hydrogen or a group selected from a linear or branched, saturated or unsaturated $C_1$-$C_6$ alkyl, a saturated or unsaturated $C_3$-$C_8$ cycloalkyl or heterocycloalkyl, an aryl and a heteroaryl;
$R^2$ and $R^3$ are either (i) each independently selected from the group consisting of a hydrogen, a linear or branched, saturated or unsaturated $C_1$-$C_6$ alkyl, and a saturated or unsaturated $C_3$-$C_6$ cycloalkyl or heterocycloalkyl; or (ii) $R^2$ and $R^3$, together with the atoms to which they are attached, form a five to seven membered heterocycloalkyl or heteroaryl, wherein said ring is unsubstituted or substituted with one or more linear or branched, saturated or unsaturated $C_1$-$C_6$ alkyl;

R⁴ is selected from hydrogen, or a linear or branched, saturated or unsaturated $C_1$-$C_6$ alkyl or heteroalkyl,
wherein said alkyl or heteroalkyl is unsubstituted or substituted with one or more $R^f$,
$R^f$ is independently at each occurrence selected from the group consisting of: linear or branched, saturated or unsaturated $C_1$-$C_6$ alkyl; a linear or branched, saturated or unsaturated $C_1$-$C_6$ haloalkyl; linear or branched, saturated or unsaturated $C_1$-$C_6$ alkoxy or aryloxy; linear or branched, saturated or unsaturated $C_1$-$C_6$ haloalkoxy; a linear or branched, saturated or unsaturated $C_1$-$C_6$ alkylsulfonyl; linear or branched, saturated or unsaturated $C_1$-$C_6$ thioalkyl or thioaryl; saturated or unsaturated $C_3$-$C_8$ cycloalkyl; aryl; heteroaryl; heterocycloalkyl; hydroxyl; cyano; amino; nitro; halogen; $COR^g$; $COOR^g$; $CONR^gR^h$; $NHCOR^g$, and $NR^gR^h$;
$R^g$ and $R^h$ are, each independently, hydrogen or a group selected from a linear or branched, saturated or unsaturated $C_1$-$C_6$ alkyl, a saturated or unsaturated $C_3$-$C_8$ cycloalkyl or heterocycloalkyl, an aryl and a heteroaryl;
$R^{5'}$, $R^{6'}$, $R^{7'}$, $R^{8'}$ and $R^{9'}$ are, each independently, selected from hydrogen; linear or branched, saturated or unsaturated $C_1$-$C_6$ alkyl; linear or branched, saturated or unsaturated $C_1$-$C_6$ haloalkyl; linear or branched, saturated or unsaturated $C_1$-$C_6$ alkoxy or aryloxy; linear or branched, saturated or unsaturated $C_1$-$C_6$ haloalkoxy; linear or branched, saturated or unsaturated $C_1$-$C_6$ alkylsulfonyl; linear or branched, saturated or unsaturated $C_1$-$C_6$ thioalkyl or thioaryl; saturated or unsaturated $C_3$-$C_8$ cycloalkyl; aryl; heteroaryl; heterocycloalkyl; hydroxyl; cyano; amino; nitro; halogen; $COR^i$; $COOR^i$; $CONR^iR^j$; $NHCOR^i$, and $NR^iR^j$;
$R^i$ and $R^j$ are, each independently, hydrogen or a group selected from a linear or branched, saturated or unsaturated $C_1$-$C_6$ alkyl, a saturated or unsaturated $C_3$-$C_8$ cycloalkyl or heterocycloalkyl, an aryl and a heteroaryl; or
two of $R^{5'}$, $R^{6'}$, $R^{7'}$, $R^{8'}$ and $R^{9'}$, together with the atoms to which they are attached, form a $C_5$-$C_7$ cycloalkyl, heterocycloalkyl, aryl, or heteroaryl;
with the proviso that when Z is CO and $R^2$ and $R^3$, together with the atoms to which they are attached, do not form a five to seven membered ring then W is not $NR^b(CH_2)_k$.

Compounds of the invention include compounds described herein that activate PKM2 by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more.

In some embodiments, $R^1$ is a $C_1$-$C_6$ alkyl, such as a $C_1$-$C_3$ alkyl (e.g., a methyl or an ethyl). In some embodiments, $R^1$ is an unsubstituted or substituted phenyl.

In some embodiments, Z is CO and W is absent. In some embodiments, Z is $SO_2$ and W is absent. In some embodiments, Z is CO and W is $(CH_2)S$. In some embodiments, Z is CO and W is $(CH_2)O$. In some embodiments, Z is CO and W is $O(CH_2)$. In some embodiments, Z is O and W is $(CH_2)CO$.

In some embodiments, $R^4$ is not hydrogen. In some embodiments, $R^4$ is hydrogen.

In some embodiments, $R^2$ and $R^3$ are both hydrogen. In some embodiments, $R^2$ is a hydrogen and $R^3$ is not a hydrogen (e.g., $R^3$ is a $C_1$-$C_6$ alkyl such as a methyl). In some embodiments, $R^2$ is not a hydrogen (e.g., $R^2$ is a $C_1$-$C_6$ alkyl such as a methyl) and $R^3$ is a hydrogen. In some embodiments, $R^2$ and $R^3$ are not both hydrogen and do not form a five to seven membered ring, together with the atoms to which they are attached.

In some embodiments, $R^2$ and $R^3$, together with the atoms to which they are attached, form a five to seven membered ring. In some embodiments, the ring is a six membered ring. In some embodiments, the ring is a five membered ring. In some embodiments, the ring is substituted with a linear, saturated $C_1$-$C_6$ alkyl. For example, the ring is substituted with a methyl at the carbon adjacent the sulfonamide nitrogen atom. In this case, the methyl substituted carbon is chiral. In some embodiments, the methyl substituted carbon is in the R configuration. In some embodiments, the methyl substituted carbon is in the S configuration.

In some embodiments, one or more of $R^{5'}$, $R^{6'}$, $R^{7'}$, $R^{8'}$ and $R^{9'}$ are halogen. In some embodiments, $R^{6'}$ and $R^{7'}$, together with the atoms to which they are attached, form a heterocycloalkyl ring, where the two adjacent $R^{6'}$ and $R^{7'}$ collectively are —O—$(CH_2)_q$—O—, where q is either 2 or 3 (e.g., 2). In some of these embodiments, one or more of $R^{5'}$, $R^{8'}$ and $R^{9'}$ are halogen.

In one aspect, the invention includes compounds of Formula IA:

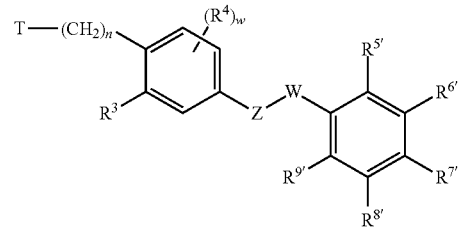

Formula IA or a salt, solvate, hydrate, or prodrug thereof, wherein:
Z is selected from the group consisting of CO, $SO_2$, O, S, and $NR^a$; and
(i) when Z is CO or $SO_2$,
    W is either absent or is selected from the group consisting of $O(CH_2)_k$, $NR^b(CH_2)_k$, $(CH_2)_k$, $(CH_2)_kO$, $(CH_2)_kS$ and $(CH_2)_kNR^b$, wherein k is 0, 1, 2 or 3, or
(ii) when Z is O, S, or $NR^a$,
    W is selected from the group consisting of $(CH_2)_kCO$ and $(CH_2)_kSO_2$, wherein k is 0, 1, 2, or 3,
$R^a$ and $R^b$ are, each independently selected from the group consisting of hydrogen, linear or branched $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ cycloalkenyl, and heterocycloalkyl;
T is selected from the group consisting of $NR^2COR^1$ and $NR^2S(O)_2R^1$;
$R^1$ is selected from the group consisting of a linear or branched $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ cycloalkenyl, heterocycloalkyl, aryl and heteroaryl,
wherein said alkyl, alkenyl, alkynyl, cycloalkyl, cycloalkenyl, heterocycloalkyl, aryl and heteroaryl are unsubstituted or substituted with one or more $R^c$,
$R^c$ is independently at each occurrence selected from the group consisting of linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, aryloxy, linear or branched $C_1$-$C_6$ haloalkoxy, linear or branched $C_1$-$C_6$ alkylsulfonyl, linear or branched $C_1$-$C_6$ thioalkyl, thioaryl, $C_3$-$C_8$ cycloalkyl, $C_3$-$C_8$ cycloalkenyl, aryl, heteroaryl, heterocycloalkyl, hydroxyl, cyano, nitro, halogen, $COR^d$, $COOR^d$, $CONR^dR^e$, $NHCOR^d$, and $NR^dR^e$;

$R^d$ and $R^e$ are, each independently selected from the group consisting of linear or branched, $C_1$-$C_6$ alkyl, linear or branched $C_2$-$C_6$ alkenyl, $C_2$-$C_6$ alkynyl, $C_3$-$C_8$ cycloalkyl, $C_3$-$C_8$ cycloalkenyl, heterocycloalkyl, aryl, and heteroaryl;

$R^2$ and $R^3$ are either (i) each independently selected from the group consisting of hydrogen, halogen, nitro, linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, $C_3$-$C_8$ cycloalkyl, $C_3$-$C_8$ cycloalkenyl, and heterocycloalkyl; or (ii) $R^2$ and $R^3$, together with the atoms to which they are attached, form a five to seven membered heterocycloalkyl or heteroaryl, wherein said ring is unsubstituted or substituted with one or more $R^m$, $R^m$ is selected from the group consisting of halogen, linear or branched $C_1$-$C_6$ alkyl, linear or branched $C_2$-$C_6$ alkenyl, linear or branched $C_2$-$C_6$ alkynyl, $C_1$-$C_6$ alkoxy, linear or branched $C_1$-$C_6$ haloalkyl, benzyloxy, $NR^dR^e$, $NHCOR^d$, and $SO_2R^d$;

$R^4$ is selected from the group consisting of halogen, linear or branched $C_1$-$C_6$ alkyl, linear or branched $C_2$-$C_6$ alkenyl, linear or branched $C_2$-$C_6$ alkynyl, and heteroalkyl, wherein said alkyl, alkenyl, alkynyl, and heteroalkyl are unsubstituted or substituted with one or more $R^f$, $R^f$ is independently at each occurrence selected from the group consisting of linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, aryloxy, linear or branched $C_1$-$C_6$ haloalkoxy, linear or branched $C_1$-$C_6$ alkylsulfonyl, linear or branched, $C_1$-$C_6$ thioalkyl, thioaryl, $C_3$-$C_8$ cycloalkyl, $C_3$-$C_8$ alkenyl, aryl, heteroaryl, heterocycloalkyl, hydroxyl, cyano, amino, nitro, halogen, $COR^g$, $COOR^g$, $CONR^gR^h$, $NHCOR^g$, and $NR^gR^h$;

$R^g$ and $R^h$ are, each independently selected from a group consisting of hydrogen, linear or branched $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ cycloalkenyl, heterocycloalkyl, aryl and heteroaryl;

t is 0, 1, 2 or 3;

$R^{5'}$, $R^{6'}$, $R^{7'}$, $R^{8'}$ and $R^{9'}$ are, each independently, selected from hydrogen, linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, benzyloxy, aryloxy, linear or branched $C_1$-$C_6$ haloalkoxy, linear or branched $C_1$-$C_6$ alkylsulfonyl, linear or branched $C_1$-$C_6$ thioalkyl, thioaryl, $C_3$-$C_8$ cycloalkyl, $C_3$-$C_8$ cycloalkenyl, aryl, heteroaryl, heterocycloalkyl, hydroxyl, cyano, amino, nitro, halogen, $COR^i$, $COOR^i$, $CONR^iR^j$, $NHCOR^i$, and $NR^iR^j$;

$R^i$ and $R^j$ are, each independently, hydrogen or a group selected from a linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, $C_3$-$C_8$ cycloalkyl, $C_3$-$C_8$ cycloalkenyl, or heterocycloalkyl, aryl and heteroaryl, wherein said alkyl, alkenyl, alkynyl, cycloalkyl, cycloalkenyl, heterocycloalkyl, aryl, and heteroaryl are unsubstituted or substituted with one or more $R^k$, $R^k$ is selected from halogen or hydroxyl, or two of $R^{5'}$, $R^{6'}$, $R^{7'}$, $R^{8'}$ and $R^{9'}$, together with the atoms to which they are attached, form a $C_5$-$C_7$ cycloalkyl, heterocycloalkyl, aryl or heteroaryl, wherein said heterocycloalkyl ring is unsubstituted or substituted with one or more $R^{m1}$ selected from $C_1$-$C_6$ alkyl and $S(O)_p(C_1$-$C_6$alkyl);

w is 0 or 1;

p is 0, 1, or 2, with the proviso that when Z is CO and $R^2$ and $R^3$, together with the atoms to which they are attached, do not form a five to seven membered ring then W is not $NR^b(CH_2)_k$.

In some embodiments, the invention includes compounds of Formula IA, wherein Z is selected from $SO_2$ or $NR^a$ and (i) when Z is $SO_2$, W is either absent or $NR^b$ and (ii) when Z is $NR^a$, W is $SO_2$. In some embodiments, the invention includes compounds of Formula IA, wherein Z is $SO_2$ and W is absent or $NR^b$. In some embodiments, the invention includes compounds of Formula IA, wherein Z is $SO_2$ and W is absent.

In some embodiments, the invention includes compounds of Formula IA, wherein Z is $NR^a$ and W is $SO_2$.

In some embodiments, the invention includes compounds of Formula IA, wherein T is $COR^1$.

In some embodiments, the invention includes compounds of Formula IA, wherein T is $S(O)_2R^1$.

In some embodiments, the invention includes compounds of Formula IA, wherein $R^{6'}$ and $R^{7'}$ or $R^{7'}$ and $R^{8'}$ together with the atoms to which they are attached form a $C_5$-$C_7$ heterocycloalkyl ring (e.g., a 1,4-dioxane ring), wherein said heterocycloalkyl ring is unsubstituted or substituted with $C_1$-$C_6$ alkyl or $S(O)_p(C_1$-$C_6$ alkyl) and the remaining $R^{6'}$ or $R^{8'}$ is selected from hydrogen, linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, benzyloxy, aryloxy, linear or branched $C_1$-$C_6$ haloalkoxy, linear or branched $C_1$-$C_6$ alkylsulfonyl, linear or branched $C_1$-$C_6$ thioalkyl, thioaryl, $C_3$-$C_8$ cycloalkyl, $C_3$-$C_8$ cycloalkenyl, aryl, heteroaryl, heterocycloalkyl, hydroxyl, cyano, amino, nitro, halogen, $COR^i$, $COOR^i$, $CONR^iR^j$, $NHCOR^i$, and $NR^iR^j$ or at least one of $R^{6'}$, $R^{7'}$, or $R^{8'}$ is $C^1$-$C^6$ alkoxy (e.g., methoxy).

In some embodiments, the invention includes compounds of Formula IA, wherein $R^2$ and $R^3$ together with the atoms to which they are attached form a five or six membered heterocycloalkyl ring. In some embodiments, the invention includes compounds of Formula IA, wherein $R^2$ and $R^3$ together with the atoms to which they are attached form a pyrrolidine ring or a piperidine ring. In some embodiments, the invention includes compounds of Formula IA, wherein $R^2$ and $R^3$ together with the atoms to which they are attached form a pyrrolidine ring.

In one aspect, the invention includes compounds of Formula IB:

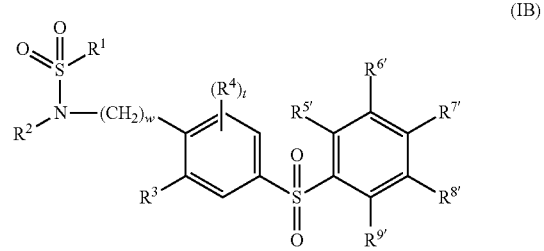

(IB)

or a salt, solvate, hydrate, or prodrug thereof, wherein $R^1$, $R^2$, $R^3$, $R^4$, $R^{5'}$, $R^{6'}$, $R^{7'}$, $R^{8'}$, $R^{9'}$, t, and w are as described herein. In one aspect, $R^1$, $R^2$, $R^3$, $R^4$, $R^{5'}$, $R^{6'}$, $R^{7'}$, $R^{8'}$, $R^{9'}$, t, and w are as described for Formula IA.

In one aspect, the invention includes compounds of Formula IC:

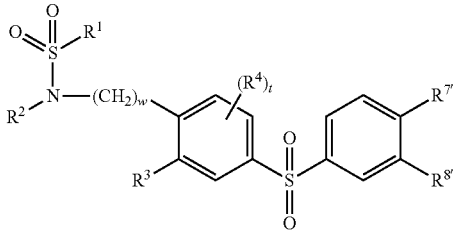

(IC)

or a salt, solvate, hydrate, or prodrug thereof, wherein $R^1$, $R^2$, $R^3$, $R^4$, $R^{7'}$, $R^{8'}$, t, and w are as described herein. In one aspect, $R^1$, $R^2$, $R^3$, $R^4$, $R^{7'}$, $R^{8'}$, t, and w are as described for Formula IA.

In one aspect, the invention includes compounds of Formula ID:

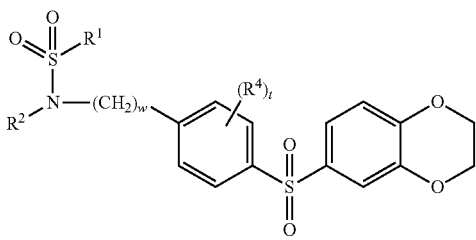

(ID)

or a salt, solvate, hydrate, or prodrug thereof, wherein $R^1$, $R^2$, $R^4$, t, and w are as described herein. In one aspect, $R^1$, $R^2$, $R^4$, t, and w are as described for Formula IA.

In some embodiments, the invention includes compounds of Formulae IA, IB, IC, or ID, wherein w is 0.

In some embodiments, the invention includes compounds of Formulae IA, IB, IC, or ID, wherein w is 1.

In one aspect, the invention includes compounds of Formula II or a salt, solvate, hydrate, or prodrug thereof:

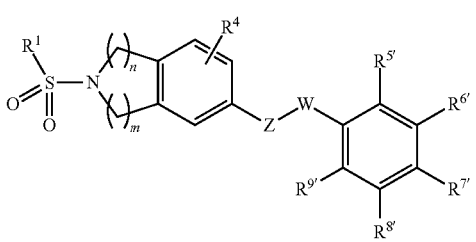

Formula II wherein:

m is between 0 and 4 and n is between 0 and 4, thereby forming a five to seven membered heteroaryl or a five to seven membered heterocycloalkyl ring optionally containing one or more double bonds, wherein the five to seven membered heteroaryl or heterocycloalkyl is optionally substituted with one or more linear or branched, saturated or unsaturated $C_1$-$C_6$ alkyl;

Z is selected from CO, $SO_2$, O, S, or $NR^a$; and
(i) when Z is CO or $SO_2$,
W is either absent or is selected from the group consisting of $O(CH_2)_k$, $NR^b(CH_2)_k$, $(CH_2)_k$, $(CH_2)_kO$, $(CH_2)_kS$ and $(CH_2)_kNR^b$, wherein k is between 1 and 3, or
(ii) when Z is O, S, or $NR^a$,
W is selected from the group consisting of $(CH_2)_kCO$ and $(CH_2)_kSO_2$, wherein k is between 1 and 3,
$R^a$ and $R^b$ are, each independently, hydrogen or a group selected from a linear or branched, saturated or unsaturated $C_1$-$C_6$ alkyl, a saturated or unsaturated $C_3$-$C_6$ cycloalkyl or heterocycloalkyl;

$R^1$ is selected from the group consisting of a linear or branched, saturated or unsaturated $C_1$-$C_6$ alkyl, a saturated or unsaturated $C_3$-$C_8$ cycloalkyl or heterocycloalkyl, an aryl and heteroaryl,
wherein said alkyl, cycloalkyl, heterocycloalkyl, aryl or heteroaryl is unsubstituted or substituted with one or more $R^c$, $R^c$ is independently at each occurrence selected from the group consisting of: linear or branched, saturated or unsaturated $C_1$-$C_6$ alkyl, linear or branched, saturated or unsaturated $C_1$-$C_6$ haloalkyl, linear or branched, saturated or unsaturated $C_1$-$C_6$ alkoxy or aryloxy, linear or branched, saturated or unsaturated $C_1$-$C_6$ haloalkoxy, linear or branched, saturated or unsaturated $C_1$-$C_6$ alkylsulfonyl, linear or branched, saturated or unsaturated $C_1$-$C_6$ thioalkyl or thioaryl, saturated or unsaturated $C_3$-$C_8$ cycloalkyl, aryl, heteroaryl, heterocycloalkyl, hydroxyl, cyano, amino, nitro, halogen, $COR^d$, $COOR^d$, $CONR^dR^e$, $NHCOR^d$, and $NR^dR^e$;

$R^d$ and $R^e$ are, each independently, hydrogen or a group selected from a linear or branched, saturated or unsaturated $C_1$-$C_6$ alkyl, a saturated or unsaturated $C_3$-$C_8$ cycloalkyl or heterocycloalkyl, an aryl and a heteroaryl;

$R^4$ is selected from hydrogen, or a linear or branched, saturated or unsaturated $C_1$-$C_6$ alkyl or heteroalkyl,
wherein said alkyl or heteroalkyl is unsubstituted or substituted with one or more $R^f$, $R^f$ is independently at each occurrence selected from the group consisting of: linear or branched, saturated or unsaturated $C_1$-$C_6$ alkyl; linear or branched, saturated or unsaturated $C_1$-$C_6$ haloalkyl; linear or branched, saturated or unsaturated $C_1$-$C_6$ alkoxy or aryloxy; linear or branched, saturated or unsaturated $C_1$-$C_6$ haloalkoxy; linear or branched, saturated or unsaturated $C_1$-$C_6$ alkylsulfonyl; linear or branched, saturated or unsaturated $C_1$-$C_6$ thioalkyl or thioaryl; saturated or unsaturated $C_3$-$C_8$ cycloalkyl; aryl; heteroaryl; heterocycloalkyl; hydroxyl; cyano; amino; nitro; halogen; $COR^g$; $COOR^g$; $CONR^gR^h$; $NHCOR^g$, and $NR^gR^h$;

$R^g$ and $R^h$ are, each independently, hydrogen or a group selected from a linear or branched, saturated or unsaturated $C_1$-$C_6$ alkyl, a saturated or unsaturated $C_3$-$C_8$ cycloalkyl or heterocycloalkyl, an aryl and a heteroaryl;

$R^{5'}$, $R^{6'}$, $R^{7'}$, $R^{8'}$ and $R^{9'}$ are, each independently, selected from: hydrogen; linear or branched, saturated or unsaturated $C_1$-$C_6$ alkyl; linear or branched, saturated or unsaturated $C_1$-$C_6$ haloalkyl; linear or branched, saturated or unsaturated $C_1$-$C_6$ alkoxy or aryloxy; linear or branched, saturated or unsaturated $C_1$-$C_6$ haloalkoxy; linear or branched, saturated or unsaturated $C_1$-$C_6$ alkylsulfonyl; linear or branched, saturated or unsaturated $C_1$-$C_6$ thioalkyl or thioaryl; saturated or unsaturated $C_3$-$C_8$ cycloalkyl; aryl; heteroaryl; heterocycloalkyl; hydroxyl; cyano; amino; nitro; halogen; $COR^i$; $COOR^i$; $CONR^iR^j$; $NHCOR^i$, and $NR^iR^j$;

$R^i$ and $R^j$ are, each independently, hydrogen or a group selected from a linear or branched, saturated or unsaturated $C_1$-$C_6$ alkyl, a saturated or unsaturated $C_3$-$C_8$ cycloalkyl or heterocycloalkyl, an aryl and a heteroaryl; or two of $R^{5'}$, $R^{6'}$, $R^{7'}$, $R^{8'}$ and $R^{9'}$, together with the atoms to which they are attached, form a $C_5$-$C_7$ cycloalkyl, heterocycloalkyl, aryl, or heteroaryl.

Compounds of the invention include compounds of Formula II that activate PKM2 by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more.

In some embodiments, the invention includes compounds of Formula II wherein $R^1$ is a $C_1$-$C_6$ alkyl, such as a $C_1$-$C_3$ alkyl (e.g., a methyl or an ethyl). In some embodiments, $R^1$ is an unsubstituted or substituted phenyl.

In some embodiments, Z is CO and W is absent. In some embodiments, Z is $SO_2$ and W is absent. In some embodiments, Z is CO and W is $(CH_2)S$. In some embodiments, Z is CO and W is $(CH_2)O$. In some embodiments, Z is CO and W is $O(CH_2)$. In some embodiments, Z is O and W is $(CH_2)CO$.

In some embodiments, $R^4$ is not hydrogen. In some embodiments, $R^4$ is hydrogen.

In some embodiments, m is 0 and n is 3. In some embodiments, m is 2 and n is 0. In some embodiments, m is 1 and n is 1. In some embodiments, none of carbon atoms of the five to seven membered heteroaryl or heterocycloalkyl ring is substituted. In some embodiments, a ring carbon adjacent the sulfonamide nitrogen atom is substituted with one linear, saturated $C_1$-$C_6$ alkyl (e.g., methyl). In this case, thealkyl substituted carbon is chiral. In some embodiments, the alkyl (e.g., methyl) substituted carbon is in the R configuration. In some embodiments, the alkyl (e.g., methyl) substituted carbon is in the S configuration.

In some embodiments, one or more of $R^{5'}$, $R^{6'}$, $R^{7'}$, $R^{8'}$ and $R^{9'}$ are halogen. In some embodiments, $R^{6'}$ and $R^{7'}$, together with the atoms to which they are attached, form a heterocycloalkyl ring, where the two adjacent $R^{6'}$ and $R^{7'}$ collectively are —O—$(CH_2)_q$—O—, where q is either 2 or 3 (e.g., 2). In some of these embodiments, one or more of $R^{5'}$, $R^{8'}$ and $R^{9'}$ are halogen.

In one aspect, the invention includes compounds of Formula IIA:

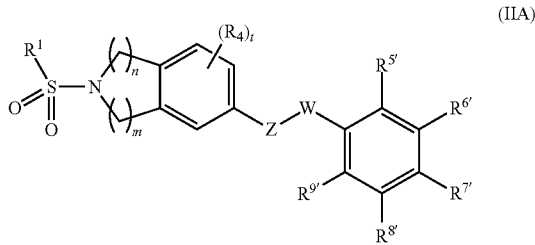

(IIA)

or a salt, solvate, hydrate or prodrug thereof, wherein:
m is 0, 1, 2, 3, or 4 and n is 0, 1, 2, 3 or 4, thereby forming a five to seven membered heteroaryl or a five to seven membered heterocycloalkyl ring, wherein the five to seven membered heteroaryl or heterocycloalkyl ring is optionally substituted with one or more $R^m$,
$R^m$ is selected from the group consisting of linear or branched $C_1$-$C_6$ alkyl, linear or branched $C_2$-$C_6$ alkenyl, and linear or branched $C_2$-$C_6$ alkynyl;

Z is selected from the group consisting of CO, $SO_2$, O, S, and $NR^a$; and
(i) when Z is CO or $SO_2$,
W is either absent or is selected from the group consisting of $O(CH_2)_k$, $NR^b(CH_2)_k$, $(CH_2)_k$, $(CH_2)_kO$, $(CH_2)_kS$ and $(CH_2)_kNR^b$, wherein k is 0, 1, 2, or 3, or
(ii) when Z is O, S, or $NR^a$,
W is selected from the group consisting of $(CH_2)_kCO$ and $(CH_2)_kSO_2$, wherein k is 0, 1, 2, or 3,
$R^a$ and $R^b$ are, each independently selected from the group consisting of hydrogen, linear or branched $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ alkenyl, and heterocycloalkyl;
$R^1$ is selected from the group consisting of linear or branched $C_1$-$C_6$ alkyl, linear or branched $C_2$-$C_6$ alkenyl, $C_2$-$C_6$ alkynyl, $C_3$-$C_8$ cycloalkyl, $C_3$-$C_8$ cycloalkenyl, heterocycloalkyl, aryl and heteroaryl,
wherein said alkyl, alkenyl, alkynyl, cycloalkyl, cycloalkenyl, heterocycloalkyl, aryl and heteroaryl are unsubstituted or substituted with one or more $R^c$,
$R^c$ is independently at each occurrence selected from the group consisting of linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, aryloxy, linear or branched $C_1$-$C_6$ haloalkoxy, linear or branched $C_1$-$C_6$ alkylsulfonyl, linear or branched $C_1$-$C_6$ thioalkyl, thioaryl, $C_3$-$C_8$ cycloalkyl, $C_3$-$C_8$ cycloalkenyl, aryl, heteroaryl, heterocycloalkyl, hydroxyl, cyano, amino, nitro, halogen, $COR^d$, $COOR^d$, $CONR^dR^e$, $NHCOR^d$, and $NR^dR^e$;
$R^d$ and $R^e$ are, each independently selected from the group consisting of hydrogen, linear or branched $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ cycloalkenyl, heterocycloalkyl, aryl and heteroaryl;
$R^4$ is selected from hydrogen, halogen, linear or branched $C_1$-$C_6$ alkyl, linear or branched $C_2$-$C_6$ alkenyl, linear or branched $C_2$-$C_6$ alkynyl, and heteroalkyl,
wherein said alkyl, alkenyl, alkynyl, and heteroalkyl are unsubstituted or substituted with one or more $R^f$,
$R^f$ is independently at each occurrence selected from the group consisting of linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, aryloxy, linear or branched $C_1$-$C_6$ haloalkoxy, linear or branched $C_1$-$C_6$ alkylsulfonyl, linear or branched $C_1$-$C_6$ thioalkyl, thioaryl, $C_3$-$C_8$ cycloalkyl, $C_3$-$C_8$ cycloalkenyl, aryl, heteroaryl, heterocycloalkyl, hydroxyl, cyano, amino, nitro, halogen, $COR^g$, $COOR^g$, $CONR^gR^h$, $NHCOR^g$, and $NR^gR^h$;
$R^g$ and $R^h$ are, each independently selected from the group consisting of hydrogen, linear or branched $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ cycloalkenyl, heterocycloalkyl, aryl and heteroaryl;
t is 0, 1, 2, or 3;
$R^{5'}$, $R^{6'}$, $R^{7'}$, $R^{8'}$ and $R^{9'}$ are, each independently, selected from hydrogen, linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, aryloxy, linear or branched $C_1$-$C_6$ haloalkoxy, linear or branched $C_1$-$C_6$ alkylsulfonyl, linear or branched $C_1$-$C_6$ thioalkyl or thioaryl, $C_3$-$C_8$ cycloalkyl, $C_3$-$C_8$ cycloalkenyl, aryl, heteroaryl, heterocycloalkyl, hydroxyl, cyano, amino, nitro, halogen, $COR^i$, $COOR^i$, $CONR^iR^j$, $NHCOR^i$, and $NR^iR^j$;

$R^i$ and $R^j$ are, each independently selected from the group consisting of hydrogen, linear or branched $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ cycloalkenyl, heterocycloalkyl, aryl and heteroaryl, wherein said alkyl, alkenyl, alkynyl, cycloalkyl, cycloalkenyl, heterocycloalkyl, aryl, and heteroaryl are unsubstituted or substituted with one or more $R^k$, $R^k$ is selected from the group consisting of halogen and hydroxyl, or two of $R^{5'}$, $R^{6'}$, $R^{7'}$, $R^{8'}$ and $R^{9'}$, together with the atoms to which they are attached, form a $C_5$-$C_7$ cycloalkyl, heterocycloalkyl, aryl or heteroaryl.

In some embodiments, the invention includes compounds of Formula IIA, wherein Z is selected from $SO_2$ and $NR^a$; and (i) when Z is $SO_2$, W is either absent or $NR^b$ or (ii) when Z is $NR^a$, W is $SO_2$.

In some embodiments, the invention includes compounds of Formula IIA, wherein Z is $SO_2$ and W is absent. In some embodiments, the invention includes compounds of Formula IIA, wherein n is 0 or 1. In some embodiments, the invention includes compounds of Formula IIA, wherein m is 1 or 2. In some embodiments, the invention includes compounds of Formula IIA, wherein n is 0 and m is 2. In some embodiments, the invention includes compounds of Formula IIA, wherein n is 1 and m is 1.

In some embodiments, the invention includes compounds of Formula IIa, wherein $R^m$ is selected from the group consisting of linear or branched $C_1$-$C_6$ alkyl, linear or branched $C_2$-$C_6$ alkenyl, and linear or branched $C_2$-$C_6$ alkynyl. In some embodiments, the invention includes compounds of Formula IIA, wherein the five to seven membered heterocycloalkyl ring is unsubstituted.

In one aspect, the invention includes compounds of Formula IIB:

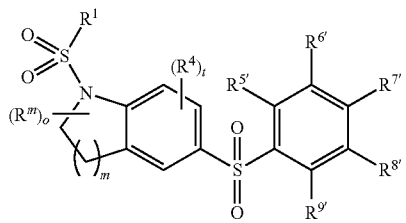

(IIB)

or a salt, solvate, hydrate, or prodrug thereof, wherein $R^1$, $R^m$, $R^4$, $R^{5'}$, $R^{6'}$, $R^{7'}$, $R^{8'}$, t, m, and $R^{9'}$ are as described herein. In one aspect, $R^1$, $R^m$, $R^4$, $R^{5'}$, $R^{6'}$, $R^{7'}$, $R^{8'}$, t, m, and $R^{9'}$ are as described for Formula IIA and o is 0 or 1.

In one aspect, the invention includes a compound of Formula IIC:

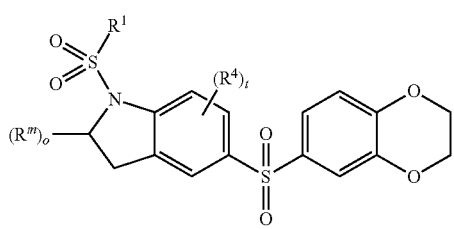

(IIC)

or a salt, solvate, hydrate, or prodrug thereof, wherein $R^1$, $R^m$, t, and $R^4$ are as described herein. In one aspect, $R^1$, $R^m$, t, and $R^4$ are as described for Formula IIA and o is 0 or 1.

In some embodiments, the invention includes compounds of Formulae IA, IB, IC, IIA, IIB, and IIC, wherein $R^m$ is $C_1$-$C_6$ alkyl. In some embodiments, the invention includes compounds of Formulae IA, IB, IC, IIA, IIB, and IIC, wherein $R^m$ is $CH_3$.

In one aspect, the invention includes compounds of Formula IID:

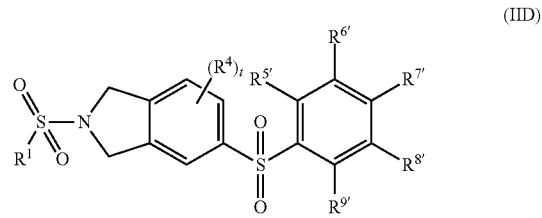

(IID)

or a salt, solvate, hydrate, or prodrug thereof, wherein $R^1$, $R^4$, $R^{5'}$, $R^{6'}$, $R^{7'}$, $R^{8'}$, t, and $R^{9'}$ are as described herein.

In one aspect, the invention includes compounds of Formula IIE:

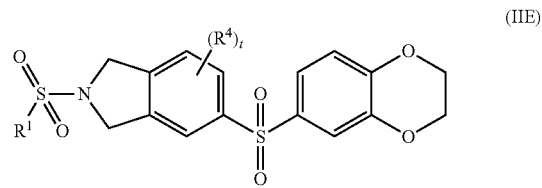

(IIE)

or a salt, solvate, hydrate, or prodrug thereof, wherein $R^1$, $R^4$, and t are as described herein.

In one aspect, the invention includes compounds of Formula III or a salt, solvate, hydrate, or prodrug thereof:

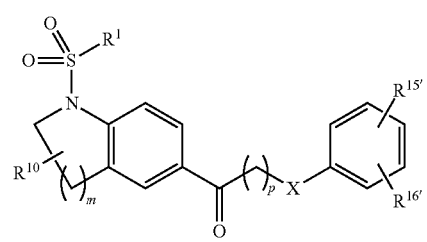

Formula III wherein:
m is between 1 and 3; p is between 1 and 3; X is either O or S;
$R^1$ is selected from the group consisting of a linear or branched, saturated or unsaturated $C_1$-$C_6$ alkyl, a saturated or unsaturated $C_3$-$C_8$ cycloalkyl or heterocycloalkyl, an aryl and heteroaryl,
wherein said alkyl, cycloalkyl, heterocycloalkyl, aryl or heteroaryl is unsubstituted or substituted with one or more $R^c$,
wherein $R^c$ is independently at each occurrence selected from the group consisting of: linear or branched, saturated or unsaturated $C_1$-$C_6$ alkyl; linear or branched, saturated or unsaturated $C_1$-$C_6$ haloalkyl; linear or branched, saturated or unsaturated $C_1$-$C_6$ alkoxy or aryloxy; linear or branched, saturated or unsaturated $C_1$-$C_6$ haloalkoxy; linear or branched, saturated or unsaturated $C_1$-$C_6$ alkylsulfonyl; linear or branched, saturated or unsaturated $C_1$-$C_6$ thioalkyl or thioaryl; saturated or unsaturated $C_3$-$C_8$ cycloalkyl; aryl; heteroaryl; heterocycloalkyl; hydroxyl; cyano; amino; nitro; halogen; $COR^d$; $COOR^d$; $CONR^dR^e$; $NHCOR^d$, and $NR^dR^e$;

$R^d$ and $R^e$ are, each independently, hydrogen or a group selected from a linear or branched, saturated or unsaturated $C_1$-$C_6$ alkyl, a saturated or unsaturated $C_3$-$C_8$ cycloalkyl or heterocycloalkyl, an aryl and a heteroaryl;

$R^{15'}$ and $R^{16'}$ are either, (i) each independently, selected from the group consisting of: hydrogen; a linear or branched, saturated or unsaturated $C_1$-$C_6$ alkyl; linear or branched, saturated or unsaturated $C_1$-$C_6$ haloalkyl; linear or branched, saturated or unsaturated $C_1$-$C_6$ alkoxy or aryloxy; linear or branched, saturated or unsaturated $C_1$-$C_6$ haloalkoxy; linear or branched, saturated or unsaturated $C_1$-$C_6$ alkylsulfonyl; linear or branched, saturated or unsaturated $C_1$-$C_6$ thioalkyl or thioaryl; saturated or unsaturated $C_3$-$C_8$ cycloalkyl; aryl; heteroaryl; heterocycloalkyl; hydroxyl; cyano; amino; nitro; halogen; $COR^i$; $COOR^i$; $CONR^iR^j$; $NHCOR^i$, and $NR^iR^j$;

$R^i$ and $R^j$ are, each independently, hydrogen or a group selected from a linear or branched, saturated or unsaturated $C_1$-$C_6$ alkyl, a saturated or unsaturated $C_3$-$C_8$ cycloalkyl or heterocycloalkyl, an aryl and a heteroaryl;

or (ii) $R^{15'}$ and $R^{16'}$, together with the atoms to which they are attached, form a $C_5$-$C_7$ cycloalkyl, heterocycloalkyl, aryl, or heteroaryl;

$R^{10}$ is either hydrogen or a linear or branched, saturated or unsaturated $C_1$-$C_6$ alkyl.

Compounds of the invention include compounds of Formula III that activate PKM2 by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more.

In some embodiments, $R^1$ is a $C_1$-$C_6$ alkyl, such as a $C_1$-$C_3$ alkyl (e.g., a methyl or an ethyl). In some embodiments, $R^1$ is an unsubstituted or substituted phenyl.

In some embodiments, p is 1 and X is O. In some embodiments, p is 1 and X is S.

In some embodiments, m is 2. In some embodiments, m is 1. In some embodiments, $R^{10}$ is hydrogen. In some embodiments, $R^{10}$ is linear, saturated $C_1$-$C_6$ alkyl. For example, $R^{10}$ is a methyl that is substituted at the carbon adjacent the sulfonamide nitrogen atom. In this case, the methyl substituted carbon is chiral. In some embodiments, the methyl substituted carbon is in the R configuration. In some embodiments, the methyl substituted carbon is in the S configuration.

In some embodiments, one or both of $R^{15'}$ and $R^{16'}$ are halogen. In some embodiments, $R^{15'}$ and $R^{16'}$ are adjacent and, together with the atoms to which they are attached, form a heterocycloalkyl ring, where the two adjacent $R^{6'}$ and $R^{7'}$ collectively are —O—$(CH_2)_q$—O—, where q is either 2 or 3 (e.g., 2).

In some embodiments, the invention includes compounds of Formulae I, IA, IB, IC, ID, II, IIA, IIB, IIC, IID, IIE, and III, wherein $R^1$ is selected from $C_1$-$C_6$ alkyl, $C_2$-$C_6$ alkenyl, $C_2$-$C_6$ alkynyl, $C_1$-$C_6$ haloalkyl, aryl, heteroaryl, $C_3$-$C_8$ cycloalkyl, and $C_3$-$C_8$ cycloalkenyl.

In some embodiments, the invention includes compounds of Formulae I, IA, IB, IC, ID, II, IIA, IIB, IIC, IID, IIE, and III, wherein $R^1$ is selected from $C_1$-$C_6$ alkyl, $C_1$-$C_6$ haloalkyl, aryl, heteroaryl, and $C_3$-$C_8$ cycloalkyl.

In some embodiments, the invention includes compounds of Formulae I, IA, IB, IC, ID, II, IIA, IIB, IIC, IID, IIE, and III, wherein $R^1$ is methyl, ethyl, propyl, isopropyl, butyl, isobutyl, $CF_3$, $CHF_2$, $CH_2F$, dihydrobenzo[1,4]dioxine, phenyl, and cyclopropyl, wherein the $R^1$ are optionally substituted with $R^c$.

In some embodiments, the invention includes compounds of Formulae I, IA, IB, IC, ID, II, IIA, IIB, IIC, IID, IIE, and III, wherein $R^1$ is methyl, substituted methyl, ethyl, propyl, isobutyl, $CF_3$, substituted phenyl, unsubstituted phenyl, dihydrobenzo[1,4]dioxine, and cyclopropyl.

In some embodiments, the invention includes compounds of Formulae I, IA, IB, IC, ID, II, IIA, IIB, IIC, IID, IIE, and III, wherein $R^1$ is selected from methyl, ethyl, propyl, isopropyl, butyl, isobutyl, and phenyl.

In some embodiments, the invention includes compounds of Formulae I, IA, IB, IC, ID, II, IIA, IIB, IIC, IID, IIE, and III, wherein $R^1$ is substituted with one or more $R^c$ selected from $C_1$-$C_6$ alkyl, $C_2$-$C_6$ alkenyl, $C_2$-$C_6$ alkynyl, $C_1$-$C_6$ alkoxy, halogen, unsubstituted aryl, substituted aryl, and $C_1$-$C_6$ haloalkyl.

In some embodiments, the invention includes compounds of Formulae I, IA, IB, IC, ID, II, IIA, IIB, IIC, IID, IIE, and III, wherein $R^1$ is substituted with one or more $R^c$ selected from $C_1$-$C_6$ alkyl, $C_1$-$C_6$ alkoxy, halogen, unsubstituted aryl, and $C_1$-$C_6$ haloalkyl.

In some embodiments, the invention includes compounds of Formulae I, IA, IB, IC, ID, II, IIA, IIB, IIC, IID, IIE, and III, wherein $R^1$ is substituted with one or more $R^c$ selected from methyl, $OCH_3$, F, Cl, unsubstituted phenyl, and $CF^3$.

In some embodiments, the invention includes compounds of Formulae I, IA, IB, IC, ID, II, IIA, IIB, IIC, IID, IIE, and III, wherein $R^1$ is substituted with one $R^c$.

In some embodiments, the invention includes compounds of Formulae I, IA, IB, IC, ID, II, IIA, IIB, IIC, IID, IIE, and III, wherein $R^1$ is substituted with two $R^c$.

In some embodiments, the invention includes compounds of Formulae I, IA, IB, IC, and ID wherein $R^2$ is selected from $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkenyl, and $C_1$-$C_6$ haloalkyl.

In some embodiments, the invention includes compounds of Formulae I, IA, IB, IC, and ID wherein $R^2$ is selected from $C_1$-$C_6$ alkyl, $C_2$-$C_6$ alkenyl, $C_2$-$C_6$ alkynyl, and $C_1$-$C_6$ haloalkyl.

In some embodiments, the invention includes compounds of Formulae IA, IB, IC, and ID wherein $R^2$ is $C_1$-$C_6$ alkyl.

In some embodiments, the invention includes compounds of Formulae IA, IB, IC, and ID wherein $R^2$ is $C_1$-$C_6$ alkyl and $R^1$ is $C_1$-$C_6$ alkyl or $C_1$-$C_6$ alkenyl.

In some embodiments, the invention includes compounds of Formulae I, IA, IB, IC, and ID wherein $R^2$ is selected from methyl, ethyl, isopropyl, propyl, butyl, isobutyl, propenyl, propynyl, $CHF_2$, $CH_2F$, and $CF_3$.

In some embodiments, the invention includes compounds of Formulae I, IA, IB, IC, and ID, wherein $R^2$ is selected from methyl, ethyl, isopropyl, propyl, propenyl, propynyl, butyl, and $CF_3$.

In some embodiments, the invention includes compounds of Formulae I, IA, IB, and IC, wherein $R^2$ and $R^3$ together with the atoms to which they are attached, form a five, six, or seven membered heterocycloalkyl ring.

In some embodiments, the invention includes compounds of Formulae I, IA, IB, and IC, $R^2$ and $R^3$ together with the atoms to which they are attached form a five membered heterocycloalkyl ring.

In some embodiments, the invention includes compounds of Formulae I, IA, IB, and IC, $R^2$ and $R^3$ together with the atoms to which they are attached form a six membered heterocycloalkyl ring.

In some embodiments, the invention includes compounds of Formulae I, IA, IB, and IC, $R^2$ and $R^3$ together with the atoms to which they are attached form a heterocycloalkyl ring selected from pyrrolidine and piperidine.

In some embodiments, the invention includes compounds of Formulae I, IA, IB, and IC, $R^2$ and $R^3$ together with the atoms to which they are attached form a pyrrolidine ring.

In some embodiments, the invention includes compounds of Formulae I, IA, IB, and IC, $R^2$ and $R^3$ together with the atoms to which they are attached form a piperidine ring.

In some embodiments, the invention includes compounds of Formulae I, IA, IB, and IC, wherein $R^3$ is hydrogen.

In some embodiments, the invention includes compounds of Formulae I, IA, IB, and IC, wherein $R^3$ is not halogen or $CF_3$.

In some embodiments, the invention includes compounds of Formulae I, IA, IB, IC, ID, II, IIA, IIB, IIC, IID, and IIE, wherein $R^4$ is halogen.

In some embodiments, the invention includes compounds of Formulae I, IA, IB, IC, ID, II, IIA, IIB, IIC, IID, and IIE, wherein $R^4$ is F.

In some embodiments, the invention includes compounds of Formulae I, IA, IB, IC, ID, IIA, IIB, IIC, IID, and IIE, wherein t is 0.

In some embodiments, the invention includes compounds of Formulae I, IA, IB, IC, ID, IIA, IIB, TIC, IID, and IIE, wherein $R^4$ is halogen and t is 1.

In some embodiments, the invention includes compounds of Formulae I, IA, IB, IC, ID, IIA, IIB, IIC, IID, and IIE, wherein $R^4$ is halogen and t is 2.

In some embodiment, the invention includes compounds of Formulae I, IA, IB, II, IIA, JIB, and IID, wherein one of $R^{5'}$, $R^{6'}$, $R^{7'}$, $R^{8'}$, or $R^{9'}$ is hydrogen.

In some embodiment, the invention includes compounds of Formulae I, IA, IB, II, IIA, IIB, and IID, wherein at least one of $R^{5'}$, $R^{6'}$, $R^{7'}$, $R^{8'}$, or $R^{9'}$ is hydrogen. In some embodiment, the invention includes compounds of Formulae I, IA, IB, II, IIA, IIB, and IID, wherein two of $R^{5'}$, $R^{6'}$, $R^{7'}$, $R^{8'}$, and $R^{9'}$ are hydrogen. In some embodiment, the invention includes compounds of Formulae I, IA, IB, II, IIA, IIB, and IID, wherein at least two of $R^{5'}$, $R^{6'}$, $R^{7'}$, $R^{8'}$, and $R^{9'}$ are hydrogen.

In some embodiment, the invention includes compounds of Formulae I, IA, IB, II, IIA, IIB, and IID, wherein three of $R^{5'}$, $R^{6'}$, $R^{7'}$, $R^{8'}$, and $R^{9'}$ are hydrogen. In some embodiment, the invention includes compounds of Formulae I, IA, IB, II, IIA, IIB, and IID, wherein at least three of $R^{5'}$, $R^{6'}$, $R^{7'}$, $R^{8'}$, and $R^{9'}$ are hydrogen In some embodiment, the invention includes compounds of Formulae I, IA, IB, II, IIA, IIB, and IID, wherein four of $R^{5'}$, $R^{6'}$, $R^{7'}$, $R^{8'}$, and $R^{9'}$ are hydrogen. In some embodiment, the invention includes compounds of Formulae I, IA, IB, II, IIA, IIB, and IID, wherein at least four of $R^{5'}$, $R^{6'}$, $R^{7'}$, $R^{8'}$, and $R^{9'}$ are hydrogen In some embodiment, the invention includes compounds of Formula I, IA, IB, II, IIA, IIB, and IID, wherein all of $R^{5'}$, $R^{6'}$, $R^{7'}$, $R^{8'}$, and $R^{9'}$ are hydrogen.

In some embodiments, the invention includes compounds of Formulae I, IA, IB, II, IIA, IIB, and IID, wherein $R^{7'}$ and $R^{8'}$ together with the atoms to which they are attached form a heterocycloalkyl ring. The heterocycloalkyl ring (e.g., a 1,4 dioxane ring) is fused to the aromatic ring to which $R^{7'}$ and $R^{8'}$ are attached e.g.,

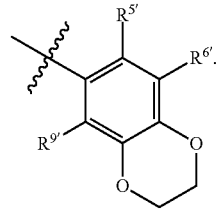

In some embodiments, the invention includes compounds of Formulae I, IA, IB, II, IIA, IIB, and IID, wherein $R^{7'}$ and $R^{8'}$ together with the atoms to which they are attached form a heterocycloalkyl ring and $R^{5'}$, $R^{6'}$, and $R^{9'}$ are each hydrogen.

In some embodiments, the invention includes compounds of Formulae I, IA, IB, II, IIA, IIB, and IID, wherein $R^{7'}$ and $R^{8'}$ together with the atoms to which they are attached form a heterocycloalkyl ring selected from 1,4-dioxane, 1,3-dioxole, tetrahydropyran, tetrahydrothiophene, and pyrrolidine.

In some embodiments, the invention includes compounds of Formulae I, IA, IB, II, IIA, IIB, and IID, wherein $R^{7'}$ and $R^{8'}$ together with the atoms to which they are attached form a heterocycloalkyl ring selected from 1,4-dioxane and pyrrolidine.

In some embodiments, the invention includes compounds of Formulae I, IA, IB, II, IIA, IIB, and IID, wherein $R^{7'}$ and $R^{8'}$ together with the atoms to which they are attached form a 1,4-dioxane ring and $R^{5'}$, $R^{6'}$, and $R^{9'}$ are each hydrogen.

In some embodiments, the invention includes compounds of Formulae I, IA, IB, II, IIA, IIB, and IID, wherein the ring formed by $R^{7'}$ and $R^{8'}$ is unsubstituted.

In some embodiments, the invention includes compounds of Formulae I, IA, IB, II, IIA, IIB, and IID, wherein, wherein the ring formed by $R^{7'}$ and $R^{8'}$ is substituted with one $R^{m1}$.

In some embodiments, the invention includes compounds of Formulae I, IA, IB, II, IIA, IIB, and IID, wherein the ring formed by $R^{7'}$ and $R^{8'}$ is substituted with two $R^{m1}$.

In some embodiments, the invention includes compounds of Formulae I, IA, IB, II, IIA, IIB, land IID, wherein the ring formed by $R^{7'}$ and $R^{8'}$ is substituted with one or more $R^{m1}$ and $R^{m1}$ is selected from methoxy, benzyloxy, methyl, Cl, Br, F, $NR^dR^e$, $NHCOR^d$, and $SOCH_3$.

In some embodiments, the invention includes compounds of Formulae I, IA, IB, II, IIA, IIB, and IID, wherein the ring formed by $R^{7'}$ and $R^{8'}$ is substituted with one or more $R^{m1}$ and $R^{m1}$ is selected from benzyloxy, $NR^dR^e$, $NHCOR^d$, and $SOCH_3$.

In some embodiments, the invention includes compounds of Formulae I, IA, IB, II, IIA, IIB, and IID, wherein one of $R^{5'}$, $R^{6'}$, $R^{7'}$, $R^{8'}$, and $R^{9'}$ is $NR^iR^j$ or $NHCOR^i$ and the remaining $R^{5'}$, $R^{6'}$, $R^{7'}$, $R^{8'}$, and $R^{9'}$ are hydrogen.

In some embodiments, the invention includes compounds of Formulae I, IA, IB, II, IIA, IIB, and IID, wherein one of $R^{5'}$, $R^{6'}$, $R^{7'}$, $R^{8'}$, and $R^{9'}$ is $NR^iR^j$ or NHCORi and the remaining $R^{5'}$, $R^{6'}$, $R^{7'}$, $R^{8'}$, and $R^{9'}$ are hydrogen or two of $R^{5'}$, $R^{6'}$, $R^{7'}$, $R^{8'}$, and $R^{9'}$ are taken together with the atoms to which they are attached form a heterocycloalkyl ring and the remaining $R^{5'}$, $R^{6'}$, $R^{7'}$, $R^{8'}$, and $R^9$ are hydrogen.

In some embodiments, the invention includes compounds of Formulae I, IA, IB, II, IIA, IIB, and IID, wherein one of $R^{5'}$, $R^{6'}$, $R^{7'}$, $R^{8'}$, and $R^{9'}$ is $NR^iR^j$ or NHCORi and the remaining $R^{5'}$, $R^{6'}$, $R^{7'}$, $R^{8'}$, and $R^{9'}$ are hydrogen or two of $R^{5'}$, $R^{6'}$, $R^{7'}$, $R^{8'}$, and $R^{9'}$ are taken together with the atoms to which they are attached form a heterocycloalkyl ring and the remaining $R^{5'}$, $R^{6'}$, $R^{7'}$, $R^{8'}$, and $R^9$ are hydrogen.

In some embodiments, the invention includes compounds of Formula IA, wherein T is S(O)$_2$R$^1$, w is 0, and R$^1$ is C$_1$-C$_6$ alkyl or aryl.

In some embodiments, the invention includes compounds of Formula IA, wherein T is S(O)$_2$R$^1$, w is 1, and R$^1$ is C$_1$-C$_6$ alkyl or aryl.

In some embodiments, the invention includes compounds of Formula IA, wherein T is S(O)$_2$R$^1$, Z is SO$_2$, W is absent, w is 0, R$^1$ is C$_1$-C$_6$ alkyl or aryl, t is 0, R$^2$ and R$^3$ together with the atoms to which they are attached form a pyrrolidine ring, R$^{7'}$ and R$^{8'}$ together with the atoms to which they are attached form a 1,4-dioxane ring, and R$^{5'}$, R$^{6'}$, and R$^{9'}$ are each hydrogen.

In some embodiments, the invention includes compounds of Formula IA, wherein T is S(O)$_2$R$^1$, Z is SO$_2$, W is absent, w is 1, R$^1$ is C$_1$-C$_6$ alkyl or aryl, t is 0, R$^2$ and R$^3$ together with the atoms to which they are attached form a pyrrolidine ring, R$^{7'}$ and R$^{8'}$ together with the atoms to which they are attached form a 1,4-dioxane ring, and R$^{5'}$, R$^{6'}$, and R$^{9'}$ are each hydrogen.

In some embodiments, the invention includes compounds of Formula IA, wherein T is S(O)$_2$R$^1$, Z is SO$_2$, W is absent, w is 0, R$^1$ is selected from methyl, ethyl, propyl, isopropyl, butyl, isobutyl, and phenyl, t is 0, R$^2$ and R$^3$ together with the atoms to which they are attached form a pyrrolidine ring, R$^{7'}$ and R$^{8'}$ together with the atoms to which they are attached form a 1,4-dioxane ring, and R$^{5'}$, R$^{6'}$, and R$^{9'}$ are each hydrogen.

In some embodiments, the invention includes compounds of Formula IA, wherein T is S(O)$_2$R$^1$, Z is SO$_2$, W is absent, w is 1, R$^1$ is selected from methyl, ethyl, propyl, isopropyl, butyl, isobutyl, and phenyl, t is 0, R$^2$ and R$^3$ together with the atoms to which they are attached form a pyrrolidine ring, R$^{7'}$ and R$^{8'}$ together with the atoms to which they are attached form a 1,4-dioxane ring, and R$^{5'}$, R$^{6'}$, and R$^{9'}$ are each hydrogen.

Compounds of Formulae IB, IC, and ID are subsets of compounds of Formulae I and IA. Features described herein for compounds of Formula I and IA apply equally to compounds of Formulae IB, IC, and ID. Compounds of Formula IIB, IIC, IID, and TIE are subsets of compounds of Formulae II and IIA. Features described herein for compounds of Formulae II and IIA apply equally to compounds of Formula IIB, IIC, IID, and IIE.

Embodiments of the invention include compounds in Tables 1 and 2:

TABLE 1

| Compound No. | Structure |
| --- | --- |
| 2A | ![structure] |
| 3A | ![structure] |
| 4A | ![structure] |
| 5A | ![structure] |
| 22A | ![structure] |
| 23A | ![structure] |
| 6A | ![structure] |

TABLE 1-continued
| Compound No. | Structure |
|---|---|
| 7A | 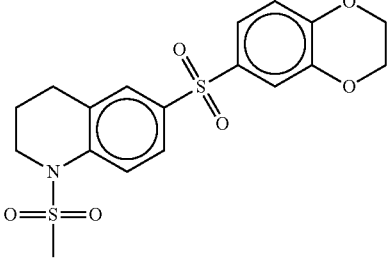 |
| 8A | 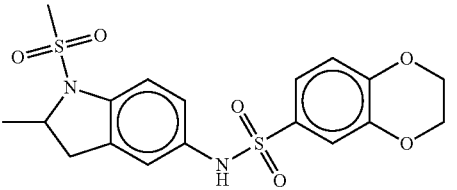 |
| 9A | 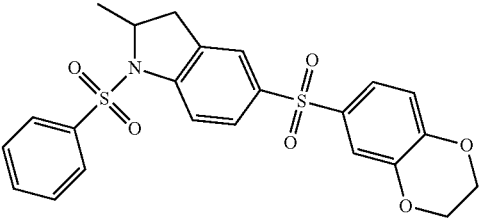 [SMILES: CC1Cc2cc(S(=O)(=O)c3ccc4c(c3)OCCO4)ccc2N1S(=O)(=O)c1ccccc1] |
| 24A | 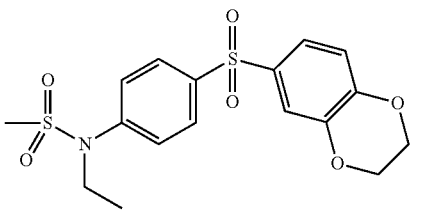 [SMILES: CCN(c1ccc(S(=O)(=O)c2ccc3c(c2)OCCO3)cc1)S(C)(=O)=O] |
| 10A | 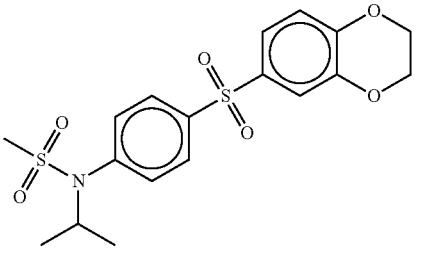 |
| 11A | 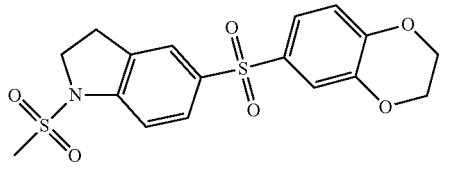 [SMILES: CS(=O)(=O)N1CCc2cc(S(=O)(=O)c3ccc4c(c3)OCCO4)ccc21] |
| 12A | 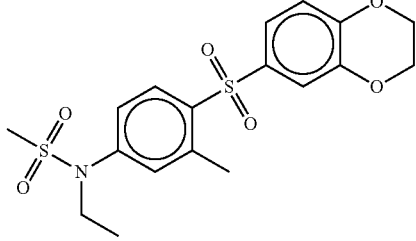 |
| 13A | 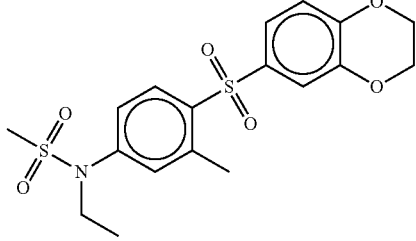 |
| 14A | 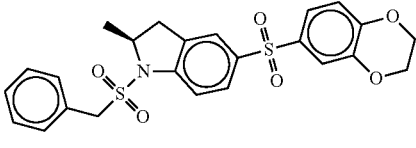 |
| 15A | 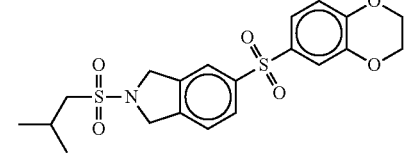 |
| 16A | 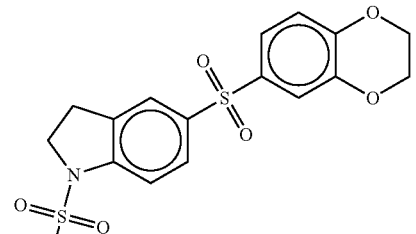 |
| 17A | 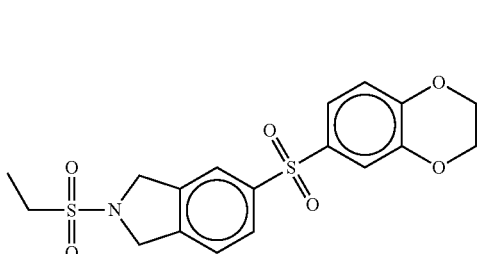 |

TABLE 1-continued

| Compound No. | Structure |
|---|---|
| 18A | 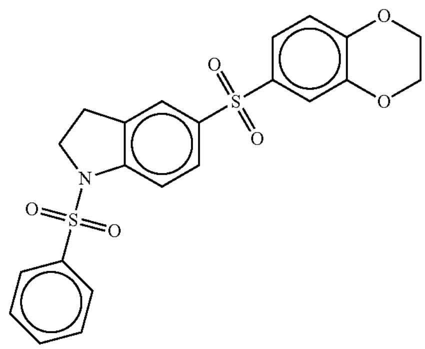 |
| 19A | 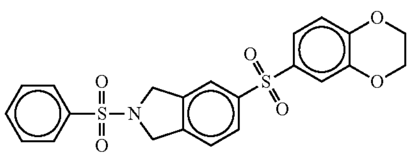 |
| 20A | 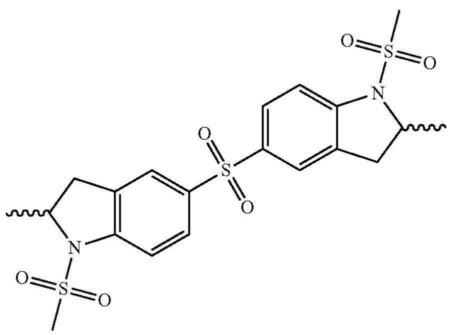 |
| 25A | 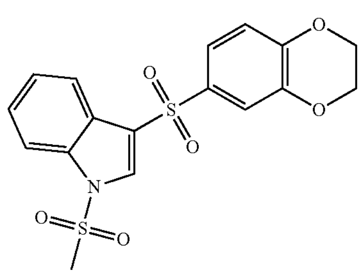 [SMILES: CS(=O)(=O)n1cc(S(=O)(=O)c2ccc3c(c2)OCCO3)c2ccccc21] |
| 21A | 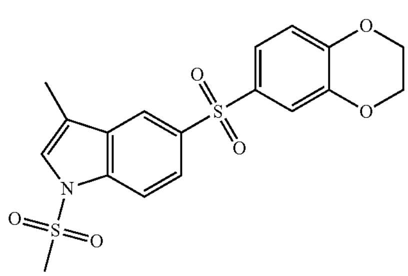 [SMILES: Cc1cn(S(C)(=O)=O)c2ccc(S(=O)(=O)c3ccc4c(c3)OCCO4)cc12] |
| 26A | |
| 27A | |
| 28A | |
| 29A | |

TABLE 1-continued
| Compound No. | Structure |
|---|---|
| 30A | 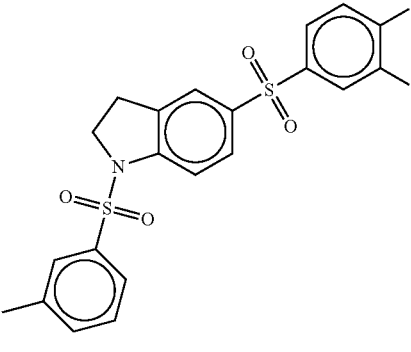 |
| 31A | 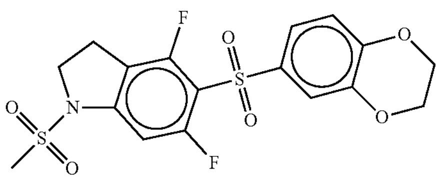 |
| 32A | 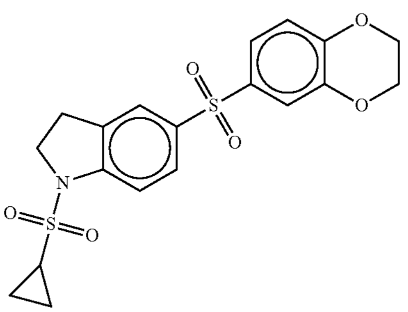 |
| 33A | 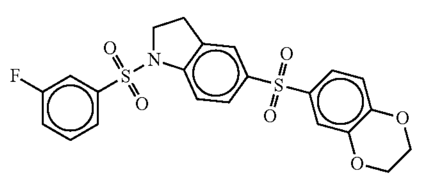 |
| 53A | 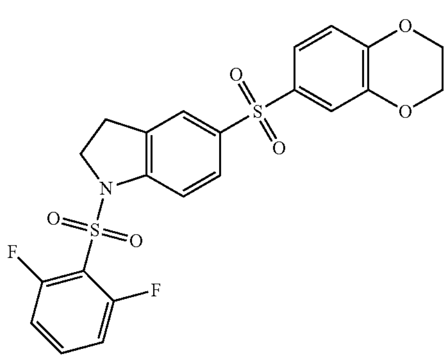 [SMILES: O=S(=O)(c1ccc2c(c1)CCN2S(=O)(=O)c1c(F)cccc1F)c1ccc2c(c1)OCCO2] |
| 54A | 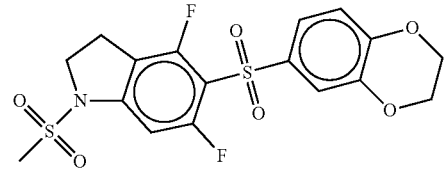 |
| 55A | 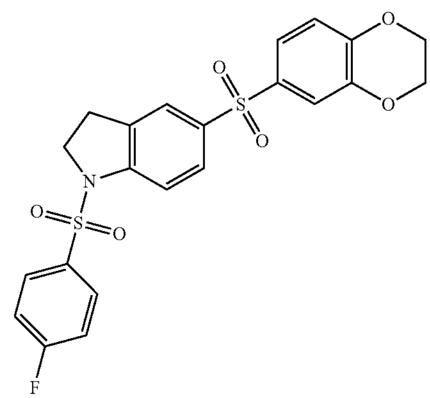 [SMILES: O=S(=O)(c1ccc2c(c1)CCN2S(=O)(=O)c1ccc(F)cc1)c1ccc2c(c1)OCCO2] |
| 56A | 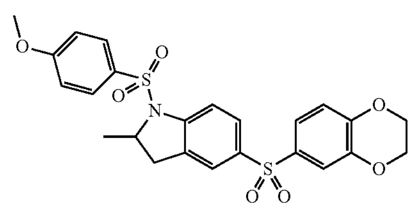 [SMILES: COc1ccc(S(=O)(=O)N2c3ccc(S(=O)(=O)c4ccc5c(c4)OCCO5)cc3CC2C)cc1] |
TABLE 2
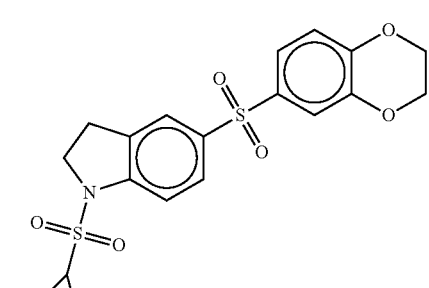
34A
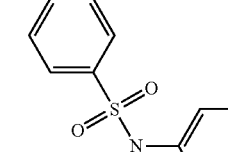
35A TABLE 2-continued
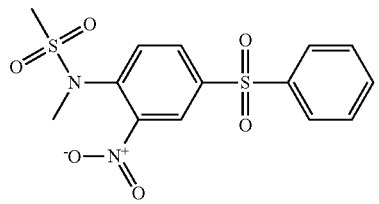
36A
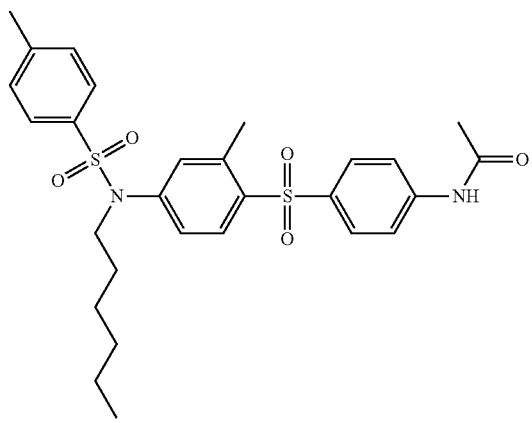 [SMILES: CCCCCCN(c1ccc(S(=O)(=O)c2ccc(NC(C)=O)cc2)c(C)c1)S(=O)(=O)c1ccc(C)cc1]
37A
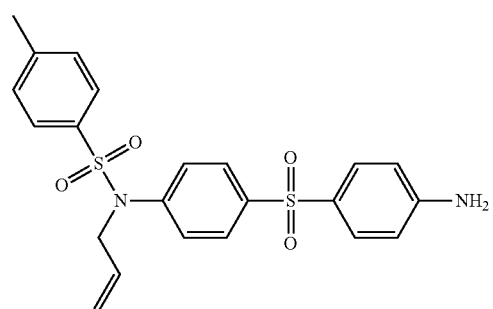 [SMILES: C=CCN(c1ccc(S(=O)(=O)c2ccc(N)cc2)cc1)S(=O)(=O)c1ccc(C)cc1]
38A
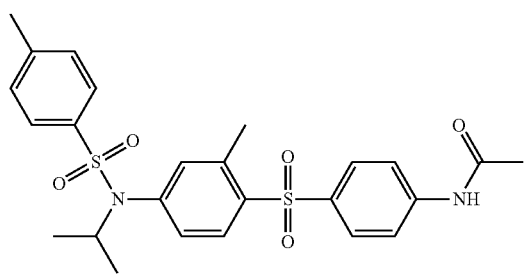 [SMILES: CC(=O)Nc1ccc(S(=O)(=O)c2ccc(N(C(C)C)S(=O)(=O)c3ccc(C)cc3)cc2C)cc1]
39A
TABLE 2-continued
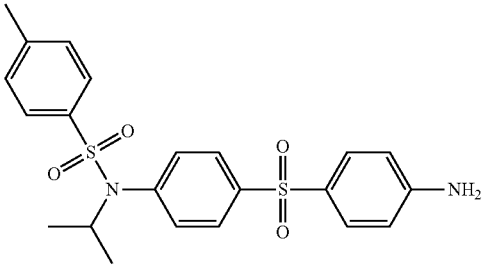 [SMILES: Cc1ccc(S(=O)(=O)N(c2ccc(S(=O)(=O)c3ccc(N)cc3)cc2)C(C)C)cc1]
40A
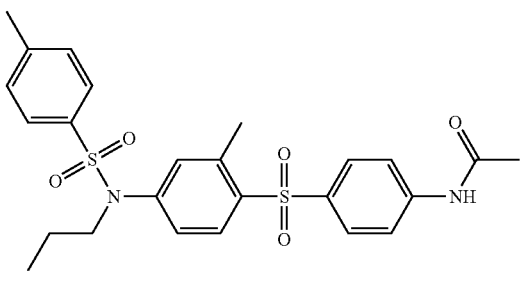 [SMILES: CCCN(c1ccc(S(=O)(=O)c2ccc(NC(C)=O)cc2)c(C)c1)S(=O)(=O)c1ccc(C)cc1]
41A
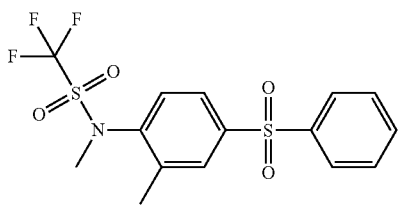 [SMILES: Cc1cc(S(=O)(=O)c2ccccc2)ccc1N(C)S(=O)(=O)C(F)(F)F]
42A
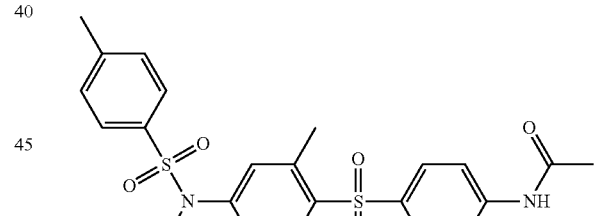
43A
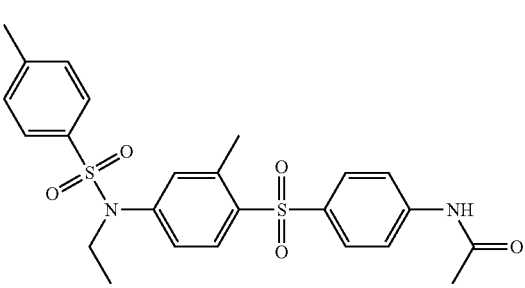 [SMILES: CCN(c1ccc(S(=O)(=O)c2ccc(NC(C)=O)cc2)c(C)c1)S(=O)(=O)c1ccc(C)cc1]
44A TABLE 2-continued

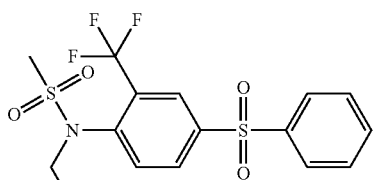

45A

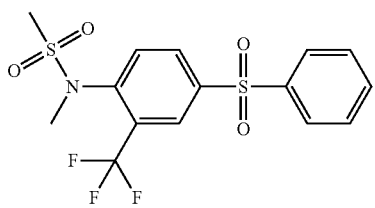 [SMILES: CN(c1ccc(S(=O)(=O)c2ccccc2)cc1C(F)(F)F)S(C)(=O)=O]

46A

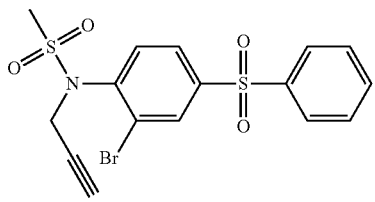 [SMILES: C#CCN(c1ccc(S(=O)(=O)c2ccccc2)cc1Br)S(C)(=O)=O]

47A

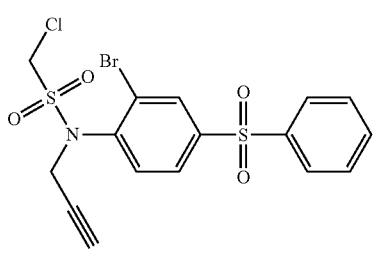

48A

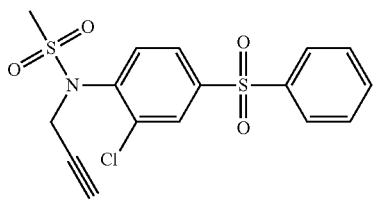 [SMILES: C#CCN(c1ccc(S(=O)(=O)c2ccccc2)cc1Cl)S(C)(=O)=O]

49A

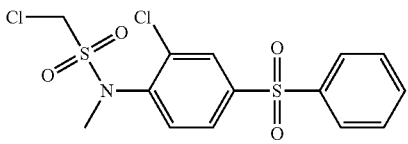

50A

TABLE 2-continued

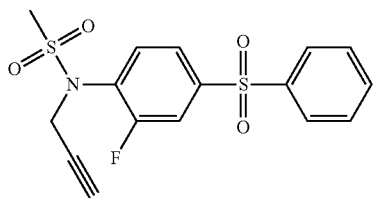 [SMILES: C#CCN(c1ccc(S(=O)(=O)c2ccccc2)cc1F)S(C)(=O)=O]

51A

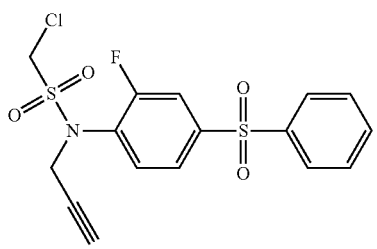 [SMILES: C#CCN(c1ccc(S(=O)(=O)c2ccccc2)cc1F)S(=O)(=O)CCl]

52A

Embodiments of the invention include a solvate of a compound according to any one of Formulae of the invention. Embodiments of the invention include a hydrate of a compound according to any one of the Formulae of the invention. Embodiments of the invention include an acid addition salt (e.g., a pharmaceutically acceptable salt) of a compound according to any one of Formulae of the invention. For example, the salt is a hydrochloride salt.

Embodiments of the invention also include a composition comprising a compound according to any one of Formulae of the invention and at least one pharmaceutically acceptable excipient. Embodiments of the invention also include a pharmaceutical composition comprising a compound according to any one of Formulae of the invention and at least one pharmaceutically acceptable excipient.

The compounds of the invention may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The compounds of the invention when used in pharmaceutical or diagnostic applications may be prepared, where applicable, as a pure or an essentially pure enantiomeric form, with an enantiopurity of at least 90% enantiomeric excess (EE), preferably at least 95% EE, more preferably at least 98% EE, and most preferably at least 99% EE. Alternatively, the compounds may be prepared, where applicable, as mixture of enantiomeric forms of the compounds (e.g., as a racemic mixture or as a mixture of enantiomers with a ratio of 60:40, 70:30, 80:20 or 90:10 between two enantiomeric forms). Enantiomeric excess values provide a quantitative measure of the excess of the percentage amount of a major isomer over the percentage amount of a minor isomer which is present therewith, and may be readily determined by suitable methods well-known and established in the art, as for example chiral high pressure liquid chromatography (HPLC), chiral gas chromatography (GC), nuclear magnetic resonance (NMR) using chiral shift reagents, etc.

When a compound of the invention has more than one stereoisomeric form, the pharmaceutical composition may be prepared with a pure or an essentially pure enantiomeric form of the compound, having an enantiopurity of at least 90% enantiomeric excess (EE), preferably at least 95% EE, more preferably at least 98% EE, and most preferably at least 99% EE. Alternatively, the pharmaceutical composition may be prepared as mixture of enantiomeric forms of the compounds (e.g., as a racemic mixture or as a mixture with a ratio of 60:40, 70:30, 80:20 or 90:10 between the enantiomeric forms).

In one aspect, compounds of the invention activate pyruvate kinase subtype M2 (PKM2). PKM2 is an enzyme which catalyzes the last step in glycolysis and is over expressed in cancer cells, is a key player in exerting the Warburg effect. One of the mechanisms by which PKM2 modulates cancer cell metabolism is by switching between a low activity form (monomer or dimer) and a high activity form (tetramer) of that enzyme, a process which is controlled by the varying concentration of an upstream glycolytic intermediate, FBP (Fructose 1,6-bisphosphate). These changes enable the cancer cell to manage its usage of glucose carbon backbones, whether for ATP production or for biomass generation, according to its changing demands. Recently it was shown that PKM2 is regulated by various phosphorylation, hydroxylation, or acetylation events.

In one aspect, the compounds of the invention are small molecule PKM2 modulators which disrupt the metabolic adaptation of cancer cells. Without wishing to be bound by theory, it is hypothesized that an activator, rather than an inhibitor, will redirect the internal usage of nutrients, especially of glucose, away from biomass production and ultimately cause the cells to die.

In one aspect, the present invention includes the discovery of several series of novel allosteric PKM2 activators that have been identified using structure-based technology. Further chemical optimization has resulted in potent compounds with AC50 as low as 10 nM, which have been shown to stabilize the active tetramer form of PKM2, similar to the action of FBP. Compounds of the invention have been tested in bioenergetic experiments in several cell lines, where it has been demonstrated that not only do the compounds reduce lactate production (represented by reduction of the extracellular acidification rate) the compounds also reduce the oxygen consumption rate as well. Analysis of cell cycle has shown that treatment with PKM2 activators causes the cells to arrest at the G1 phase. In outcome-based assays, compounds of the invention have been demonstrated to significantly reduced the proliferation rate of various cancer cell lines, indicating that rewiring cell metabolism with PKM2 activators indeed exerts an anti-proliferative effect. This data supports the hypothesis that continuous activation of PKM2 effectively deprives the cancer cell of building blocks necessary for the biomass production that is required to support growth and proliferation. In an in vivo colorectal cancer HT 29 cell line mouse xenograft model with a modestly active compound (IC50=0.9 uM) demonstrated, within a few days of treatment, tumor growth inhibition greater than 50% (200 and 400 mg/kg IP QD and 100 mg/kg Q2D). The compound was very safe in mouse, even at the highest exposure levels (200 mg/kg IP QD and 400 mg/kg IP QD), indicating that these efficacious doses are significantly lower than the maximum tolerated dose (MTD).

Taken together, this provides strong support for the effect of potent PKM2 small molecule activators on the cellular metabolism of cancer cells, demonstrating a statistically significant anti-cancer effect in an animal model of colorectal cancer. The favorable DMPK profile of compounds of the invention further supports their development as anti-proliferative agents, both as a single agent and in combination therapy.

In one aspect, compounds of the invention include any of the compounds listed in Tables 1 and 2 or a salt, solvate, hydrate, or prodrug thereof, wherein the compound activates PKM2 by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more.

In one aspect, embodiments of the invention include the foregoing compounds that activate PKM2 by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more.

In one aspect, embodiments of the invention are drawn to methods of activating PKM2 by contacting PKM2 with a compound of the invention or a salt, solvate, hydrate, or prodrug thereof. In some embodiments, PKM2 is activated by at least about 10%, by at least about 20%, by at least about 25%, by at least about 30%, by at least about 40%, by at least about 50%, by at least about 60%, by at least about 70%, by at least about 75%, by at least about 80%, by at least about 90%, or by about 95% or more. In some embodiments, the PKM2 activated is in a cell, e.g., a human cell.

Embodiments of the invention include methods of preventing or treating a cell proliferation-related disorder, a cancer, an inflammatory disorder, a metabolic disorder or an immune system disorder by administering to a subject in need thereof a pharmaceutical composition that includes a compound of the present invention or a salt, solvate, hydrate, or prodrug thereof, and at least one pharmaceutically acceptable excipient to a subject in need thereof.

When the pharmaceutical composition includes a compound of the invention that has more than one stereoisomeric form, the pharmaceutical composition may be prepared with a pure or an essentially pure enantiomeric form of the compound, with an enantiopurity of at least 90% enantiomeric excess (EE), preferably at least 95% EE, more preferably at least 98% EE, and most preferably at least 99% EE. Alternatively, the pharmaceutical composition may be prepared as mixture of enantiomeric forms of the compounds (e.g., as a racemic mixture or as a mixture with a ratio of 60:40, 70:30, 80:20 or 90:10 between the enantiomeric forms). The invention also includes use of a compound of the invention in the manufacture of a medicament to prevent or treat a cell proliferation-related disorder, a cancer, an inflammatory disorder, a metabolic disorder, or an immune system disorder. When the medicament includes a compound of the invention that has more than one stereoisomeric form, the medicament may be prepared with a pure or an an essentially pure enantiomeric form of the compound, with an enantiopurity of at least 90% enantiomeric excess (EE), preferably at least 95% EE, more preferably at least 98% EE, and most preferably at least 99% EE. Alternatively, the medicament may be prepared as mixture of enantiomeric forms of the compounds (e.g., as a racemic mixture or as a mixture with a ratio of 60:40, 70:30, 80:20 or 90:10 between the enantiomeric forms).

The invention relates to a method of treating or preventing a disease or disorder that is modulated by PKM2 activation, by administering a pharmaceutical composition that includes a compound of the invention or a salt, solvate, hydrate, or prodrug thereof, and at least one pharmaceutically acceptable excipient. When the pharmaceutical composition includes a compound of the invention that has more than one stereoisomeric form, the pharmaceutical composition may be prepared with a pure or an essentially pure enantiomeric form of the compound, with an enantiopurity of at least 90% enantiomeric excess (EE), preferably at least 95% EE, more preferably at least 98% EE, and most preferably at least 99% EE. Alternatively, the pharmaceutical composition may be prepared as mixture of enantiomeric forms of the compounds (e.g., as a racemic mixture or as a mixture with a ratio of 60:40, 70:30, 80:20 or 90:10 between the enantiomeric forms). For example, the disease or disorder that is modulated by PKM2 activation is cancer, pre-cancer or a hyperproliferative disorder.

One aspect of the invention includes preventing or treating an immune system disorder. One aspect includes methods of regulating system activity in a subject comprising administering a pharmaceutical composition that includes a compound of the invention. Embodiments of the invention also include the use of a compound of the invention in the manufacture of a medicament to regulate immune system activity. Examples of diseases that may be treated or prevented according to the foregoing methods include, but are not limited to, allergies, asthma, autoimmune diseases such as transplant rejection (e.g., kidney, heart, lung, liver, pancreas, skin, host versus graft reaction (HVGR), etc.), rheumatoid arthritis, and amyotrophic lateral sclerosis, multiple sclerosis, psoriasis and Sjogren' syndrome, Type II inflammatory disease such as vascular inflammation (including vasculitis, ateritis, atherosclerosis and coronary artery disease), diseases of the central nervous system such as stroke, pulmonary diseases such as bronchitis obliterous and primary and primary pulmonary hypertension, delayed or cell-mediated, Type IV hypersensitivity and solid and hematologic malignancies such as leukemias and lymphomas.

One aspect of the invention includes methods of preventing or treating an inflammatory disorder comprising administering a pharmaceutical composition that includes an effective amount of one of the compounds of any of the formulae or compounds described herein. Inflammatory disorders are characterized by inflammation. Embodiments of the invention includes inflammatory disorders may include one or more of inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystitus, irritable bowel syndrome, ulcerative colitis, glomerulonephritis, dermatomyositis, scleroderma, vasculitis, allergic disorders including asthma such as bronchial, allergic, intrinsic, extrinsic and dust asthma, particularly chronic or inveterate asthma (e.g. late asthma airways hyper-responsiveness) and bronchitis, chronic obstructive pulmonary disease (COPD), multiple sclerosis, rheumatoid arthritis, disorders of the gastrointestinal tract, including, without limitation, Coeliac disease, proctitis, eosinophilic gastro-enteritis, mastocytosis, pancreatitis, Crohn's disease, ulcerative colitis, food-related allergies which have effects remote from the gut, e.g. migraine, rhinitis and eczema. Conditions characterised by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung and idiopathic interstitial pneumonia, acute pancreatitis, chronic pancreatitis, and adult respiratory distress syndrome, and/or acute inflammatory responses (such as acute respiratory distress syndrome and ischemia/reperfusion injury).

One aspect of the invention includes methods of preventing or treating a metabolic disorder comprising administering a pharmaceutical composition that includes an effective amount of one of the compounds of any of the formulae or compounds described herein. A metabolic disorder is any disorder that involves an alteration in the normal metabolism of carbohydrates, lipids, proteins, water, and nucleic acids. Examples of metabolic disorders include type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia. Metabolic syndrome is one type of metabolic disorder. Metabolic syndrome is a combination of medical disorders that, when they occur together, increase the risk of developing cardiovascular disease and diabetes. Metabolic syndrome is also known as metabolic syndrome X, cardiometabolic syndrome, syndrome X, insulin resistance syndrome, Reaven's syndrome (named for Gerald Reaven), and CHAOS (in Australia).

In one aspect, compounds of the invention may be used as a pharmaceutical agent. The compounds may be used without limitation, for example, as anti-cancer, anti-proliferative, anti-inflammatory and/or immunosuppressive agents, for treating humans and/or animals, such as for treating humans and/or other mammals.

In some embodiments, the administration of the compound of the invention is carried out orally, parentally, subcutaneously, intravenously, intramuscularly, intraperitoneally, by intranasal instillation, by intracavitary or intravesical instillation, topically, intraarterially, intralesionally, by metering pump, or by application to mucous membranes. In some embodiments, the compound of the invention is administered with a pharmaceutically acceptable carrier.

In certain embodiments, the cell proliferation disorder includes any type of cancer including solid tumors and non-solid tumors. In specific embodiments the solid tumors are selected from tumors in the CNS (central nervous system), liver cancer, colorectal carcinoma, breast cancer, gastric cancer, pancreatic cancer, bladder carcinoma, cervical carcinoma, head and neck tumors, vulvar cancer and dermatological neoplasms including melanoma, squamous cell carcinoma and basal cell carcinomas. In other embodiments, non-solid tumors include lymphoproliferative disorders including leukemias and lymphomas. In other embodiments, the disorder is metastatic disease.

The compounds of the invention also may be used in the treatment of a cancer or cell proliferation disorder in a combination therapy with one or more of anti-cancer treatments such as surgery, radiation therapy, immunotherapy and/or one or more anti-cancer agents selected from the group consisting of anti-proliferative agents, other agents that modulate the metabolism of cancer cells, cytotoxic agents, cytostatic agents, and chemotherapeutic agents and salts and derivatives thereof. According to certain embodiments, the compounds of the invention may be used in the treatment of a cancer or cell proliferation disorder in combination therapy with any one of the drugs selected from a group consisting of an alkaloid, an alkylating agent, an antitumor antibiotic, an antimetabolite, a Bcr-Abl tyrosine kinase inhibitor, a nucleoside analogue, a multidrug resistance reversing agent, a DNA binding agent, microtubule binding drug, a toxin and a DNA antagonist. Those of skill in the art will recognize the chemotherapeutic agents classified into one or more particular classes of chemotherapeutic agents described above.

When used in combination with additional anti-proliferation agents, the compounds of the invention may enhance (e.g., synergize) the activity of these agents. Further, such synergism would permit the compounds of the invention, additional anti-proliferation agents, or both to be administered at lower dosages, and/or may significantly enhance the anti-proliferation properties of the compounds at any given dose.

Definitions

For convenience, certain terms used in the specification, examples and appended claims are collected here.

A compound "activates PKM2" if the compound stimulates the enzymatic activity by PKM2 of reaction 1 by at least 10% relative to the activity of PKM2 under the same conditions but lacking only the presence of the compound.

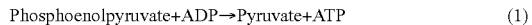

$$\text{Phosphoenolpyruvate} + \text{ADP} \rightarrow \text{Pyruvate} + \text{ATP} \qquad (1)$$

The activity of PKM2 may be measured by any reproducible means. The activity of PKM2 may be measured in vitro or in vivo.

"Treating", includes any effect, e.g., lessening, reducing, modulating, or eliminating, that results in the improvement of the condition, disease, disorder, etc. "Treating" or "treatment" of a disease state includes: (1) inhibiting the disease state, i.e., arresting the development of the disease state or its clinical symptoms or (2) relieving the disease state, i.e., causing temporary or permanent regression of the disease state or its clinical symptoms.

"Preventing" means causing the clinical symptoms of the disease state not to develop, i.e., inhibiting the onset of disease, in a subject that may be exposed to or predisposed to the disease state, but does not yet experience or display symptoms of the disease state.

"Disease state" means any disease, disorder, condition, symptom, or indication.

In some embodiments, the cell proliferation disorder is cancer. As used herein, the term "cancer" includes solid tumors, such as lung, breast, colon, ovarian, brain, liver, pancreas, prostate, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

An "effective amount" of a compound is the quantity which, when administered to a subject having a disease or disorder, results in regression of the disease or disorder in the subject. Thus, for example, for a cell proliferation disorder an effective amount of a compound of the invention is the quantity which, when administered to a subject having a cell proliferation disorder, results in regression of cell growth in the subject. The amount of the compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

"A therapeutically effective amount" means the amount of a compound that, when administered to a mammal, e.g., a human, for treating a disease, is sufficient to effect such treatment for the disease. The "therapeutically effective amount" will vary depending on the compound, the disease and its severity and the age, weight, etc., of the mammal to be treated.

A therapeutically effective amount of one or more of the compounds of the invention can be formulated with a pharmaceutically acceptable carrier for administration to a human or an animal. Accordingly, the compounds or the formulations can be administered, for example, via oral, parenteral, or topical routes, to provide an effective amount of the compound. In alternative embodiments, the compounds prepared in accordance with the invention can be used to coat or impregnate a medical device, e.g., a stent.

The term "prophylactically effective amount" means an effective amount of a compound or compounds of the invention that is administered to prevent or reduce the risk of a disease state.

"Pharmacological effect" as used herein encompasses effects produced in the subject that achieve the intended purpose of a therapy.

With respect to the compounds useful in the invention, the following terms can be applicable:

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

The invention also comprehends isotopically-labeled compounds, which are identical to those recited in the formulae of the invention, but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, fluorine, such as $^3$H, $^{11}$C, $^{14}$C, $^2$H and $^{18}$F.

Compounds of the invention and salts, hydrates, solvates or prodrugs of said compounds that contain the aforementioned isotopes and/or other isotopes of other atoms are within the scope of the invention. Isotopically-labeled compounds of the invention, for example those into which radioactive isotopes such as $^3$H, $^{14}$C are incorporated, are useful in drug and/or substrate tissue distribution assays. Tritiated, i.e., 3H, and carbon-14, i.e., $^{14}$C, isotopes are particularly preferred for their ease of preparation and detectability. $^{11}$C and $^{18}$F isotopes are particularly useful in PET (positron emission tomography). PET is useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances, isotopically labeled compounds of this invention can generally be prepared by carrying out the procedures disclosed in the Schemes and/or in the Examples below, by substituting a readily available isotopically labeled reagent for a non-isotopically labeled reagent. In one embodiment, the compounds of the invention, salts, hydrates, solvates, or prodrugs thereof are not isotopically labelled.

The compounds described herein may have asymmetric centers. Compounds of the invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

When any variable (e.g., $R^4$) occurs more than one time in any constituent or formula for a compound, its definition at each occurrence is independent of its definition at every other occurrence. Thus, for example, if a group is shown to be substituted with 0-3 $R^4$ moieties, then the group may optionally be substituted with up to three $R^4$ moieties and $R^4$ at each occurrence is selected independently from the definition of $R^4$. Also, combinations of substituents and/or variables are permissible, but only if such combinations result in stable compounds.

When an atom or chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched and straight-chain saturated aliphatic hydrocarbon groups having the specified number of carbon atoms. For example, $C_{1-6}$ alkyl is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, s-pentyl, and n-hexyl. In certain embodiments, a straight chain or branched chain alkyl has six or fewer carbon atoms in its backbone (e.g., $C_1$-$C_6$ for straight chain, $C_3$-$C_6$ for branched chain), and in another embodiment, a straight chain or branched chain alkyl has four or fewer carbon atoms. Likewise, cycloalkyls have from three to eight carbon atoms in their ring structure, and in other embodiments, cycloalkyls have five or six carbons in the ring structure.

Unless the number of carbons is otherwise specified, "lower alkyl" includes an alkyl group, as defined above, but having from one to ten, or in other embodiments from one to six, carbon atoms in its backbone structure. "Lower alkenyl" and "lower alkynyl" have chain lengths of, for example, 2-6 carbon atoms.

The term "substituted alkyls" refers to alkyl moieties having substituents replacing hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aryl or heteroaryl moiety. Cycloalkyls can be further substituted, e.g., with the substituents described above. An "alkylaryl" or an "aralkyl" moiety is an alkyl substituted with an aryl (e.g., phenylmethyl (benzyl)).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has six or fewer carbon atoms in its backbone (e.g., $C_2$-$C_6$ for straight chain, $C_3$-$C_6$ for branched chain). Likewise, cycloalkenyl groups may have from three to eight carbon atoms in their ring structure, and in some embodiments, cycloalkenyl groups have five or six carbons in the ring structure. The term "$C_2$-$C_6$" includes alkenyl groups containing two to six carbon atoms. The term "$C_3$-$C_6$" includes alkenyl groups containing three to six carbon atoms.

The term "substituted alkenyls" refers to alkenyl moieties having substituents replacing hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, aryl or heteroaryl moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "substituted alkynyls" refers to alkynyl moieties having substituents replacing hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, aryl, or heteroaryl moiety.

"Aryl" includes phenyl and napthyl. Aryl rings can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, aryl, or heteroaryl moiety.

As used herein, "halo" or "halogen" refers to fluoro, chloro, bromo, and iodo. The term "perhalogenated" generally refers to a moiety wherein all hydrogens are replaced by halogen atoms.

The term "haloalkyl" refers to alkylmoieties having a halogen atom replacing a hydrogen atom on one or more carbons of the hydrocarbon backbone. $C_1$-$C_6$ haloalkyl is intended to include a straight chain or branched alkyl having six or fewer carbon atoms in its backbone and a halogen atom replacing a hydrogen atom on one or more carbonds of the hydrocarbon backbone.

"Counterion" is used to represent a small, negatively charged species such as chloride, bromide, hydroxide, acetate, and sulfate.

The term "non-hydrogen substituent" refers to substituents other than hydrogen. Non-limiting examples include alkyl groups, alkoxy groups, halogen groups, hydroxyl groups, aryl groups, etc.

As used herein, "carbocycle" or "carbocyclic ring" is intended to mean any stable monocyclic, bicyclic, or tricyclic ring having the specified number of carbons, any of which may be saturated, unsaturated, or aromatic. For example a $C_{3-14}$ carbocycle is intended to mean a mono-, bi-, or tricyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cyclohexenyl, cycloheptyl, cycloheptenyl, adamantyl, cyclooctyl, cyclooctenyl, cyclooctadienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane, and [2.2.2]bicyclooctane. A bridged ring occurs when one or more carbon atoms link two non-adjacent carbon atoms. In some embodiments, bridge rings are one or two carbon atoms. It is noted that a bridge always converts a monocyclic ring into a tricyclic ring. When a ring is bridged, the substituents recited for the ring may also be present on the bridge. Fused (e.g., naphthyl and tetrahydronaphthyl) and spiro rings are also included.

As used herein, the term "heterocycle", "heterocyclic" is intended to mean any stable monocyclic, bicyclic, or tricyclic ring which is saturated or partially unsaturated and comprises carbon atoms and one or more ring heteroatoms, e.g., 1 or 1-2 or 1-3 or 1-4 or 1-5 or 1-6 heteroatoms, independently selected from the group consisting of nitrogen, oxygen, and sulfur. A bicyclic or tricyclic heterocycle may have one or more heteroatoms located in one ring, or the heteroatoms may be located in more than one ring. The nitrogen and sulfur heteroatoms may optionally be oxidized (i.e., N→O and S(O)$_p$, where p=1 or 2). When a nitrogen atom is included in the ring it is either N or NH, depending on whether or not it is attached to a double bond in the ring (i.e., a hydrogen is present if needed to maintain the tri-valency of the nitrogen atom). The nitrogen atom may be substituted or unsubstituted (i.e., N or NR wherein R is H or another substituent, as defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. In some embodiments, when the total number of S and O atoms in the heterocycle exceeds 1, then these heteroatoms are not adjacent to one another. Bridged rings are also included in the definition of heterocycle. A bridged ring occurs when one or more atoms (i.e., C, O, N, or S) link two non-adjacent carbon or nitrogen atoms. Bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. Spiro and fused rings are also included.

As used herein, the term "heterocycloalkyl" is intended to mean any stable monocyclic, bicyclic, or tricyclic ring which is saturated and comprises carbon atoms and one or more ring heteroatoms e.g., 1 or 1-2 or 1-3 or 1-4 or 1-5 of 1-6 heteroatoms, independently selected from the group consisting of nitrogen, oxygen, and sulfur. One example of a heterocycloalkyl is a 1,4 dioxane ring.

As used herein, the term "aromatic heterocycle" or "heteroaryl" is intended to mean a stable 5, 6, or 7-membered monocyclic or bicyclic aromatic heterocyclic ring or 7, 8, 9, 10, 11, or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen, and sulfur. In the case of bicyclic heterocyclic aromatic rings, only one of the two rings needs to be aromatic i.e., the rings may be partially aromatic (e.g., 2,3-dihydroindole), though both rings may be aromatic (e.g., quinoline). The second ring can also be fused or bridged as defined above for heterocycles. The nitrogen atom may be substituted or unsubstituted (i.e., N or NR wherein R is H or another substituent, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3, 4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Acyl" includes compounds and moieties that contain the acyl radical ($CH_3CO—$). "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, aryl or heteroaryl moiety.

"Acylamino" includes moieties wherein an acyl moiety is bonded to an amino group. For example, the term includes alkylcarbonylamino, arylcarbonylamino, carbamoyl and ureido groups.

"Aroyl" includes compounds and moieties with an aryl or heteroaryl moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms, e.g., oxygen, nitrogen or sulfur atoms.

The term "alkoxy" or "alkoxyl" includes substituted and unsubstituted alkyl, alkenyl, and alkynyl groups covalently linked to an oxygen atom. $C_1$-$C_6$ alkoxy refers to moieties having six of few carbon atoms in the hydrocarbon backbone. Examples of alkoxy groups (or alkoxyl radicals) include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, aryl, or heteroaryl moieties. Examples of halogen substituted alkoxy groups include, but are not limited to, fluoromethoxy, difluoromethoxy, trifluoromethoxy, chloromethoxy, dichloromethoxy, and trichloromethoxy.

The term "thiocarbonyl" or "thiocarboxy" includes compounds and moieties which contain a carbon connected with a double bond to a sulfur atom.

The term "ether" or "alkoxy" includes compounds or moieties which contain an oxygen atom bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and "alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

"Polycyclyl" or "polycyclic radical" refers to two or more cyclic rings (e.g., cycloalkyls, cycloalkenyls, cycloalkynyls, aryls and/or heterocyclyls) in which two or more carbons are common to two adjoining rings. Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, aryl, or heteroaryl moiety.

An "anionic group," as used herein, refers to a group that is negatively charged at physiological pH. Anionic groups include carboxylate, sulfate, sulfonate, sulfonate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23). In some embodiments, an anionic group is a carboxylate.

In the present specification, the structural formula of the compound represents a certain isomer for convenience in some cases, but the invention includes all isomers such as geometrical isomer, optical isomer based on an asymmetrical carbon, stereoisomer, tautomer and the like which occur structurally and an isomer mixture and is not limited to the description of the formula for convenience, and may be any one isomer or a mixture. Therefore, an asymmetrical carbon atom may be present in the molecule and an optically active compound and a racemic compound may be present in the present compound, but the invention is not limited to them and includes any one. In addition, a crystal polymorphism may be present but is not limiting, but any crystal form may be single or a crystal form mixture, or an anhydride or hydrate. Further, so-called metabolite which is produced by degradation of the present compound in vivo is included in the scope of the invention.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Calm, Ingold and Prelog. (Calm et al, *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, J., *Chem. Educ.* 1964, 41, 116).

"Geometric Isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorph" or "polymorph" or "crystal form" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Tautomer" refers to compounds whose structures differ markedly in arrangement of atoms, but which exist in easy and rapid equilibrium. It is to be understood that the compounds of the invention may be depicted as different tautomers. It should also be understood that when compounds have tautomeric forms, all tautomeric forms are intended to be within the scope of the invention, and the naming of the compounds does not exclude any tautomer form.

Some compounds of the invention can exist in tautomeric forms, which are also intended to be encompassed within the scope of the invention.

The compounds, salts and prodrugs of the invention can exist in several tautomeric forms, including the enol and imine form, and the keto and enamine form and geometric isomers and mixtures thereof. All such tautomeric forms are included within the scope of the invention. Tautomers exist as mixtures of a tautomeric set in solution. In solid form, usually one tautomer predominates. Even though one tautomer may be described, the invention includes all tautomers of the present compounds.

A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism, is exhibited by glucose. It arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

Common tautomeric pairs are: ketone—enol, amide—nitrile, lactam—lactim, amide—imidic acid tautomerism in heterocyclic rings (e.g. in the nucleobases guanine, thymine, and cytosine), amine—enamine and enamine—enamine.

It will be noted that the structure of some of the compounds of the invention include asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate. The compounds of this invention may exist in stereoisomeric form, therefore can be produced as individual stereoisomers or as mixtures.

As used herein, the term "analog" refers to a compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative", refers to compounds that have a common core structure, and are substituted with various groups as described herein.

A "pharmaceutical composition" is a formulation containing the compounds in a form suitable for administration to a subject. In some embodiments, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salt, hydrate, solvate, or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. In some embodiments, the route of administration is oral. Dosage forms for the topical or transdermal administration of a compound of this invention include powders, sprays, ointments, pastes, creams, lotions, gels, solutions, patches and inhalants. In some embodiments, the active compound is mixed under sterile conditions with a pharmaceutically acceptable carrier, and with any preservatives, buffers, or propellants that are required.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In some embodiments, the subject is human.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used herein includes both one and more than one such excipient.

The compounds of the invention are capable of further forming salts. All of these forms are also contemplated within the scope of the invention.

"Pharmaceutically acceptable salt" of a compound means a salt that is pharmaceutically acceptable and that possesses the desired pharmacological activity of the parent compound.

As used herein, "pharmaceutically acceptable salts" refer to derivatives of the compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The pharmaceutically acceptable salts of the invention can be synthesized from a parent compound that contains a basic or acidic moiety by conventional chemical methods. Generally, such salts can be prepared by the reaction of the free acid or base forms of the parent compounds with a stoichiometric amount of the appropriate base or acid in water or in an organic solvent, or in a mixture of the two; non-aqueous media like ether, ethyl acetate, ethanol, isopropanol, or acetonitrile can be used. Lists of suitable salts are found in *Remington's Pharmaceutical Sciences,* 18th ed. (Mack Publishing Company, 1990). For example, salts can include, but are not limited to, the hydrochloride and acetate salts of the aliphatic amine-containing, hydroxylamine-containing, and imine-containing compounds of the present invention.

Compounds of the invention can also be prepared as esters, for example pharmaceutically acceptable esters. For example a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

Compounds of the invention can also be prepared as prodrugs, for example pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs may be prepared by modifying functional groups present in the compound in such a way that the modifications are cleaved, either in routine manipulation or in vivo, to the parent compound. Prodrugs include compounds of the invention wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p1-92, Elesevier, New York-Oxford (1985).

"Stable compound" and "stable structure" are meant to indicate a compound that is sufficiently robust to survive isolation to a useful degree of purity from a reaction mixture, and formulation into an efficacious therapeutic agent.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

The p invention provides methods for the treatment of a cell proliferative disorder in a subject in need thereof by administering to a subject in need of such treatment, a therapeutically effective amount of a compound of the invention, or a pharmaceutically acceptable salt, prodrug, metabolite, polymorph or solvate thereof. The cell proliferative disorder can be cancer or a precancerous condition. The invention further provides the use of a compound of the invention, or a pharmaceutically acceptable salt, prodrug, metabolite, polymorph or solvate thereof, for the preparation of a medicament useful for the treatment of a cell proliferative disorder.

The invention also provides methods of protecting against a cell proliferative disorder in a subject in need thereof by administering a therapeutically effective amount of compound of the invention, or a pharmaceutically acceptable salt, prodrug, metabolite, polymorph or solvate thereof, to a subject in need of such treatment. The cell proliferative disorder can be cancer or a precancerous condition. The invention also provides the use of compound of the invention, or a pharmaceutically acceptable salt, prodrug, metabolite, polymorph or solvate thereof, for the preparation of a medicament useful for the prevention of a cell proliferative disorder.

As used herein, a "subject in need thereof" is a subject having a cell proliferative disorder, or a subject having an increased risk of developing a cell proliferative disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. In some embodiments, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present invention may be used to treat a cancer selected from the group consisting of a hematologic cancer of the present invention or a hematologic cell proliferative disorder of the present invention. A hematologic cancer of the invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Preferably, compositions of the present invention may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma", bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. Preferably, compositions of the present invention may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

The cell proliferative disorder of the breast can be breast cancer. Preferably, compositions of the present invention may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

In some embodiments, a compound of the invention, or a pharmaceutically acceptable salt, prodrug, hydate or solvate thereof, may be used to treat breast cancer. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed as HER2-negative or HER2-positive. HER2-typing of a breast cancer may be performed by any reproducible means. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich or PR-poor. A breast cancer that is to be treated can be typed as PR-negative or PR-positive. PR-typing of a breast cancer may be performed by any reproducible means. A breast cancer that is to be treated can be typed as receptor positive or receptor negative. A breast cancer that is to be treated can have multiple receptors each independently typed as receptor positive or receptor negative. For example, a breast cancer that can be treated can be "a triple negative breast cancer" (i.e., typed as ER-negative, PR-negative, and HER2-negative). A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the invention, or a pharmaceutically acceptable salt, prodrug, hydrate, or solvate thereof, may be used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A. cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the invention, or a pharmaceutically acceptable salt, prodrug, hydrate, or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the invention, or a pharmaceutically acceptable salt, prodrug, hydrate, or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the invention, or a pharmaceutically acceptable salt, prodrug, solvate, or hydrate thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the invention, or a pharmaceutically acceptable salt, hydrate, or solvate thereof, is more effective than combination therapy in inducing a desired biological effect.

As used herein, "treating" or "treat" describes the management and care of a patient for the purpose of combating a disease, condition, or disorder and includes the administration of a compound of the invention, or a pharmaceutically acceptable salt, prodrug, hydrate, or solvate thereof, to alleviate the symptoms or complications of a disease, condition or disorder, or to eliminate the disease, condition or disorder.

A compound of the invention, or a pharmaceutically acceptable salt, prodrug, hydrate, or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin (see next section), some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant invention.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. In some embodiments, the mortality rate is decreased by more than 2%; by more than 5%; by more than 10%; and by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. In some embodiments, after treatment, tumor growth rate is reduced by at least 5% relative to number prior to treatment; tumor growth rate is reduced by at least 10%; reduced by at least 20%; reduced by at least 30%; reduced by at least 40%; reduced by at least 50%; reduced by at least 50%; and reduced by at least 75%. Tumor growth rate may be measured by any reproducible means of measurement. Tumor growth rate can be measured according to a change in tumor diameter per unit time.

Treating cancer can result in a decrease in tumor regrowth. In some embodiments, after treatment, tumor regrowth is less than 5%; tumor regrowth is less than 10%; less than 20%; less than 30%; less than 40%; less than 50%; less than 50%; and less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; by at least 10%; by at least 20%; by at least 30%; by at least 40%; by at least 50%; by at least 50%; and by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. In some embodiments, after treatment, the proportion of proliferating cells is reduced by at least 5%; by at least 10%; by at least 20%; by at least 30%; by at least 40%; by at least 50%; by at least 50%; and by at least 75%. The proportion of proliferating cells may be measured by any reproducible means of measurement. In some embodiments, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. In some embodiments, after treatment, size of an area or zone of cellular proliferation is reduced by at least 5% relative to its size prior to treatment; more preferably, reduced by at least 10%; reduced by at least 20%; reduced by at least 30%; reduced by at least 40%; reduced by at least 50%; reduced by at least 50%; and reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. In some embodiments, after treatment, the number of cells having an abnormal morphology is reduced by at least 5% relative to its size prior to treatment; reduced by at least 10%; reduced by at least 20%; reduced by at least 30%; reduced by at least 40%; reduced by at least 50%; reduced by at least 50%; and reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. In some embodiments, a compound of the invention, or a pharmaceutically acceptable salt, prodrug, hydrate, or solvate thereof, acts selectively on a cancer or precancerous cell but not on a normal cell. In some embodiments, a compound of the invention, or a pharmaceutically acceptable salt, prodrug, hydrate, or solvate thereof, acts selectively to modulate one molecular target (e.g., PKM2) but does not significantly modulate another molecular target (e.g., PKM1). The invention also provides a method for selectively inhibiting the activity of an enzyme, such as a kinase. In some embodiments, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; greater than fifty times; greater than 100 times; and greater than 1000 times more frequently in population A as compared to population B. For example, cell death would be said to occur selectively in cancer cells if it occurred greater than twice as frequently in cancer cells as compared to normal cells.

A compound of the invention, or a pharmaceutically acceptable salt, prodrug, hydrate, or solvate thereof, can modulate the activity of a molecular target (e.g., PKM2). Modulating refers to stimulating or inhibiting an activity of a molecular target. In some embodiments, a compound of the invention, or a pharmaceutically acceptable salt, prodrug, hydrate, or solvate thereof, modulates the activity of a molecular target if it stimulates or inhibits the activity of the molecular target by at least 10% relative to the activity of the molecular target under the same conditions but lacking only the presence of said compound. In some embodiments, a compound of the invention, or a pharmaceutically acceptable salt, prodrug, hydrate, or solvate thereof, modulates the activity of a molecular target if it stimulates or inhibits the activity of the molecular target by at least 2-fold, at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro or in vivo by an enzymatic activity assay.

A compound of the invention, or a pharmaceutically acceptable salt, prodrug, hydrate, or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a kinase isozyme alpha in comparison to a kinase isozyme beta).

A change in enzymatic activity caused by a compound of the invention, or a pharmaceutically acceptable salt, prodrug, hydrate, or solvate thereof, can be measured in the disclosed assays. The change in enzymatic activity can be characterized by the change in the extent of phosphorylation of certain substrates. As used herein, "phosphorylation" refers to the addition of phosphate groups to a substrate, including proteins and organic molecules; and, plays an important role in regulating the biological activities of proteins. Preferably, the phosphorylation assayed and measured involves the addition of phosphate groups to tyrosine residues. The substrate can be a peptide or protein.

In some assays, immunological reagents, e.g., antibodies and antigens, are employed. Fluorescence can be utilized in the measurement of enzymatic activity in some assays. As used herein, "fluorescence" refers to a process through which a molecule emits a photon as a result of absorbing an incoming photon of higher energy by the same molecule. Specific methods for assessing the biological activity of the disclosed compounds are described in the examples.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

Treating cancer or a cell proliferative disorder can result in cell death, and cell death results in a decrease of at least 10% in number of cells in a population. In some embodiments, cell death means a decrease of at least 20%; a decrease of at least 30%; a decrease of at least 40%; a decrease of at least 50%; a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

In some embodiments, an effective amount of a compound of the invention, or a pharmaceutically acceptable salt, prodrug, hydrate, or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the invention, or a pharmaceutically acceptable salt, prodrug, hydrate, or solvate thereof, can induce or activate cell death selectively in cancer cells. Administering to a subject in need thereof a compound of the invention, or a pharmaceutically acceptable salt, prodrug, hydrate, or solvate thereof, can induce or activate cell death selectively in cancer cells. Contacting a cell with a compound of the invention, or a pharmaceutically acceptable salt, prodrug, hydrate, or solvate thereof, can induce cell death selectively in one or more cells affected by a cell proliferative disorder. In some embodiments, administering to a subject in need thereof a compound of the invention, or a pharmaceutically acceptable salt, prodrug, hydrate, or solvate thereof, induces cell death selectively in one or more cells affected by a cell proliferative disorder.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the invention.

"Combination therapy" (or "co-therapy") includes the administration of a compound of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agent(s) as described above in further combination with other biologically active ingredients and/or non-drug therapies (e.g., surgery, immunotherapy or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the invention, or a pharmaceutically acceptable salt, prodrug, hydrate, or solvate thereof, may be administered in combination with a second anti-cancer agent. The second anti-cancer agent (also referred to as an anti-neoplastic agent or anti-proliferative agent) can be another agent that modulates cancer metabolism; an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemeterxed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine[131] tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexylen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur-0.4 M 5-chloro-2,4-dihydroxypyrimidine-1 M potassium oxonate) or lovastatin.

In another aspect, the second chemotherapeutic agent can be a cytokine such as G-CSF (granulocyte colony stimulating factor). In another aspect, a compound of the present invention, or a pharmaceutically acceptable salt, prodrug, metabolite, analog or derivative thereof, may be administered in combination with radiation therapy. Radiation therapy can also be administered in combination with a compound of the invention and another chemotherapeutic agent described herein as part of a multiple agent therapy. In yet another aspect, a compound of the invention, or a pharmaceutically acceptable salt, prodrug, hydrate, or solvate thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™) or CMFP (cyclophosphamide, methotrexate, 5-fluorouracil and prednisone).

In some embodiments, a compound of the invention, or a pharmaceutically acceptable salt, prodrug, hydrate, or solvate thereof, may be administered with an inhibitor of an enzyme, such as a receptor or non-receptor kinase. Receptor and non-receptor kinases of the invention are, for example, tyrosine kinases or serine/threonine kinases. Kinase inhibitors of the invention are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P 154 (targets JAK), WHI-P 131 (targets JAK), sorafenib/Nexavar (targets RAF kinase, VEGFR-1, VEGFR-2, VEGFR-3, PDGFR-13, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCID-469 (targets MAP/MEK), GW681323 (targets MAP/MEK), CC-401 (targets JNK), CEP-1347 (targets JNK), and PD 332991 (targets CDK).

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Further, it should be understood that the order of steps or order for performing certain actions are immaterial so long as the invention remains operable. Moreover, two or more steps or actions may be conducted simultaneously.

The compounds, or pharmaceutically acceptable salts, hydrates or solvates thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In some embodiments, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of compounds of the invention can be found in *Remington: the Science and Practice of Pharmacy*, 19$^{th}$ edition, Mack Publishing Co., Easton, Pa. (1995). In one aspect, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

In some embodiments, the compound is prepared for oral administration, wherein the s compound of the invention or a pharmaceutically acceptable salt, hydrate, or solvate thereof is combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose, saccharin, xylitol, and the like. When a dosage unit form is a capsule, it often contains, in addition to materials of the above type, a liquid carrier such as a fatty oil.

In some embodiments, various other materials are present as coatings or to modify the physical form of the dosage unit. For instance, in some embodiments, tablets are coated with shellac, sugar or both. In some embodiments, a syrup or elixir contains, in addition to the active ingredient, sucrose as a sweetening agent, methyl and propylparabens as preservatives, a dye and a flavoring such as cherry or orange flavor, and the like.

For some embodiments relating to parental administration, the compounds, or salts, solvates, or hydrates thereof, can be combined with sterile aqueous or organic media to form injectable solutions or suspensions. In some embodiments, injectable compositions are aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, in another embodiment, the compositions contain about 1 to 50%, of the active ingredient.

For example, injectable solutions are produced using solvents such as sesame or peanut oil or aqueous propylene glycol, as well as aqueous solutions of water-soluble pharmaceutically-acceptable salts of the compounds. In some embodiments, dispersions are prepared in glycerol, liquid polyethylene glycols and mixtures thereof in oils. Under ordinary conditions of storage and use, these preparations contain a preservative to prevent the growth of microorganisms. The terms "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

For rectal administration, suitable pharmaceutical compositions are, for example, topical preparations, suppositories or enemas. Suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, in another embodiment, compositions contain about 1 to 50%, of the active ingredient.

In some embodiments, the compounds are formulated to deliver the active agent by pulmonary administration, e.g., administration of an aerosol formulation containing the active agent from, for example, a manual pump spray, nebulizer or pressurized metered-dose inhaler. In some embodiments, suitable formulations of this type also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a headspace representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

For nasal administration, either a solid or a liquid carrier can be used. The solid carrier includes a coarse powder having particle size in the range of, for example, from about 20 to about 500 microns and such formulation is administered by rapid inhalation through the nasal passages. In some embodiments where the liquid carrier is used, the formulation is administered as a nasal spray or drops and includes oil or aqueous solutions of the active ingredients.

Also contemplated are formulations that are rapidly dispersing dosage forms, also known as "flash dose" forms. In particular, some embodiments of the present invention are formulated as compositions that release their active ingredients within a short period of time, e.g., typically less than about five minutes, in another embodiment, less than about ninety seconds, in another embodiment, less than about thirty seconds and in another embodiment, in less than about ten or fifteen seconds. Such formulations are suitable for administration to a subject via a variety of routes, for example by insertion into a body cavity or application to a moist body surface or open wound.

Typically, a "flash dosage" is a solid dosage form that is administered orally, which rapidly disperses in the mouth, and hence does not require great effort in swallowing and allows the compound to be rapidly ingested or absorbed through the oral mucosal membranes. In some embodiments, suitable rapidly dispersing dosage forms are also used in other applications, including the treatment of wounds and other bodily insults and diseased states in which release of the medicament by externally supplied moisture is not possible.

"Flash dose" forms are known in the art; see for example, effervescent dosage forms and quick release coatings of insoluble microparticles in U.S. Pat. Nos. 5,578,322 and 5,607,697; freeze dried foams and liquids in U.S. Pat. Nos. 4,642,903 and 5,631,023; melt spinning of dosage forms in U.S. Pat. Nos. 4,855,326, 5,380,473 and 5,518,730; solid, free-form fabrication in U.S. Pat. No. 6,471,992; saccharide-based carrier matrix and a liquid binder in U.S. Pat. Nos. 5,587,172, 5,616,344, 6,277,406, and 5,622,719; and other forms known to the art.

The compounds of the invention are also formulated as "pulsed release" formulations, in which the compound is released from the pharmaceutical compositions in a series of releases (i.e., pulses). The compounds are also formulated as "sustained release" formulations in which the compound is continuously released from the pharmaceutical composition over a prolonged period.

Also contemplated are formulations, e.g., liquid formulations, including cyclic or acyclic encapsulating or solvating agents, e.g., cyclodextrins, polyethers, or polysaccharides (e.g., methylcellulose), or in another embodiment, polyanionic β-cyclodextrin derivatives with a sodium sulfonate salt group separate from the lipophilic cavity by an alkyl ether spacer group or polysaccharides. In some embodiments, the agent is methylcellulose. In another embodiment, the agent is a polyanionic β-cyclodextrin derivative with a sodium sulfonate salt separated from the lipophilic cavity by a butyl ether spacer group, e.g., CAPTISOL® (CyDex Pharmaceuticals Inc., Lenexa, Kans.). One skilled in the art can evaluate suitable agent/disclosed compound formulation ratios by preparing a solution of the agent in water, e.g., a 40% by weight solution; preparing serial dilutions, e.g. to make solutions of 20%, 10, 5%, 2.5%, 0% (control), and the like; adding an excess (compared to the amount that can be solubilized by the agent) of the disclosed compound; mixing under appropriate conditions, e.g., heating, agitation, sonication, and the like; centrifuging or filtering the resulting mixtures to obtain clear solutions; and analyzing the solutions for concentration of the disclosed compound.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Sulfoneamides containing a sulfone linker and having general formula [6].

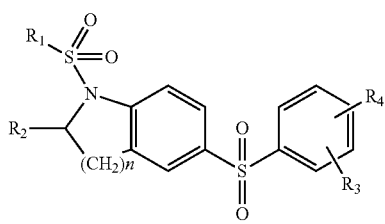

[6]

can be prepared according to Scheme 1 from Compound [7] and its derivatives, which are commercially available.

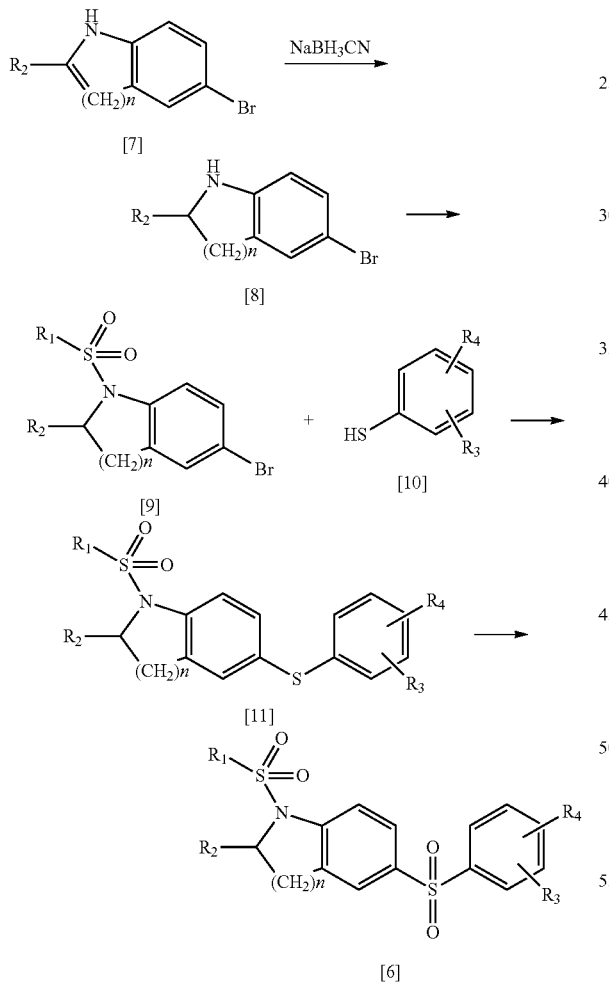

Reduction of Compound [7] using sodium borocyanohydride will give compound [8] (See Journal of the American Chemical Society, 128(44), 14264-14265; 2006). Then the preparation of the sulfoneamide compound [Compound 9] can be prepared by reacting Compound [8] with a substituted-sulfonyl chloride, as described above at the first step of Scheme 1. The resulting product (Compound [9]) is then reacted with the appropriate thiol (e.g., Compound [10] as shown) using a base such as potassium carbonate or cesium carbonate in DMF, according to known procedures (See Synthesis 1 (79-84), 2010; WO2010048694; Journal of the American Chemical Society, 132(4) 1261-1263 (2010); Tetrahedron, 66(12), 2119-2122, 2010; Journal of Medicinal Chemistry 996) 835-7, 1966) to give the product, Compound [11] that undergoes an oxidation reaction to give the desired product (Compound [6]).

Alternatively compounds of the invention may be prepared according to the following scheme, starting from a commercially available compound. Starting by preparation of sulfoneamide of the appropriate indoline and then by a Friedel Craft reaction preparing the end product.

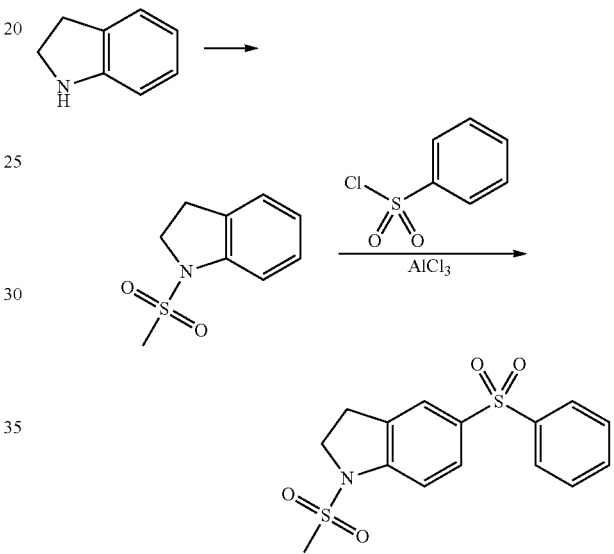

Example 1

Synthesis of 5-((2,3-dihydrobenzo[b][1,4]dioxin-6-yl)sulfonyl)-2-methyl-1-(methylsulfonyl)indoline

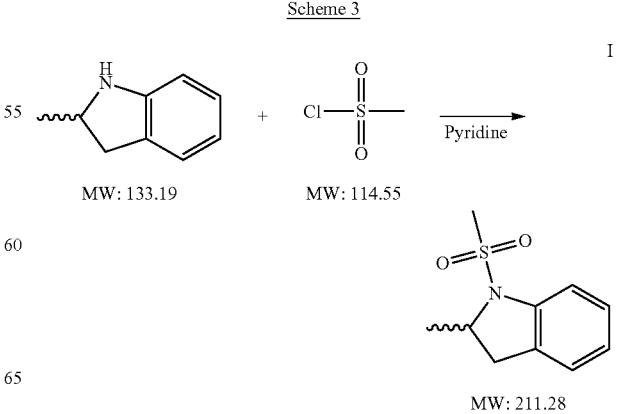

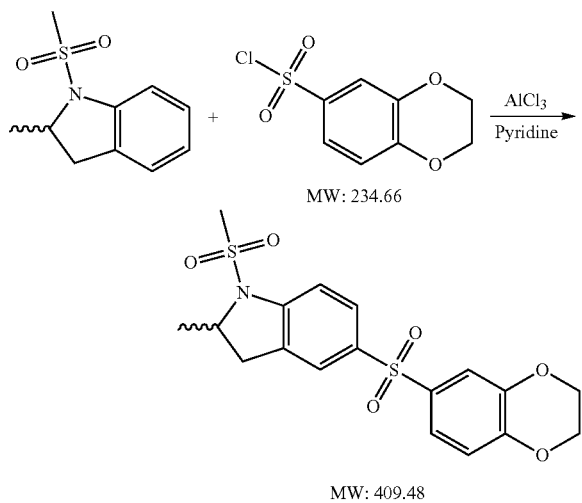

MW: 234.66

MW: 409.48

Reagents

| Reagent/raw material | MW (g/mole) | Quantity | | moles | Mole ratio |
|---|---|---|---|---|---|
| 2-methylindoline | 161.20 | 1 | g | 7.5 mmol | 1 eq. |
| methanesulfonyl chloride | 114.55 | 1.04 | g | 9.0 mmol | 1.5 eq. |
| 2-methyl-1-(methyl-sulfonyl)indoline | 239.29 | 276 | mg | 1.3 mmol | 1.2 eq. |
| 2,3-dihydro-benzo[b][1,4]dioxine-6-sulfonyl chloride | 375.93 | 250 | mg | 1.06 mmol | 1.0 eq. |
| Aluminium chloride | 133.3 | 170 | mg | 1.3 mmol | 1.2 eq. |

Step I: 2-methylindoline was dissolved in 5 mL dry pyridine, and methanesulfonyl chloride was dropped in 2 portions under $N_2$. The reaction was stirred for 2 hours at room temperature and an intense red color developed. When the reaction was complete as determined by HPLC (product Rt=8.51 min, st. material Rt=4.18 min) using the H2O-Acetonitrile (CAN) gradient given below with a Gemini®-NS C18, 3 μm, 100 Å, 150×4.6 mm column chromatography as well as by TLC (8/2 PE/EtOAC), the crude reaction was poured into 100 mL cold 0.5M HCl, and extracted twice with 50 mL $CH_2Cl_2$. The organic phase was evaporated, and the evaporation residue was purified by passing through a silica plug (~100 g silica gel in large sinter glass). The product eluted in 7/3 PE/EtOAC, while all of the pink polar byproduct was retained on silica. The organic phase was dried on $Na_2SO_4$, and then evaporated and used for the next step without further purification (Product 100% pure, 455 mg, yield ~30%).

HPLC Purification Protocol

| Time (min) | Flow | H₂O (%) | ACN (%) |
|---|---|---|---|
| | 1 | 100 | 0 |
| 0.02 | 1 | 100 | 0 |
| 11.0 | 1 | 0 | 100 |
| 13.0 | 1 | 100 | 0 |
| 18.0 | 1 | 100 | 0 |
| 18.1 | 0.2 | 100 | 0 |

Step II: 2,3-dihydrobenzo[b][1,4]dioxine-6-sulfonyl chloride was stirred in dichloroethane with aluminium chloride for 10 minutes, and then 2-methyl-1-(methylsulfonyl)indoline was dropped in with stirring. The reaction was heated to 70° C. with stirring in a pressure ampoule for 1 hour. The reaction mixture was evaporated and redissolved in EtOAc and then washed twice with 50 mL of cold water and then with brine. The organic phase was dried, evaporated and separated on CombiFlash®. The final product eluted at 8/2 EtoAc/PE to provide 93 mg of 100% pure product (overall yield 7.5%).

Analysis: HPLC–100% purity, as determined by the HPLC protocol described above.

MS–(ES$^+$) Calcd. for $C_{18}H_{19}NO_6S_2$ 409.07. found 410.45 (M+H).

Example 2

Synthesis of 5-((2,3-dihydrobenzo[b][1,4]dioxin-6-yl)sulfonyl)-1-((4-methoxyphenyl)sulfonyl)-2-methylindoline Scheme 4

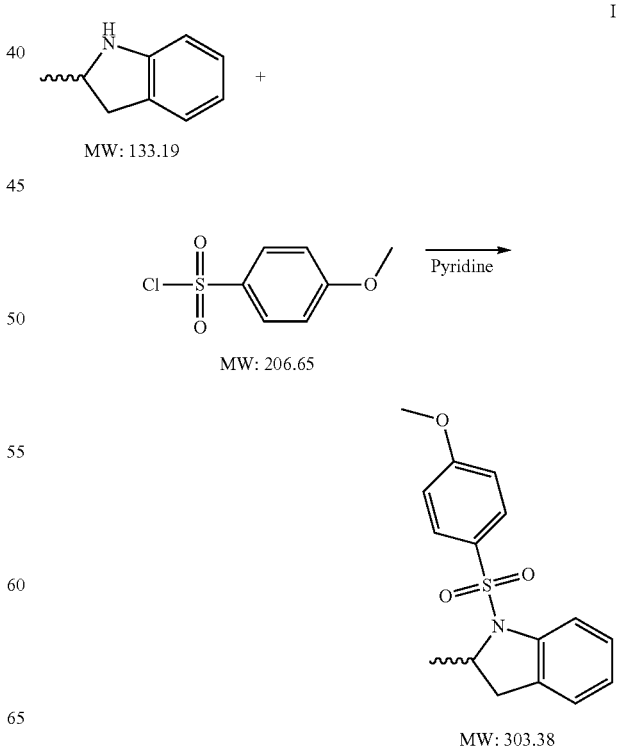

MW: 133.19

MW: 206.65

MW: 303.38

81

-continued

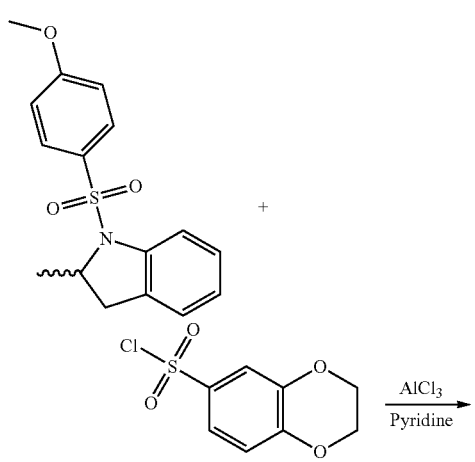

MW: 234.66

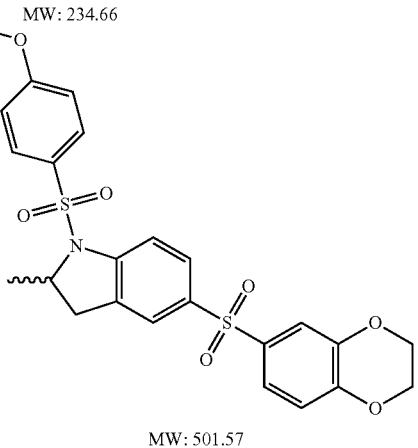

MW: 501.57

Reagents

| Reagent/raw material | MW (gr/mole) | Quantity | moles | Mole ratio |
|---|---|---|---|---|
| 2-methylindoline | 161.20 | 177 mg | 1.33 mmol | 1 eq. |
| 4-methoxybenzene-1-sulfonyl chloride | 206.65 | 250 mg | 1.21 mmol | 1.1 eq. |
| 1-((4-methoxyphenyl)sulfonyl)-2-methylindoline | 303.38 | 267 mg | 0.88 mmol | 1.0 eq. |
| 2,3-dihydro-benzo[b][1,4]dioxine-6-sulfonyl chloride | 234.66 | 206 mg | 0.88 mmol | 1.0 eq. |
| Aluminium chloride | 133.3 | 147 mg | 1.1 mmol | 1.25 eq. |

Step I: 2-methylindoline was dissolved in 5 mL dry pyridine, and 4-methoxybenzene-1-sulfonyl chloride was dropped in 2 portions under $N_2$. The reaction was stirred for 2 hours at room temperature and an intense red color developed. When complete as determined by HPLC (product Rt=9.857 min) using the protocol described in Example 1, as well as by TLC (8/2 PE/EtOAC), the crude reaction mixture was poured into 100 mL of cold 0.5M HCl, and extracted twice with 50 mL $CH_2Cl_2$. The organic phase was evaporated, and the evaporation residue was purified by passing through a silica plug (~100 g silica gel in large sinter glass). The product eluted in 7/3 PE/EtOAC, while all of the pink polar byproduct

82 was retained on silica. The organic phase was dried on $Na_2SO_4$, evaporated and used for the next step without further purification (Product 100% pure, 267 mg, yield 66%).

Step II: 2,3-dihydrobenzo[b][1,4]dioxine-6-sulfonyl chloride was stirred in dichloromethane with aluminium chloride for 10 minutes, and then 1-((4-methoxyphenyl)sulfonyl)-2-methylindoline was dropped in with the stirring. The reaction was heated to 70° C. with stirring in a pressure ampoule for 1 hour. The reaction mixture was evaporated and redissolved in EtOAc and then washed twice with 50 mL of cold water and then with brine. The organic phase was dried, evaporated and separated on CombiFlash®. The final product eluted at 8/2 EtoAc/PE to provide 114 mg of 100% pure product (overall yield 15%).

$^1$H-NMR 300 MHz, (CDCl$_3$) δ 1.45 (CH$_3$, d), 2.56 (1H, dd), 3.05 (1H, dd), 3.69 (3H, s), 4.28 (4H, m), 4.42 (1H, m), 6.95 (1H, d), 7.08 (1H, m), 7.15 (1H, m), 7.29 (1H, t), 7.30 (1H, m), 7.41 (1H, s), 7.59 (1H, s), 7.71 (1H, d), 7.78 (1H, dd).

Analysis: HPLC–100% purity and $R_1$=9.943, using the protocol described in Example 1 above. MS–(ES$^+$) Calcd. for $C_{24}H_{23}NO_7S_2$ 501.61. found 502.36 (M+H).

Example 3

Synthesis of 1-(5-((2,3-dihydrobenzo[b][1,4]dioxin-6-yl)sulfonyl)-2-methylindolin-1-yl)ethanone Scheme 5

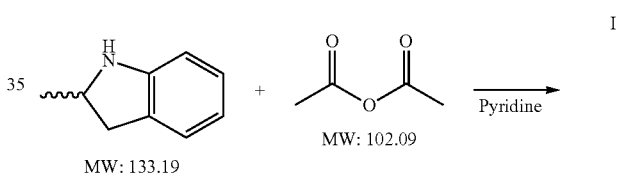

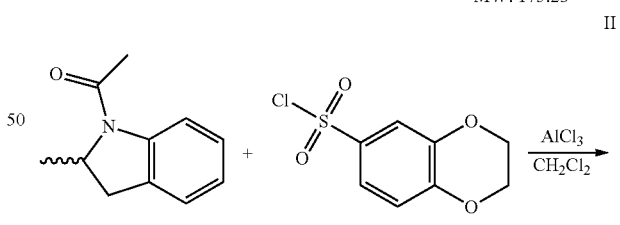

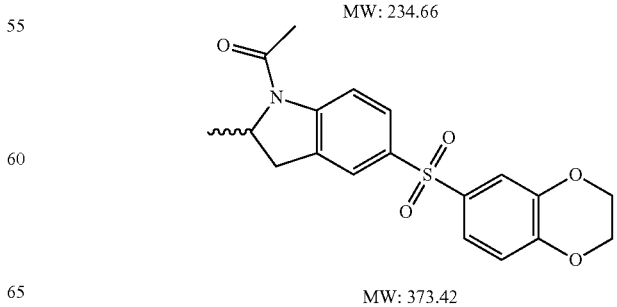

MW: 373.42

Reagents

| Reagent/raw material | MW (g/mole) | Quantity | moles | Mole ratio |
|---|---|---|---|---|
| 2-methylindoline | 133.19 | 1 g | 7.5 mmol | 1.0 eq. |
| acetic anhydride | 102.09 | 5 ml | excess | excess |
| 1-(2-methylindolin-1-yl)ethanone | 175.23 | 170 mg | 0.96 mmol | 1.0 eq. |
| Aluminium chloride | 133.3 | 306 mg | 2.3 mmol | 2.5 eq. |
| 2,3-dihydro-benzo[b][1,4]dioxine-6-sulfonyl chloride | 234.66 | 215 mg | 0.92 mmol | 1.0 eq |
| 1-(5-((2,3-dihydro-benzo[b][1,4]dioxin-6-yl)sulfonyl)-2-methylindolin-1-yl)ethanone | 373.42 | | | |

Step I: 2-methylindoline was stirred in 5 mL of acetic anhydride with 1 mL pyridine. The reaction was stirred for 2 hours at room temperature, by that time it was complete as determined by TLC (8/2 PE/EtOAC). The crude reaction was evaporated and dissolved in 50 mL EtOAc, washed with water, brine, dried on $Na_2SO_4$, and used for the next step without further purification. This material is very acid-labile and should not be exposed to acidic conditions.

Step II: 2,3-dihydrobenzo[b][1,4]dioxine-6-sulfonyl chloride was stirred in dichloromethane with aluminium chloride for 10 minutes, and then 1-(2-methylindolin-1-yl)ethanone was dropped in with stirring. The reaction was heated to 70° C. with stirring in a pressure ampoule for 1 hour. The reaction mixture was evaporated and redissolved in EtOAc and then washed twice with 50 mL of cold water and then with brine. The organic phase was dried, evaporated and separated on CombiFlash®. The final product eluted at 8/2 EtOAc/PE to provide 93 mg of 99.3% pure product (overall yield 7.5%).

Analysis: HPLC−99.13% purity, as determined by the protocol described in Example 1 above.

MS−(ES+) Calcd. for C19H19NO5S 373.46. found 374.36 (M+H).

Example 4

Synthesis of 5-((2,3-dihydrobenzo[b][1,4]dioxin-6-yl)sulfonyl)-1-((4-fluorophenyl)sulfonyl)-2-methylindoline Scheme 6

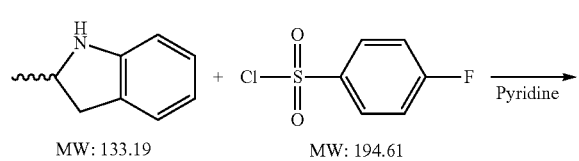

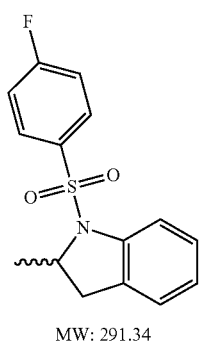

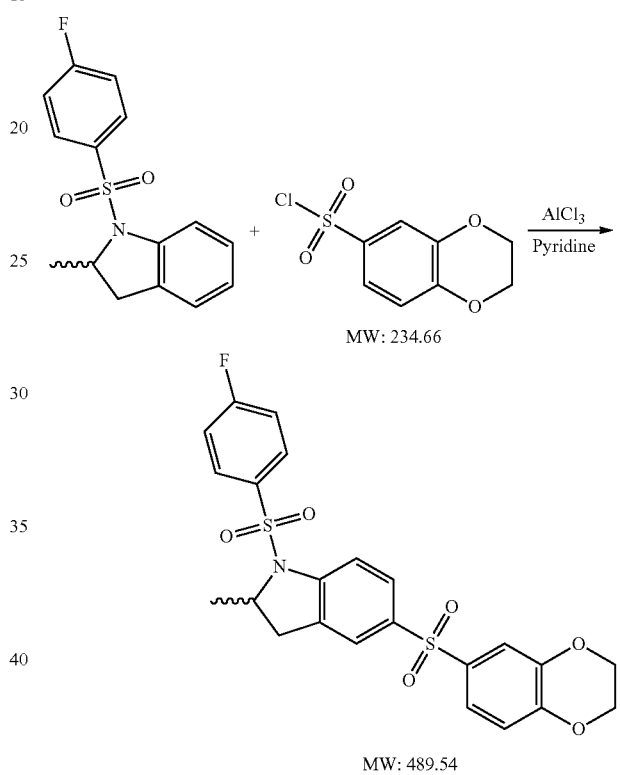

Reagents

| Reagent/raw material | MW (g/mole) | Quantity | moles | Mole ratio |
|---|---|---|---|---|
| 2-methylindoline | 161.20 | 177 mg | 1.33 mmol | 1 eq. |
| 4-fluorobenzene-1-sulfonyl chloride | 194.61 | 235 mg | 1.33 mmol | 1.0 eq. |
| 1-((4-fluorophenyl)sulfonyl)-2-methylindoline | 291.34 | 267 mg | 0.88 mmol | 1.0 eq. |
| 2,3-dihydro-benzo[b][1,4]dioxine-6-sulfonyl chloride | 234.66 | 206 mg | 0.88 mmol | 1.0 eq. |
| Aluminium chloride | 133.3 | 147 mg | 1.1 mmol | 1.25 eq. |

Step I: 2-methylindoline was dissolved in 5 mL dry pyridine, and 4-methoxybenzene-1-sulfonyl chloride was dropped in 2 portions under $N_2$. The reaction was stirred for 2 hours at room temperature and an intense red color developed. When the reaction was complete as determined by HPLC using the protocol described above, as well as by TLC (8/2 PE/EtOAC), the crude reaction mixture was poured into 100 mL cold 0.5M HCl, and extracted twice with 50 mL CH$_2$Cl$_2$. The organic phase was evaporated, and the evaporation residue was purified by passing through a silica plug (~100 g silica gel in large sinter glass). The product eluted in 7/3 PE/EtOAC, while all of the pink polar byproduct was retained on silica. The organic phase was dried on Na$_2$SO$_4$, and then evaporated and used for the next step without further purification (Product 100% pure, 378 mg, yield 99%).

Step II: 2,3-dihydrobenzo[b][1,4]dioxine-6-sulfonyl chloride was stirred in dichloromethane with aluminium chloride for 10 minutes, and then 1-((4-fluorophenyl)sulfonyl)-2-methylindoline was dropped in with the stirring. The reaction was heated to 70° C. with stirring in the pressure ampoule for 1 hour. The reaction mixture was evaporated and redissolved in EtOAc and then washed twice with 50 mL of cold water and then with brine. The organic phase was dried, evaporated and separated on CombiFlash®. The final product eluted at 8/2 EtoAc/PE to provide 74 mg of 95.5% pure product (overall yield 15%).

Analysis: $^1$H-NMR 300 MHz, (CDCl$_3$) δ 1.45 (CH3, d), 2.58 (1H, dd), 3.08 (1H, dd), 4.41 (1H, m), 4.28 (4H, m), 6.95 (1H, d), 7.14 (2H, m), 7.36 (1H, m), 7.41 (2H, m), 7.59 (1H, s), 7.68 (1H, m), 7.77 (1H, m). HPLC–95.5%, Rt=9.849, as determined by the protocol described in Example 1 above. MS–(ES+) Calcd. for C23H20FNO6S2 489.6. found 490.5 (M+H).

Example 5

Synthesis of 5-((2,3-dihydrobenzo[b][1,4]dioxin-6-yl)sulfonyl)-2-(methylsulfonyl)isoindoline

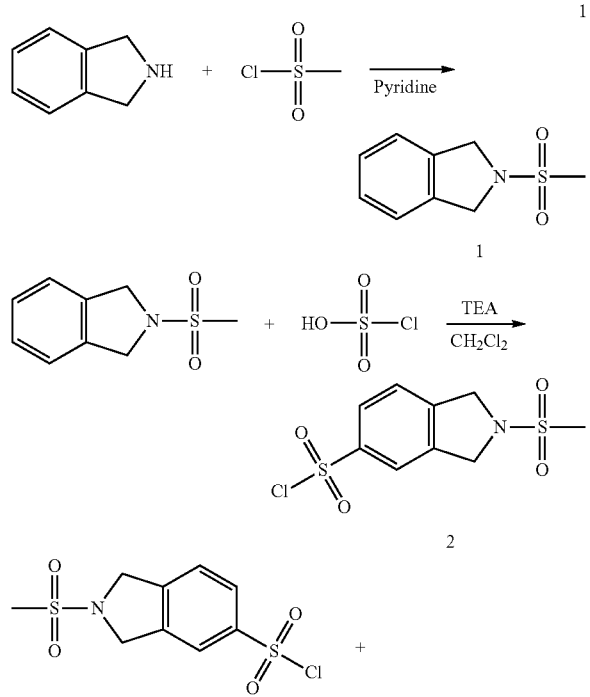

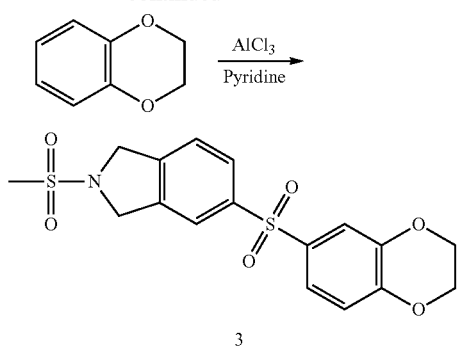

Reagents

| Reagent/raw material | MW (gr/mole) | Quantity | moles |
|---|---|---|---|
| Isoindoline | 119.16 | 0.5 g | 4.2 |
| methanesulfonyl chloride | 114.55 | 0.71 g | 6.3 |
| 2-(methylsulfonyl)isoindoline | 197.25 | 325 mg | 1.64 |
| sulfurochloridic acid | 116.52 | 5 mL | excess |
| 2-(methylsulfonyl)isoindoline-5-sulfonyl chloride | 295.76 | 0.35 g | 1.13 |
| 2,3-dihydrobenzo[b][1,4]dioxine | 136.15 | 0.2 | 1.4 |
| AlCl$_3$ | 133 | 0.3 | 2.27 |

Step 1: Isoindoline was dissolved in 5 mL dry pyridine, and methanesulfonyl chloride was dropped in. The reaction was stirred overnight at room temperature and an intense red color developed. When complete by HPLC using the protocol described in Example 1, as well as by LCMS, the crude reaction mixture was poured into 100 mL cold 1M KHSO$_4$, and extracted twice with 50 mL of CH$_2$Cl$_2$. The organic phase was dried, evaporated and separated on CombiFlash® (PE/EtOAC) to provide 325 mg of pure product (39% yield).

Step 2: 2-(methylsulfonyl)isoindoline was added to cooled chlorosulfonic acid with stirring. The reaction mixture was allowed to warm to room temperature and stirred for 6 hours. The reaction mixture was slowly and carefully dropped into stirred ice in water and stirred for 20 minutes. The resulting product was extracted twice with 50 mL CH$_2$Cl$_2$ and then washed twice with 50 mL cold water and then finally with brine. The organic phase was dried, evaporated and was pure enough for the next step (Product 100% pure, 0.35 g, yield 100%).

Step 3: 2-(methylsulfonyl)isoindoline-5-sulfonyl chloride was stirred into dichloroethane with aluminium chloride for 10 minutes, and then 2,3-dihydrobenzo[b][1,4]dioxine was dropped in with stirring. The reaction was heated to 70° C. with stirring in a pressure ampoule for 1 hour. The reaction mixture was evaporated and redissolved in EtOAc and then washed twice with 50 mL cold water and then with brine. The organic phase was dried, evaporated and separated on CombiFlash®. The final product eluted at 8/2 EtoAc/PE to provide 32 mg of 99% pure product.

Analysis: HPLC:95.5% pure, Rt=8.193 minutes, using the protocol described in Example 1 above. MS−(ES+) Calcd. for C17H17NO6S2 395.5. found 396.47 (M+H).

Example 6

Synthesis of 6-((2,3-dihydrobenzo[b][1,4]dioxin-6-yl)sulfonyl)-1-(methylsulfonyl)-1,2,3,4-tetrahydroquinoline Scheme 8

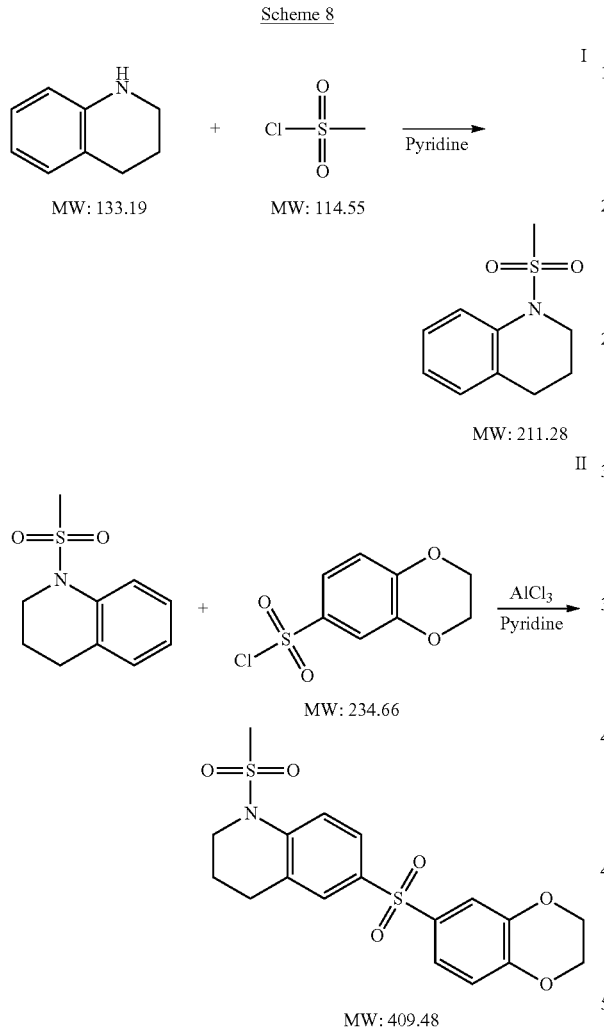

Reagents

| Reagent/raw material | MW (g/mole) | Quantity | moles | Mole ratio |
|---|---|---|---|---|
| 1,2,3,4-tetrahydroquinoline | 133.19 | 1000 mg | 7.51 | 1.0 eq. |
| methanesulfonyl chloride | 114.55 | 2160 mg | 18.8 | 2.5 eq. |
| 1-(methylsulfonyl)-1,2,3,4-tetrahydroquinoline | 211.28 | 340 mg | 1.60 | 1.0 eq. |
| 2,3-dihydro-benzo[b][1,4]dioxine-6-sulfonyl chloride | 234.66 | 451 mg | 1.92 | 1.2 eq. |
| 6-((2,3-dihydro-benzo[b][1,4]dioxin-6-yl)sulfonyl)-1-(methylsulfonyl)-1,2,3,4-tetrahydroquinoline | 409.48 | | | |
| Aluminum chloride | 133.3 | 350 mg | 2.63 | 2.5 eq. |

Step I: 1,2,3,4-tetrahydroquinoline was dissolved in 5 mL dry pyridine, and methanesulfonyl chloride was dropped in 2 portions under $N_2$. The reaction was stirred for 2 hours at room temperature and an intense red color developed. When the reaction was complete as determined by TLC (8/2 PE/EtOAC), the crude reaction mixture was poured into 100 mL cold 0.5M HCl, and extracted twice with 50 mL $CH_2Cl_2$. The organic phase was evaporated, and the evaporation residue was purified by passing through a silica plug (~100 g silica gel in large sinter glass). The product eluted in 7/3 PE/EtOAC, while all of the pink polar byproduct was retained on silica. The organic phase was dried on $Na_2SO_4$, and then evaporated and used for the next step without further purification (Product 340 mg, yield ~25%).

Step II: 2,3-dihydrobenzo[b][1,4]dioxine-6-sulfonyl chloride was stirred in dichloromethane with aluminium chloride for 10 minutes, and then 1-(methylsulfonyl)-1,2,3,4-tetrahydroquinoline was dropped in with stirring. The reaction was heated to 70° C. with stirring in a pressure ampoule for 1 hour. The reaction mixture was evaporated and redissolved in EtOAc and then washed twice with 50 mL cold water and then with brine. The organic phase was dried, evaporated and separated on CombiFlash®. The final product eluted at 8/2 EtoAc/PE to provide 335 mg of 100% pure product (overall yield 13%).

Analysis: $^1$H-NMR 300 MHz, (CDCl3) δ 1.90 (CH2, q), 2.85 (2H, t), 3.16 (3H, s), 3.71 (2H, t), 4.43 (4H, m), 6.72 (1H, d), 7.06 (1H, d), 7.39 (1H, s), 7.43 (1H, d), 7.71 (1H, s).

HPLC−100%, Rt=8.777 min, as determined by the protocol described in Example 1 above.

MS−(ES+) Calcd. for C18H19NO6S2 409.5. found 410.45 (M+H).

Example 7

Synthesis of 5-((2,3-dihydrobenzo[b][1,4]dioxin-6-yl)sulfonyl)-2-methyl-1-(phenylsulfonyl)indoline Scheme 9

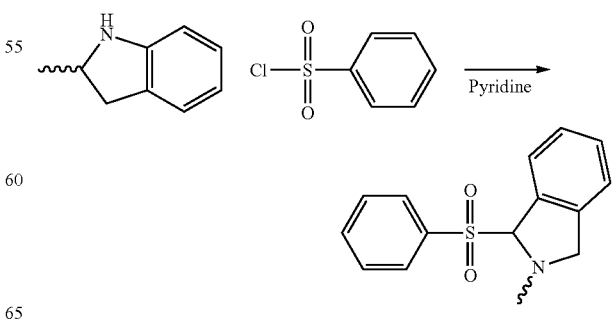

89
-continued

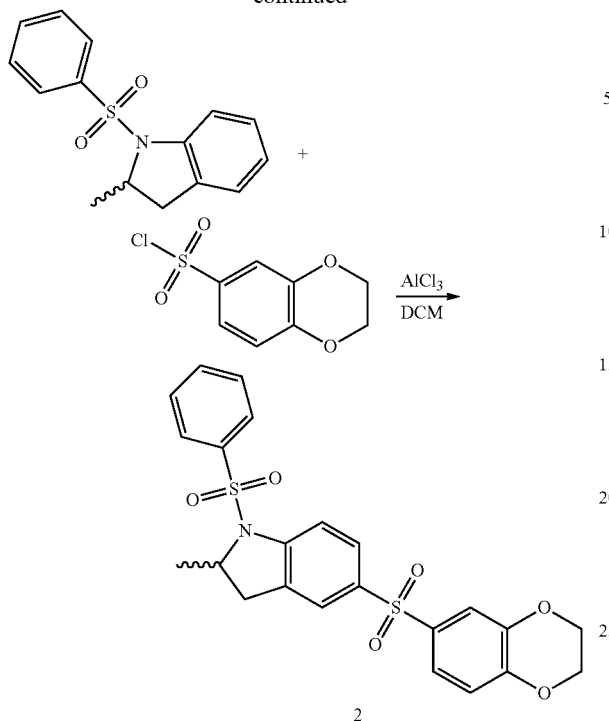

Reagents

| Reagent/raw material | MW (g/mole) | Quantity | moles |
|---|---|---|---|
| 2-methylindoline | 133.20 | 1 g | 7.5 mmol |
| benzenesulfonyl chloride | 176.62 | 1.98 g | 11 mmol |
| 2-methyl-1-(phenylsulfonyl)indoline | 273.35 | 0.76 g | 2.77 mmol |
| 2,3-dihydrobenzo[b][1,4]dioxine-6-sulfonyl chloride | 234.66 | 0.5 g | 2.13 mmol |
| Aluminium chloride | 133.3 | 0.369 g | 2.77 mmol |

Step 1: 2-methylindoline was dissolved in 5 mL dry pyridine, and benzenesulfonyl chloride was dropped in. The reaction was stirred for 2 hours at room temperature and an intense red color developed. When complete as determined by HPLC using the protocol in Example 1 above, as well as by LCMS, the crude reaction was poured into 100 mL cold 1M KHSO$_4$, and extracted twice with 50 mL CH$_2$Cl$_2$. The organic phase was dried, evaporated and purified by CombiFlash® to provide 2 grams of 100% pure product (97% yield).

Step 2: 2,3-dihydrobenzo[b][1,4]dioxine-6-sulfonyl chloride was stirred in dichloroethane with aluminium chloride for 10 minutes, and then 2-methyl-1-(phenylsulfonyl)indoline dropped in with stirring. The reaction was heated to 70° C. with stirring in a pressure ampoule overnight. The reaction was evaporated and redissolved in EtOAc and then washed twice with 50 mL cold water and then brine. The organic phase was dried over NaSO$_4$, evaporated and separated on CombiFlash®. The final product eluted at 8/2 EtOAc/PE to provide 203 mg of 95.3% pure product (overall yield 15.5%).

90

Analysis: HPLC:Rt=9.83 minutes 95.28% pure, as determined by the protocol in Example 1 above. MS–471.55 (calc.), 472.49 (MS+H+).

Example 8

Synthesis of N-(4-((2,3-dihydrobenzo[b][1,4]dioxin-6-yl)sulfonyl)phenyl)-N-isopropylmethanesulfonamide Scheme 10

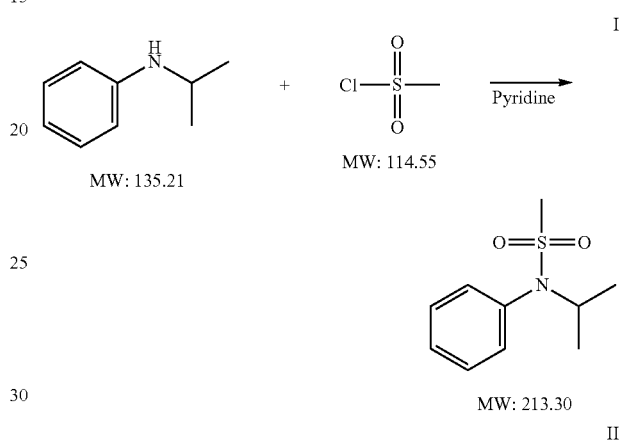

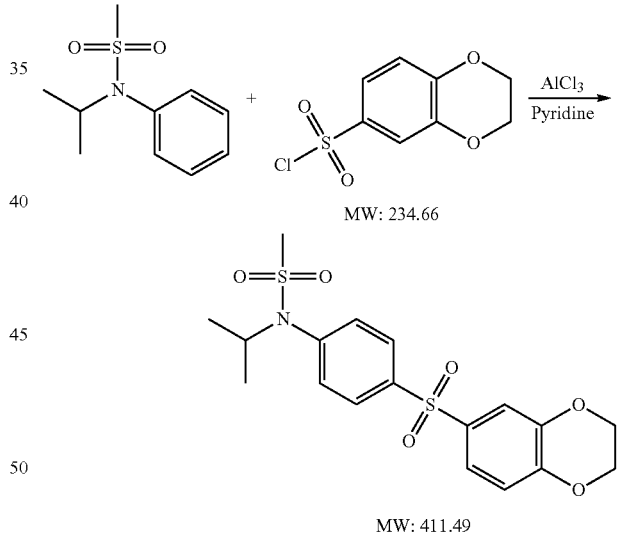

Reagents

| Reagent/raw material | MW (g/mole) | Quantity | moles | Mole ratio |
|---|---|---|---|---|
| N-isopropylaniline | 135.21 | 330 mg | 2.44 | 1.0 eq. |
| methanesulfonyl chloride | 114.55 | 560 mg | 4.8 | 2.0 eq. |
| N-isopropyl-N-phenylmethanesulfonamide | 213.30 | 250 mg | 1.17 | 1.1 eq. |
| 2,3-dihydrobenzo[b][1,4]dioxine-6-sulfonyl chloride | 234.66 | 250 mg | 1.07 | 1.0 eq. |

-continued

| Reagent/raw material | MW (g/mole) | Quantity | moles | Mole ratio |
|---|---|---|---|---|
| N-(4-((2,3-dihydrobenzo[b][1,4]dioxin-6-yl)sulfonyl)phenyl)-N-isopropylmethanesulfonamide | 411.49 | | | |
| Aluminum chloride | 133.3 | 353 mg | 2.65 | 2.5 eq. |

Step I: N-isopropylaniline was dissolved in 5 mL dry pyridine, and methanesulfonyl chloride was dropped in 2 portions under N₂. The reaction was stirred for 2 hours at room temperature and an intense red color developed. When the reaction was complete as determined by TLC (8/2 PE/EtOAC), the crude reaction mixture was poured into 100 mL cold 0.5M HCl, and extracted twice with 50 mL CH$_2$Cl$_2$. The organic phase was evaporated, and the evaporation residue was purified by passing through a silica plug (~100 g silica gel in large sinter glass). The product eluted in 7/3 PE/EtOAC, while all of the pink polar byproduct was retained on silica. The organic phase was dried on Na$_2$SO$_4$, and then evaporated and used for the next step without further purification (Product 250 mg, Rt=8.107 minutes, yield ~48%).

Step II: 2,3-dihydrobenzo[b][1,4]dioxine-6-sulfonyl chloride was stirred in dichloromethane with aluminium chloride for 10 minutes, and then N-isopropyl-N-phenylmethanesulfonamide was dropped in with stirring. The reaction was heated to 70° C. with stirring in a pressure ampoule for 1 hour. The reaction mixture was evaporated and redissolved in EtOAc and then washed twice with 50 mL cold water and then with brine. The organic phase was dried, evaporated and separated on CombiFlash®. The final product eluted at 8/2 EtOAc/PE (Final product 100% pure, 22 mg, overall yield 2.7%). However as indicated in the NMR spectrum below, only the hydrolysis product lacking the isopropyl group was obtained.

Analysis: $^1$H-NMR 300 MHz, (CDCl$_3$) δ 3.11 (3H, s), 4.30 (4H, m), 7.06 (1H, d), 7.35 (1H, s), 7.39 (1H, d), 7.35 (2H, d), 7.88 (2H, d), 10.45 (NH, br. s). HPLC–100% pure, Rt=7.909 minutes, as determined by the protocol in Example 1 above. MS–(ES+) Calcd. for C18H21NO6S2 411.5. found 413.5 (M+H).

Example 9

Synthesis of 5-((2,3-dihydrobenzo[b][1,4]dioxin-6-yl)sulfonyl)-1-(methylsulfonyl)indoline Scheme 11

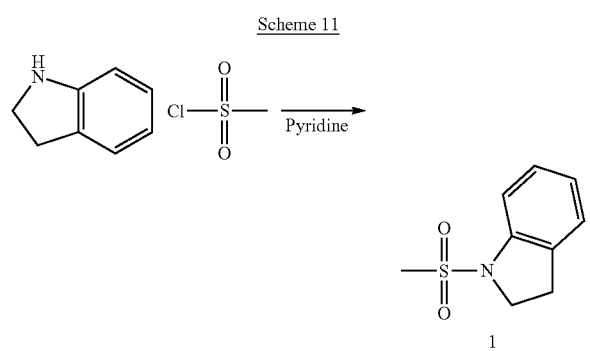

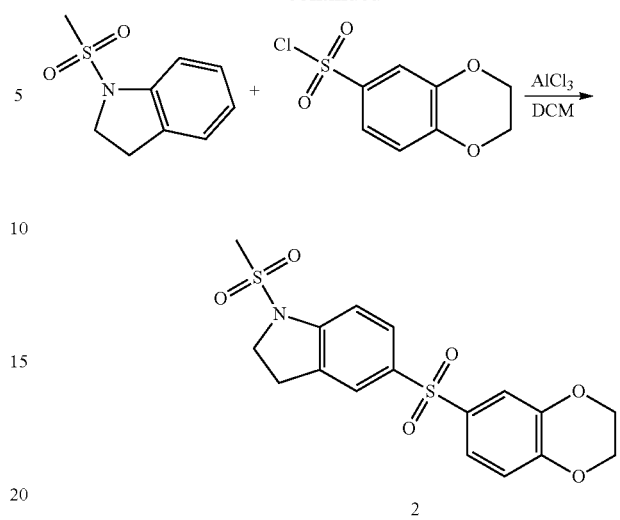

Reagents

| Reagent/raw material | MW (g/mole) | Quantity | moles |
|---|---|---|---|
| Indoline | 119.16 | 1 g | 8.4 mmol |
| methanesulfonyl chloride | 114.55 | 1.43 g | 12 mmol |
| 1-(methanesulfonyl)indoline | 197.25 | 0.273 g | 1.38 mmol |
| 2,3-dihydrobenzo[b][1,4]dioxine-6-sulfonyl chloride | 234.66 | 0.5 g | 1 mmol |
| Aluminium chloride | 133.3 | 0.184 g | 1.38 mmol |

Step 1: Indoline was dissolved in 5 mL dry pyridine, and methanesulfonyl chloride was dropped in. The reaction was stirred overnight at room temperature and an intense red color developed. When complete by HPLC using the HPLC protocol described in Example 1, as well as by LCMS, the crude reaction mixture was poured into 100 mL cold 1M KHSO$_4$, and extracted twice with 50 mL of CH$_2$Cl$_2$. The organic phase was dried, evaporated and purified by CombiFlash® (PE/EtOAC) to provide 1.1 grams of 100% pure product (62% yield).

Step 2: 2,3-dihydrobenzo[b][1,4]dioxine-6-sulfonyl chloride was stirred in dichloroethane with aluminium chloride for 10 minutes, and then 1-(methylsulfonyl)indoline was dropped in with stirring. The reaction was heated to 70° C. with KHSO$_4$ ion with stirring in a pressure ampoule overnight. The reaction mixture was evaporated and redissolved in EtOAc and then washed twice with 50 mL cold water and then with brine. The organic phase was dried over NaSO$_4$, evaporated and separated on CombiFlash® (EtOAc/PE) to provide 44.5 mg 99% pure product. (overall yield 8.15%).

Analysis: HPLC: 100% pure, Rt=8.54 minutes, as determined by the protocol in Example 1 above. MS–395.45 (calc.), 396.41 (MS+H+)(measured).

Example 10

Synthesis of N-(4-((2,3-dihydrobenzo[b][1,4]dioxin-6-yl)sulfonyl)-3-methylphenyl)-N-ethylmethanesulfonamide

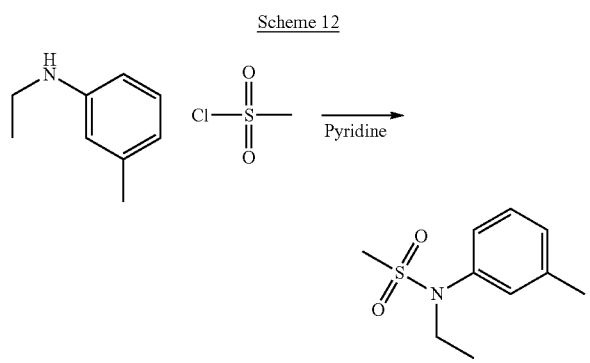

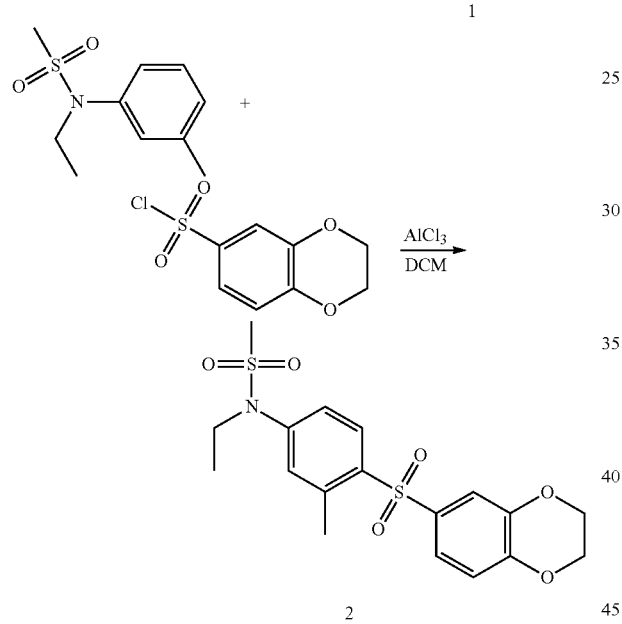

Reagents

| Reagent/raw material | MW (g/mole) | Quantity | moles |
|---|---|---|---|
| N-ethyl-3-methylaniline | 135.10 | 1 g | 7.3 mmol |
| methanesulfonyl chloride | 114.55 | 1 g | 8.87 mmol |
| N-ethyl-N-(m-tolyl)methanesulfonamide | 213.30 | 0.29 g | 1.38 mmol |
| 2,3-dihydrobenzo[b][1,4]dioxine-6-sulfonyl chloride | 234.66 | 0.5 g | 1 mmol |
| Aluminium chloride | 133.3 | 0.28 | 2.13 mmol |

Step 1: N-ethyl-3-methylaniline was dissolved in 5 mL dry pyridine, and methanesulfonyl chloride was dropped in. The reaction was stirred overnight at room temperature and an intense red color developed. When complete as determined by HPLC using the protocol of Example 1, as well as by LCMS, the crude reaction mixture was poured into 100 mL cold 1M KHSO$_4$, and extracted twice with 50 mL CH$_2$Cl$_2$. The organic phase was evaporated and purified by CombiFlash® (PE/EtOAC) to provide 1.3 grams of 100% pure product (82% yield).

Step 2: 2,3-dihydrobenzo[b][1,4]dioxine-6-sulfonyl chloride was stirred in dichloroethane with aluminium chloride for 10 minutes, and then N-ethyl-N-(m-tolyl)methanesulfonamide was dropped in with stirring. The reaction was heated to 70° C. with stirring in a pressure ampoule overnight. The reaction mixture was evaporated and redissolved in EtOAc and then washed twice with 50 mL cold water and then brine. The organic phase was dried over NaSO$_4$, evaporated and separated on CombiFlash® (EtOAc/PE) providing 23 mg, 95.38% pure product (overall yield 4%).

Analysis: HPLC: 95.38% pure, Rt=8.78 minutes, as determined by the protocol of Example 1 above. MS–411.49 (calc.), 412.31 (MS+H+)(measured).

Example 11

Synthesis of 1-(benzylsulfonyl)-5-((2,3-dihydrobenzo[b][1,4]dioxin-6-yl)sulfonyl)-2-methylindoline

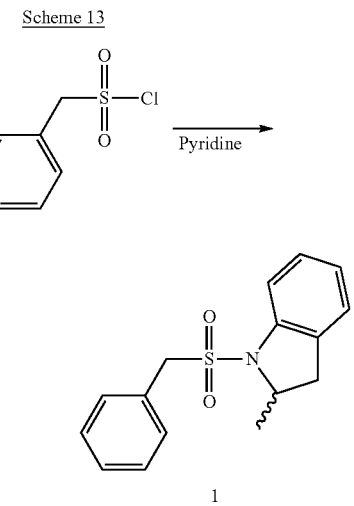

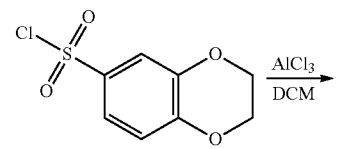

-continued

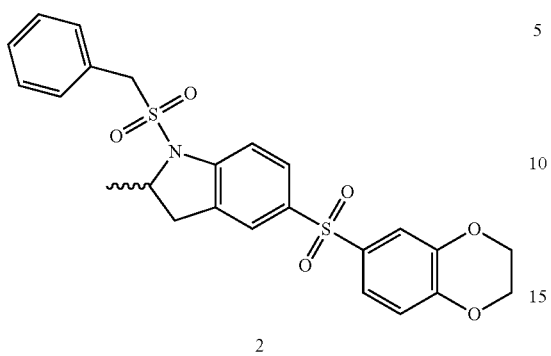

Reagents

| Reagent/raw material | MW (g/mole) | Quantity | moles |
|---|---|---|---|
| 2-methylindoline | 133.19 | 0.46 g | 3.5 mmol |
| phenylmethanesulfonyl chloride | 190.65 | 1 g | 5.2 mmol |
| 1-(benzylsulfonyl)-2-methylindoline | 287.38 | 4 g | 1.38 mmol |
| 2,3-dihydrobenzo[b][1,4]dioxine-6-sulfonyl chloride | 234.66 | 0.25 g | 1 mmol |
| Aluminium chloride | 133.3 | 0.28 g | 2.13 mmol |

Step 1: 2-methylindoline was dissolved in 5 mL dry pyridine, and phenylmethanesulfonyl chloride was dropped in. The reaction was stirred overnight at room temperature and an intense red color developed. When complete as determined by HPLC using the protocol of Example 1, as well as by LCMS, the crude reaction mixture was poured into 100 mL cold 1M KHSO$_4$, and extracted twice with 50 mL CH$_2$Cl$_2$. the organic phase was evaporated and purified by CombiFlash® (PE/EtOAC) to provide 0.46 g of 100% pure product (30.8% yield).

Step 2: 2,3-dihydrobenzo[b][1,4]dioxine-6-sulfonyl chloride was stirred in dichloroethane with aluminium chloride for 10 minutes, and then 1-(benzylsulfonyl)-2-methylindoline was dropped in with stirring. The reaction was heated to 70° C. with stirring in a pressure ampoule overnight. The reaction mixture was evaporated and redissolved in EtOAc and then washed twice with 50 mL of cold water and then with brine. The organic phase was dried over NaSO$_4$, evaporated and separated on CombiFlash® (EtoAc/PE) to provide 8 mg, 94% pure product (overall yield 14.1%).

Analysis: HPLC–94.6% pure, Rt=9.66 minutes, as determined by the protocol of Example 1 above. MS–485.57 (calc.), 486.34 (MS+H+)(measured).

Example 12

Synthesis of 5-((2,3-dihydrobenzo[b][1,4]dioxin-6-yl)sulfonyl)-2-(isobutylsulfonyl)isoindoline

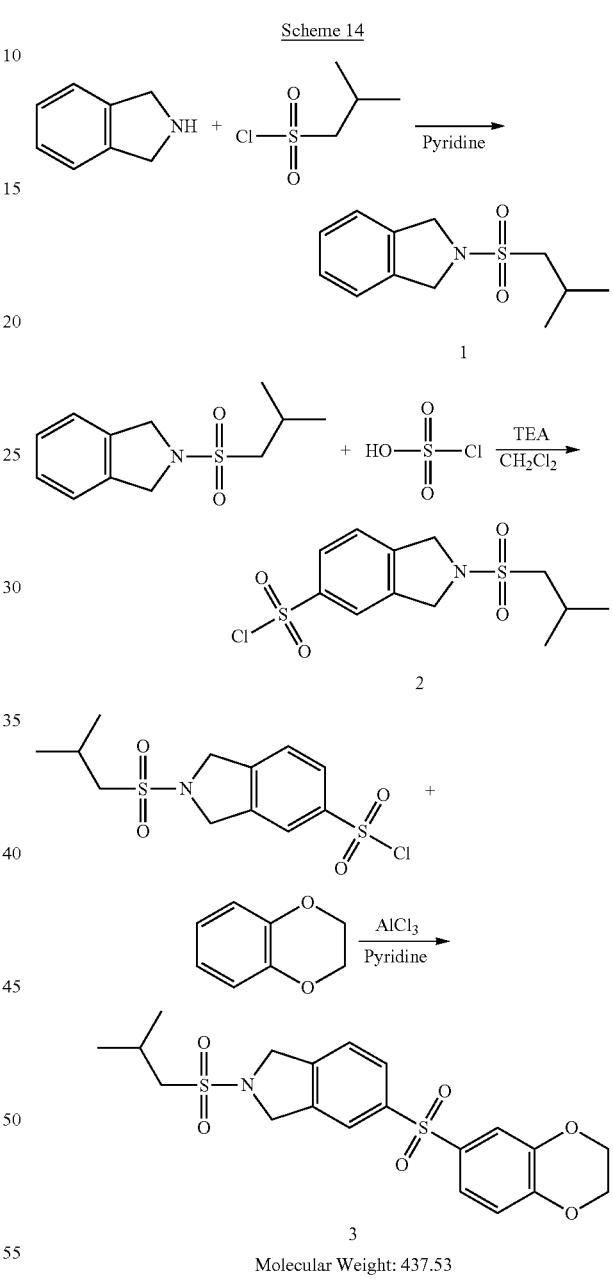

Reagents

| Reagent/raw material | MW (g/mole) | Quantity | moles |
|---|---|---|---|
| isoindoline | 119.16 | 0.5 g | 4.2 |
| 2-methylpropane-1-sulfonyl chloride | 156.63 | 0.98 g | 6.3 |
| 2-(isobutylsulfonyl)isoindoline | 239.33 | 0.45 g | 1.88 |

-continued

| Reagent/raw material | MW (g/mole) | Quantity | moles |
|---|---|---|---|
| sulfurochloridic acid | 116.52 | 5 mL | excess |
| 2-(isobutylsulfonyl)isoindoline-5-sulfonyl chloride | 337.84 | 0.41 g | 1.2 |
| 2,3-dihydrobenzo[b][1,4]dioxine | 136.15 | 0.215 g | 1.6 |
| AlCl₃ | 133 | 0.323 g | 2.4 |

Step 1: Isoindoline was dissolved in 5 mL dry pyridine, and 2-methylpropane-1-sulfonyl chloride chloride was dropped in. The reaction was stirred overnight at room temperature and an intense red color developed. When complete as determined by HPLC using the protocol of Example 1, as well as by LCMS, the crude reaction was poured into 100 mL cold 1M KHSO₄, and extracted twice with 50 mL CH₂Cl₂. The organic phase was evaporated and the evaporation residue was purified by CombiFlash® (PE/EtOAC) to provide 0.45 grams pure product (44.8% yield).

Step 2: 2-(isobutylsulfonyl)isoindoline was added to cooled chlorosulfonic acid with stirring. The reaction was allowed to warm to room temperature and then stirred for 6 hours. The reaction mixture was slowly and carefully dropped into stirred ice in water and stirred for 20 minutes. The product was extracted twice with 50 mL of CH₂Cl₂ and then washed twice with 50 mL cold water and finally with brine. The organic phase was dried and evaporated, and the product was pure enough for the next step (0.41 g, 100% pure, yield 64%).

Step 3: 2-(isobutylsulfonyl)isoindoline-5-sulfonyl chloride was stirred in dichloroethane with aluminium chloride for 10 minutes, and then 2,3-dihydrobenzo[b][1,4]dioxine was dropped in with stirring. The reaction was heated to 70° C. with stirring in a pressure ampoule for 1 hour. The reaction was evaporated and redissolved in EtOAc and then washed twice with 50 mL cold water and then with brine. The organic phase was dried, evaporated and separated on CombiFlash®. The final product eluted at 8/2 EtoAc/PE to provide 22.2 mg, 99% pure product.

Analysis: HPLC–99% pure, Rt=9.037 minutes, as determined by the protocol described in Example 1. MS–(ES+) Calcd. for C17H17NO6S2 437.53. found 438.45 (M+H).

Example 13

Synthesis of 5-((2,3-dihydrobenzo[b][1,4]dioxin-6-yl)sulfonyl)-1-(ethylsulfonyl)indoline Scheme 15

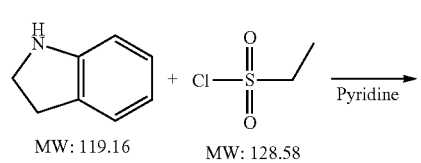

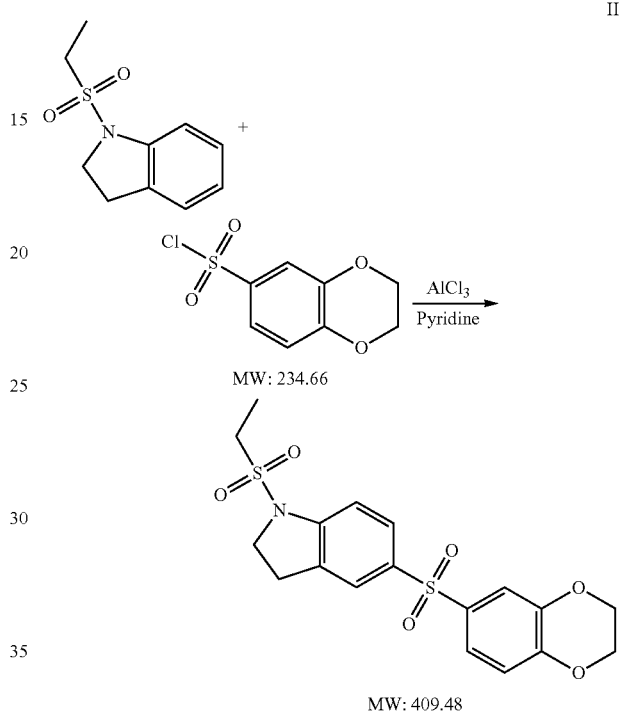

Reagents

| Reagent/raw material | MW (g/mole) | Quantity | moles | Mole ratio |
|---|---|---|---|---|
| indoline | 119.16 | 1.76 g | 14.72 mmol | 1 eq. |
| ethanesulfonyl chloride | 128.58 | 2.08 g | 16.91 mmol | 1.1 eq. |
| 1-(ethylsulfonyl)indoline | 211.28 | 800 mg | 3.77 mmol | 1.0 eq. |
| 2,3-dihydro-benzo[b][1,4]dioxine-6-sulfonyl chloride | 234.66 | 950 mg | 4.0 mmol | 1.05 eq. |
| Aluminium chloride | 133.3 | 1350 mg | 2.5 mmol | 2.5 eq. |
| 5-((2,3-dihydro-benzo[b][1,4]dioxin-6-yl)sulfonyl)-1-(ethylsulfonyl)indoline | 409.48 | | | |

Step I: Indoline was dissolved in 10 mL dry pyridine, and ethanesulfonyl chloride was dropped in 2 portions under N₂. The reaction was stirred overnight at room temperature and an intense red color developed. When the reaction was complete as determined by TLC (8/2 PE/EtOAC), the crude reaction mixture was poured into 100 mL cold 0.5M HCl, and extracted twice with 50 mL CH₂Cl₂. The organic phase was evaporated, and the evaporation residue was purified by passing through a silica plug (~100 g silica gel in large sinter glass). The product eluted in 7/3 PE/EtOAC, while all of the pink polar byproduct was retained on silica. The organic phase was dried on $Na_2SO_4$, evaporated and used for the next step without further purification (Product 800 mg, yield 26%).

Step II: 2,3-dihydrobenzo[b][1,4]dioxine-6-sulfonyl chloride was stirred in dichloroethane with aluminium chloride for 10 minutes, and then 1-(ethylsulfonyl)indoline was dropped in with stirring. The reaction was heated to 70° C. with stirring in a pressure ampoule for 1 hour. The reaction mixture was evaporated and redissolved in EtOAc and then washed twice with 50 mL cold water and then with brine. The organic phase dried, evaporated and separated on CombiFlash®. The final product eluted at 8/2 EtOAc/PE to provide 155 mg of 98.9% pure product (overall yield 2.6%).

Analysis: HPLC–98.9% pure, Rt=8.621 minutes, as determined by the protocol described in Example 1. MS–(ES+) Calcd. for C18H19NO6S2 409.07. found 410.45 (M+H).

Example 14

Synthesis of 5-((2,3-dihydrobenzo[b][1,4]dioxin-6-yl)sulfonyl)-2-(ethylsulfonyl)isoindoline

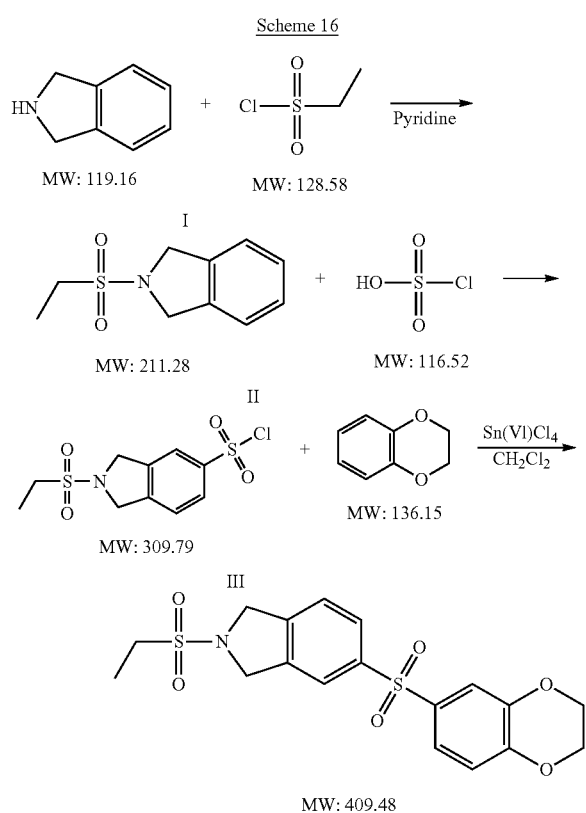

Reagents

| Reagent/raw material | MW (g/mole) | Quantity | moles | Mole ratio |
|---|---|---|---|---|
| Isoindoline | 119.16 | 1.00 g | 8.39 mmol | 1 eq. |
| ethanesulfonyl chloride | 128.58 | 1.13 g | 8.81 mmol | 1.05 eq. |
| 2-(ethylsulfonyl)iso- | 211.28 | Approx | 3.77 mmol | 1.0 eq. |
| indoline | | 800 mg | | |
| sulfurochloridic acid | 116.52 | 5 ml | excess | excess |
| 2-(ethylsulfonyl)iso-indoline-5-sulfonyl chloride | 309.79 | 500 mg | 1.61 mmol | 1.0 eq. |
| 2,3-dihydro-benzo[b][1,4]dioxine | 234.66 | 340 mg | 2.5 mmol | 1.5 eq. |
| Tin(IV) chloride | 260.25 | 420 mg | 1.61 mmol | 1.0 eq. |
| 5-((2,3-dihydro-benzo[b][1,4]dioxin-6-yl)sulfonyl)-2-(ethylsulfonyl)isoindoline | 409.48 | | | |

Step I: Isoindoline was dissolved in 10 mL dry pyridine, and ethanesulfonyl chloride was dropped in 2 portions under $N_2$. The reaction was stirred for two hours at room temperature and an intense red color developed. When the reaction was complete as determined by TLC (8/2 PE/EtOAC), the crude reaction mixture was poured into 100 mL cold 0.5M HCl, and extracted twice with 50 mL $CH_2Cl_2$. The organic phase was evaporated, and the evaporation residue was purified by passing through a silica plug (~100 g silica gel in large sinter glass). The product eluted in 7/3 PE/EtOAC, while all of the pink polar byproduct was retained on silica. The organic phase was dried on $Na_2SO_4$, evaporated and used for the next step without further purification (Product approximately 800 mg, yield 26%, HPLC Rt=7.796 minutes).

Step II: 2-(ethylsulfonyl)isoindoline was added to cooled chlorosulfonic acid with stirring. The reaction was allowed to warm to room temperature and stirred for 6 hours. The reaction mixture was slowly and carefully dropped into stirred ice in water and stirred for 20 minutes. The product was extracted twice with 50 mL $CH_2Cl_2$ and then washed twice with 50 mL cold water and finally with brine. The organic phase was dried and evaporated and was pure enough for the next step (500 mg, yield 19%).

Step III: 2-(ethylsulfonyl)isoindoline-5-sulfonyl chloride was stirred in dichloroethane with tin(IV) chloride for 10 minutes, and then 2,3-dihydrobenzo[b][1,4]dioxine was dropped in with stirring. The reaction was heated to 70° C. with stirring in a pressure ampoule for 1 hour. The reaction was evaporated and redissolved in EtOAc and then washed twice with 50 mL cold water and then brine. The organic phase was dried, evaporated and separated on CombiFlash®. The final product eluted at 8/2 EtOAc/PE to provide 7.7 mg of 94% pure product (overall yield 3%).

Analysis: HPLC–94% pure, Rt=8.331 minutes, as determined by the protocol of Example 1 above. MS–(ES+) Calcd. for C18H19NO6S2 409.48. found 410.51 (M+H).

Example 15

Synthesis of 5-((2,3-dihydrobenzo[b][1,4]dioxin-6-yl)sulfonyl)-1-(isopropylsulfonyl)indoline Scheme 17

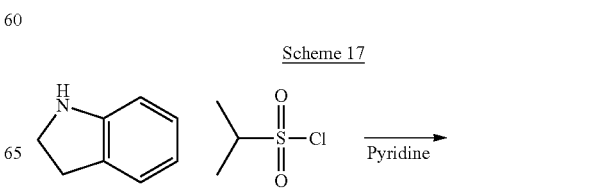

-continued

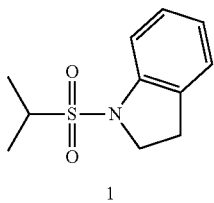

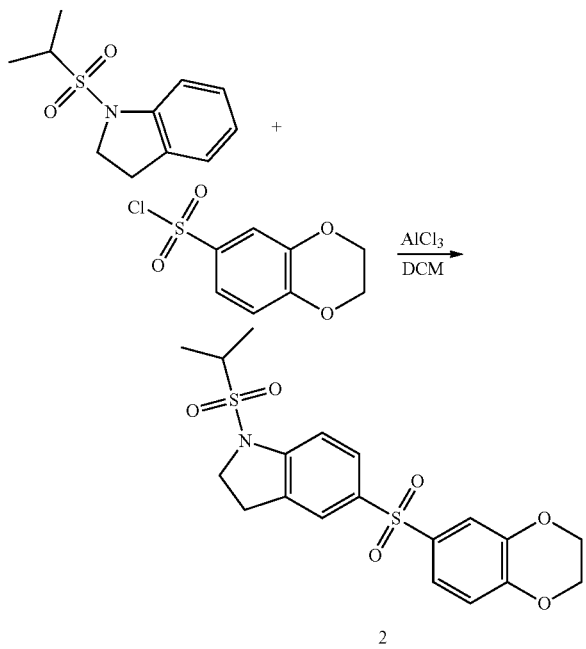

Reagents

| Reagent/raw material | MW (g/mole) | Quantity | moles |
|---|---|---|---|
| Indoline | 119 | 1.05 g | 8.7 mmol |
| propane-2-sulfonyl chloride | 142.60 | 0.72 g | 5 mmol |
| 1-(isopropylsulfonyl)indoline | 225.31 | 0.83 g | 3.688 mmol |
| 2,3-dihydrobenzo[b][1,4]dioxine-6-sulfonyl chloride | 234.66 | 0.66 g | 2.83 mmol |
| Aluminium chloride | 133.3 | 0.98 g | 7.37 mmol |

Step 1: Indoline was dissolved in 5 mL dry pyridine, and propane-2-sulfonyl chloride was dropped in. The reaction was stirred overnight at room temperature and an intense red color developed. When the reaction was complete as determined by HPLC using the protocol of Example 1, as well as by LCMS, the crude reaction mixture was poured into 100 mL cold 1M $KHSO_4$, and extracted twice with 50 mL $CH_2Cl_2$. The organic phase was evaporated and the evaporation residue was purified by CombiFlash® (PE/EtOAC) to provide 0.83 g of 100% pure product (73% yield).

Step 2: 2,3-dihydrobenzo[b][1,4]dioxine-6-sulfonyl chloride was stirred in dichloroethane with aluminium chloride for 10 minutes, and then 1-(isopropylsulfonyl)indoline was dropped in with stirring. The reaction was heated to 70° C. with stirring in a pressure ampoule overnight. The reaction was evaporated and redissolved in EtOAc and then washed twice with 50 mL cold water and then brine. The organic phase was dried over $NaSO_4$, evaporated and separated on CombiFlash®. The product eluted at 8/2 EtOAc/PE to provide 14.9 mg product (yield 14.1%).

Analysis: HPLC–100% pure, Rt=8.98 minutes, as determined by the protocol described in Example 1. MS–423.5 (calc.). found 424.48 (MS+H+).

Example 16

Synthesis of 5-((2,3-dihydrobenzo[b][1,4]dioxin-6-yl)sulfonyl)-1-(phenylsulfonyl)indoline Scheme 18

Reagents

| Reagent/raw material | MW (g/mole) | Quantity | moles |
|---|---|---|---|
| Indoline | 119 | 0.54 g | 4.5 mmol |
| benzenesulfonyl chloride | 176.62 | 1 g | 5.6 mmol |
| 1-(phenylsulfonyl)indolin | 259.32 | 0.5 g | 1.9 mmol |
| 2,3-dihydrobenzo[b][1,4]dioxine-6-sulfonyl chloride | 234.66 | 0.58 g | 2.47 mmol |
| Aluminium chloride | 133.3 | 0.51 g | 3.8 mmol |

Step 1: Indoline was dissolved in 5 mL dry pyridine, and benzenesulfonyl chloride was dropped in. The reaction was stirred overnight at room temperature and an intense red color developed. When the reaction was complete as determined by HPLC with the protocol described above, as well as by LCMS, the reaction mixture was poured into 100 mL cold 1M KHSO$_4$, and extracted twice with 50 mL CH$_2$Cl$_2$. The organic phase was evaporated and the evaporation residue was purified by CombiFlash® (PE/EtOAC) providing 1.05 g 100% pure product (68% yield).

Step 2: 2,3-dihydrobenzo[b][1,4]dioxine-6-sulfonyl chloride was stirred in dichloroethane with aluminium chloride for 10 minutes, and then 1-(phenylsulfonyl)indolin was dropped in with stirring. The reaction was heated to 70° C. with stirring in a pressure ampoule overnight. The reaction was evaporated and redissolved in EtOAc and then washed twice with 50 mL cold water and then brine. The organic phase was dried over NaSO$_4$, evaporated and separated on CombiFlash®. The final product eluted at 8/2 EtOAc/PE to provide 70 mg product (yield 80%).

Analysis: HPLC–100% pure, Rt=9.32 minutes, as determined by the protocol described in Example 1. MS–457.52 (calc.). found 458.39 (MS+H+).

Example 17

Synthesis of 5-((2,3-dihydrobenzo[b][1,4]dioxin-6-yl)sulfonyl)-2-(phenylsulfonyl)isoindoline Scheme 19

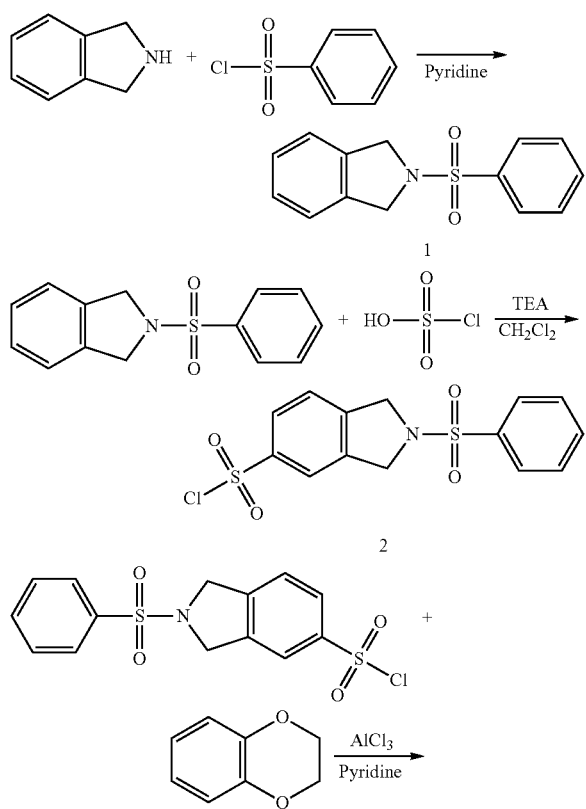

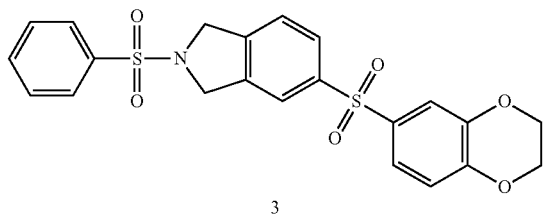

3

Reagents

| Reagent/raw material | MW (g/mole) | Quantity | moles |
|---|---|---|---|
| Isoindoline | 119.16 | 0.5 g | 4.2 |
| benzenesulfonyl chloride | 176.62 | 1.1 g | 6.3 |
| 2-(phenylsulfonyl)isoindoline | 259.32 | 0.54 g | 2 |
| sulfurochloridic acid | 116.52 | 5 mL | excess |
| 2-(phenylsulfonyl)isoindoline-5-sulfonyl chloride | 357.83 | 0.05 g | 0.139 |
| 2,3-dihydrobenzo[b][1,4]dioxine | 136.15 | 0.024 g | 0.18 |
| AlCl$_3$ | 133 | 0.037 | 0.27 |

Step 1: Isoindoline was dissolved in 5 mL dry pyridine, and benzenesulfonyl chloride was dropped in. The reaction was stirred overnight at room temperature and an intense red color developed. When complete as determined by HPLC using the protocol of Example 1, as well as by LCMS, the crude reaction mixture was poured into 100 mL cold 1M KHSO$_4$, and extracted twice with 50 mL CH$_2$Cl$_2$. The organic phase was evaporated and the evaporation residue was purified by CombiFlash® (PE/EtOAC) providing 1.1 g pure product (100% yield).

Step 2: 2-(phenylsulfonyl)isoindoline was added to cooled chlorosulfonic acid with stirring. The reaction was warmed to room temperature and stirred for 6 hours. The reaction mixture was slowly and carefully dropped into stirred ice in water and stirred for 20 minutes. The product was extracted twice with 50 mL CH$_2$Cl$_2$ and then washed twice with 50 mL cold water and finally with brine. The organic phase was dried, evaporated and the product was pure enough for the next step (100% pure, 0.05 g, yield 7%).

Step 3: 2-(phenylsulfonyl)isoindoline-5-sulfonyl chloride was stirred in dichloroethane with aluminium chloride for 10 minutes, and then 2,3-dihydrobenzo[b][1,4]dioxine was dropped in with stirring. The reaction was heated to 70° C. with stirring in a pressure ampoule for 1 hour. The reaction was evaporated and redissolved in EtOAc and then washed twice with 50 mL cold water and then brine. The organic phase was dried, evaporated and separated on CombiFlash®. The final product eluted at 8/2 EtOAc/PE providing 8.7 mg product (13.6% yield).

Analysis: HPLC–98.6% pure, Rt=9.21 minutes, as determined by the protocol of Example 1 above.

MS-(ES+) Calcd. for C17H17NO6S2: 457.52. found 458.33 (M+H).

Example 18

Synthesis of 5,5'-sulfonylbis(2-methyl-1-(methylsulfonyl)indoline)

Scheme 20

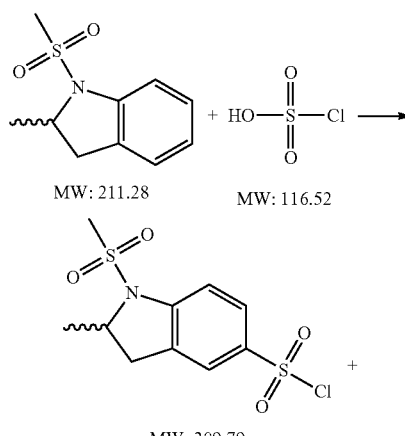

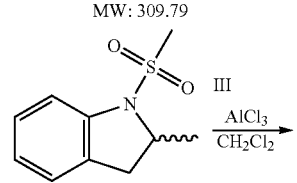

Reagents

| Reagent/raw material | MW (g/mole) | Quantity | moles | Mole ratio |
|---|---|---|---|---|
| 2-methylindoline | 133.19 | 1 g | 7.5 mmol | 1 eq. |
| methanesulfonyl chloride | 114.55 | 1.04 g | 9.0 mmol | 1.5 eq. |

-continued

| Reagent/raw material | MW (g/mole) | Quantity | moles | Mole ratio |
|---|---|---|---|---|
| 2-methyl-1-(methylsulfonyl)indoline | 211.28 | 276 mg | 1.3 mmol | 1.2 eq. |
| sulfurochloridic acid | 116.52 | 5 mL | excess | excess |
| 2-methyl-1-(methylsulfonyl)indoline-5-sulfonyl chloride | 309.79 | 450 mg | 1.45 mmol | 1 eq. |
| Aluminium chloride | 133.3 | 500 mg | 3.75 mmol | 2.5 eq. |
| 5,5'-sulfonylbis(2-methyl-1-(methylsulfonyl)indoline) | 484.61 | | | |

Step I: 2-methylindoline was dissolved in 5 mL dry pyridine, and methanesulfonyl chloride was dropped in 2 portions under $N_2$. The reaction was stirred for 2 hours at room temperature and an intense red color developed. When complete as determined by HPLC (product Rt=8.51 minutes, starting material Rt=4.18 minutes) using the protocol described in Example 1, as well as by TLC (8/2 PE/EtOAC), the crude reaction mixture was poured into 100 mL cold 0.5M HCl, and extracted twice with 50 mL $CH_2Cl_2$. The organic phase was evaporated and the evaporation residue was purified by passing through a silica plug (~100 g silica gel in large sinter glass). The product eluted in 7/3 PE/EtOAC, while all of the pink polar byproduct was retained on silica. The organic phase was dried on $Na_2SO_4$, evaporated and used for the next step without further purification (Product 100% pure, 455 mg, yield ~30%).

Step II: 2-methyl-1-(methylsulfonyl)indoline was added to cooled chlorosulfonic acid with stirring. The reaction was allowed to warm to room temperature and stirred for 6 hours. The reaction mixture was slowly and carefully dropped into stirred ice in water and stirred for 20 minutes. The product was extracted twice with 50 mL $CH_2Cl_2$ and then washed twice with 50 mL cold water and then with brine. The organic phase was dried, evaporated and the product was pure enough for the next step (87% pure, Rt=9.152 minutes, 450 mg, yield 44%).

Step III: 2-methyl-1-(methylsulfonyl)indoline-5-sulfonyl chloride was stirred in dichloroethane with aluminium chloride for 10 minutes, and then 2-methyl-1-(methylsulfonyl) indoline was dropped in with stirring. The reaction was heated to 70° C. with stirring in a pressure ampoule for 1 hour. The reaction mixture was evaporated and redissolved in EtOAc and then washed twice with 50 mL cold water and then with brine. The organic phase was dried, evaporated and separated on CombiFlash®. The final product eluted at 8/2 EtoAc/PE to provide 178 mg of 100% pure product (overall yield 11%).

Analysis: $^1$H-NMR 300 MHz, (CDCl3) δ 1.31 (CH3, s), 1.34 (CH3, s), 2.79 (4H, dd), 3.08 (6H, s), 3.54 (4H, dd), 4.58 (2H, dd), 7.41 (2H, d), 7.79 (2H, d), 7.81 (2H, s).

HPLC-100% pure, Rt=8.872 minutes, as determined by the protocol of Example 1 above.

MS-(ES+) Calcd. for C20H24N2O6S3 484.61. found 485.47 (M+H).

Example 19

Synthesis of 5-((2,3-dihydrobenzo[b][1,4]dioxin-6-yl)sulfonyl)-3-methyl-1-(methylsulfonyl)-1H-indole

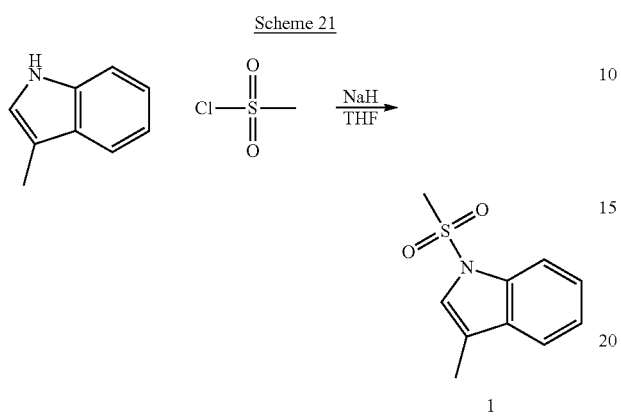

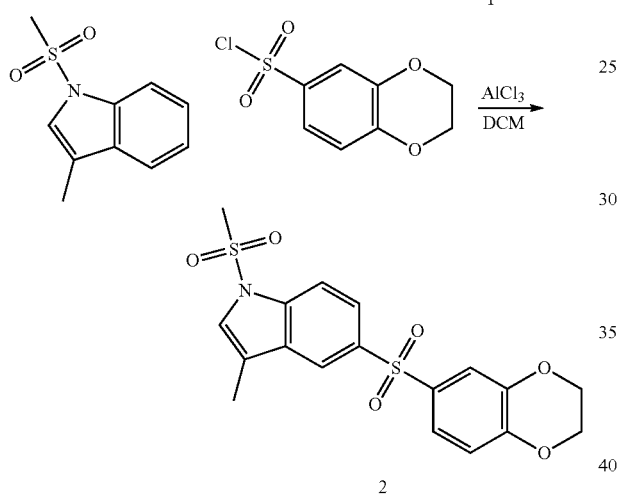

Reagents

| Reagent/raw material | MW (g/mole) | Quantity | moles |
|---|---|---|---|
| 3-methyl-1H-indole | 131.17 | 1 g | 7.6 mmol |
| methanesulfonyl chloride | 114.55 | 0.95 g | 8.4 mmol |
| sodium hydride (60% in mineral oil) | 24 | 0.36 g | 15 mmol |
| 3-methyl-1-(methylsulfonyl)-1H-indole | 209.26 | 0.4 g | 1.9 mmol |
| 2,3-dihydrobenzo[b][1,4]dioxine-6-sulfonyl chloride | 234.66 | 0.4 g | 1.73 mmol |
| Aluminium chloride | 133.3 | 0.5 g | 3.8 mmol |

Step 1: 3-methyl-1H-indole was dissolved in dry THF (10 mL), which was then added to a stirred suspension of NaH (60% in mineral oil) in dry THF (15 mL). The mixture was allowed to proceed at room temperature for 60 minutes to obtain the desired anion. Then methanesulfonyl chloride was dropped in and the reaction mixture was stirred overnight at room temperature. When complete, as determined by HPLC and LCMS, THF was evaporated and the crude reaction mixture was dissolved in EA and washed with water and brine. The organic phase was evaporated, and the evaporation residue was purified by CombiFlash®, RP-C-18, (20%-80% $H_2O$) to provide 0.4 g of 100% pure product (25% yield).

Step 2: 2,3-dihydrobenzo[b][1,4]dioxine-6-sulfonyl chloride was stirred in dichloroethane with aluminium chloride for 10 minutes, and then 3-methyl-1-(methylsulfonyl)-1H-indole was dropped in with stirring. The reaction was heated to 70° C. with stirring in a pressure ampoule overnight. The reaction was evaporated and redissolved in EtOAc and then washed twice with 50 mL cold water and then brine. The organic phase was dried over NaSO4, evaporated and separated on CombiFlash®. The final product eluted at 8/2 EtOAc/PE to provide 6 mg of 94% pure product (yield 0.9%).

Analysis: HPLC: 93.7% pure, Rt=9.085 minutes, as determined by the protocol described in Example 1. MS–407.46 (calc.), 408.33 (MS+H+)(measured).

Example 20

Synthesis of 5-((4-methoxyphenyl)sulfonyl)-1-(methylsulfonyl)indoline

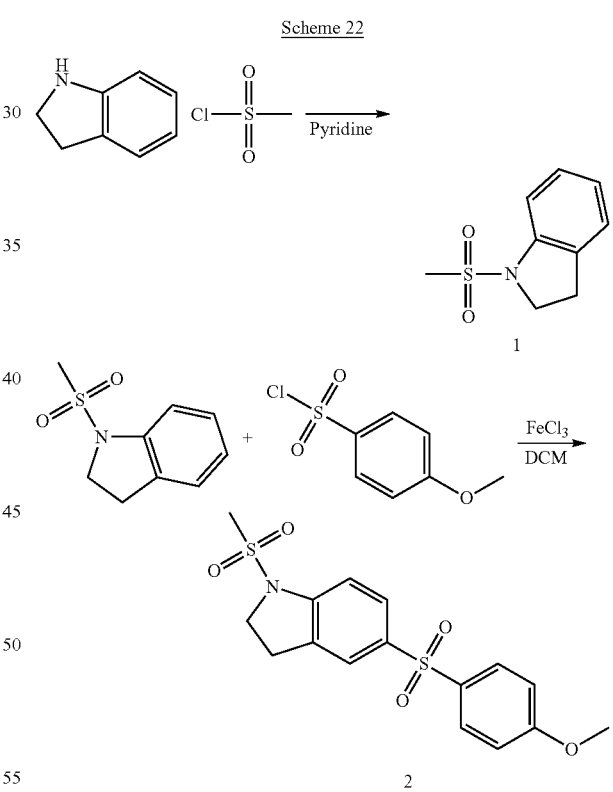

Molecular Weight: 367.44

Reagents Table

| Reagent/raw material | MW (gr/mole) | Quantity | moles |
|---|---|---|---|
| Indoline | 119.16 | 2 g | 16.7 mmol |
| methanesulfonyl chloride | 114.55 | 2.86 g | 25 mmol |

109

-continued

| Reagent/raw material | MW (gr/mole) | Quantity | moles |
|---|---|---|---|
| 1-(methylsulfonyl)indoline | 197.25 | 0.5 g | 2.5 mmol |
| 4-methoxybenzene-1-sulfonyl chloride | 206.65 | 0.43 g | 2.11 mmol |
| FeCl$_3$ | 126.75 | 0.8 | 6.2 mmol |

Procedure:

Synthesis of 1: Indoline was dissolved in 5 ml dry pyridine, and methanesulfonyl chloride was added. Reaction stirred for overnight at RT, intense red color developed. When complete by HPLC and LCMS, solvent was evaporated, crude reaction mixture was dissolved in EA and washed with HCl 1N, water and brine. Organic phase was evaporated and to give 3.05 g product 100% pure, (96% yield)

Synthesis of 2: 4-methoxybenzene-1-sulfonyl chloride was stirred in dichloromethane with FeCl3 for 10 min, and then 1-(methylsulfonyl)indoline was added in with stirring. Reaction mixture was stirred at rt for overnight. DCM was evaporated and redissolved in EtOAc and then washed with 2*50 ml cold water and brine. Organic phase dried over NaSO4, evaporated and purified on CombiFlash. Product eluted at EtoAc/PE, 142 mg, 96% pure, 18.3% yield. Analysis: HPLC: rt-7.72 min 95.9%; MS−367.44 (calc.), 368.4 (MS+H+)

Example 21

Synthesis of 5-((3,4-dimethoxyphenyl)sulfonyl)-1-(methylsulfonyl)indoline

Scheme 23

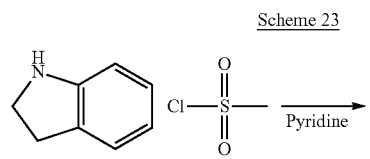

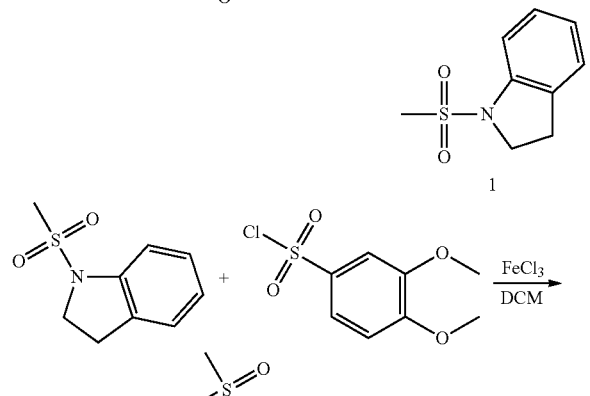

110

Reagents Table

| Reagent/raw material | MW (gr/mole) | Quantity | moles |
|---|---|---|---|
| Indoline | 119.16 | 2 g | 16.7 mmol |
| methanesulfonyl chloride | 114.55 | 2.86 g | 25 mmol |
| 1-(methylsulfonyl)indoline | 197.25 | 0.406 g | 2.06 mmol |
| 3,4-dimethoxybenzene-1-sulfonyl chloride | 236.67 | 0.48 g | 2.06 mmol |
| FeCl$_3$ | 126.75 | 0.78 | 6.18 mmol |

Procedure:

Synthesis of 1: Indoline was dissolved in 5 ml dry pyridine, and methanesulfonyl chloride was added. Reaction stirred for overnight at RT, intense red color developed. When complete by HPLC and LCMS, solvent was evaporated, crude reaction mixture was dissolved in EA and washed with HCl 1N, water and brine. Organic phase was evaporated and to give 3.05 g product 100% pure, (96% yield)

Synthesis of 2: 3,4-dimethoxybenzene-1-sulfonyl chloride was stirred in dichloromethane with FeCl3 for 10 min, and then 1-(methylsulfonyl)indoline was added in with stirring. Reaction mixture was stirred at rt 012 for overnight. DCM was evaporated and redissolved in EtOAc and then washed with 2*50 ml cold water and brine. Organic phase dried over NaSO4, evaporated and purified on CombiFlash. Product eluted at EtoAc/PE, 133 mg, 97.48% pure, 16.7% yield. Analysis: HPLC: rt-7.359 min 97.48%; MS−397.4 (calc.), 398.52 (MS+H+)

Example 22

Synthesis of 5-((2,3-dihydrobenzo[b][1,4]dioxin-6-yl)sulfonyl)-1-((2-(trifluoromethyl)phenyl)sulfonyl)indoline Scheme 24

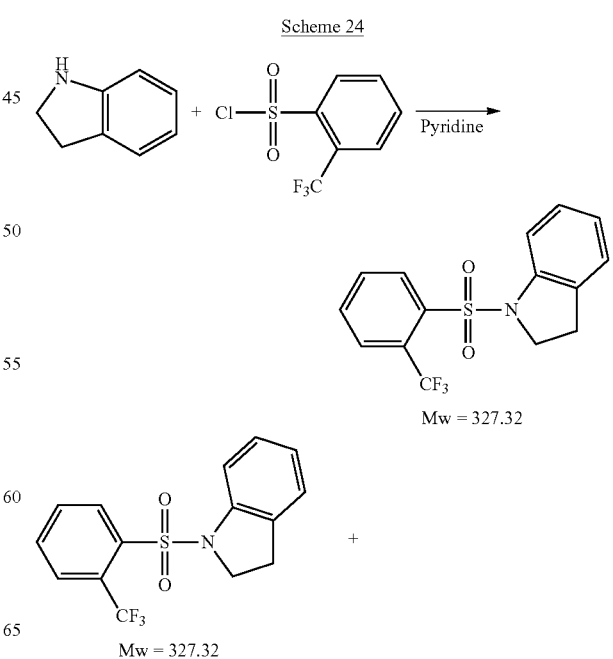

-continued

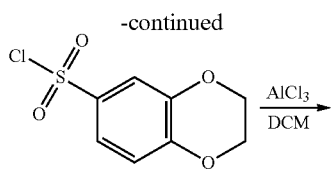

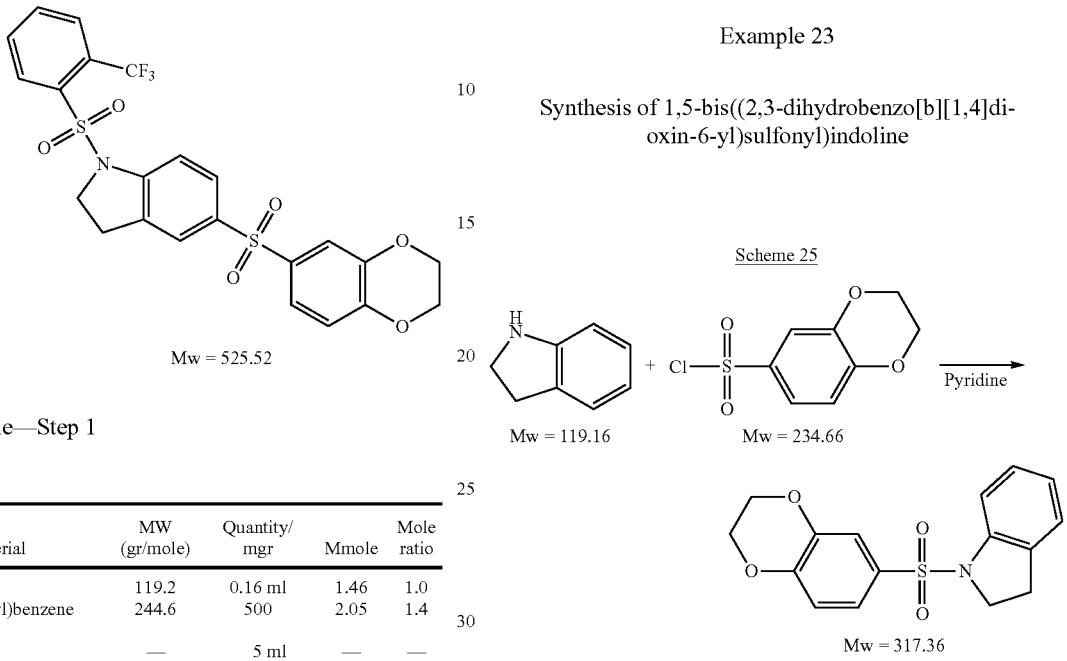

Mw = 525.52

Reagents Table—Step 1

| Reagent/raw material | MW (gr/mole) | Quantity/ mgr | Mmole | Mole ratio |
|---|---|---|---|---|
| Indoline | 119.2 | 0.16 ml | 1.46 | 1.0 |
| 2-(Trifluoromethyl)benzene sulfonyl chloride | 244.6 | 500 | 2.05 | 1.4 |
| Pyridine | — | 5 ml | — | — |

Procedure:

Indoline was dissolved in dry pyridine. 2-(Trifluoromethyl)benzene sulfonyl chloride was added dropwise and the reaction mixture was stirred overnight at rt. Intense red color appeared during the reaction. Monitoring by HPLC and LCMS indicated that the reaction was completed. The solvent was evaporated under reduced pressure, then HCl 1N solution and EtOAc were added. The organic layer was separated and the aqueous phase was extracted twice with EtOAc. The combined organic phase was dried over Na2SO4 and the solvent was evaporated under reduced pressure to yield the pure product: 467 mg, 96% yield.

Reagents Table—Step 2

| Reagent/raw material | MW (gr/mole) | Quantity/ mgr | Mmole | Mole ratio |
|---|---|---|---|---|
| 1-Trifluoromethylphenylsulfonyl indoline | 327.32 | 467 | 1.4 | 1.0 |
| 2,3-Dihydrobenzo[b][1,4]dioxine-6-sulfonyl chloride | 234.66 | 394 | 1.7 | 1.2 |
| Aluminium chloride | 133.3 | 187 | 1.4 | 1.0 |
| DCM | — | 15 ml | — | — |

Procedure:

2,3-Dihydrobenzo[b][1,4]dioxine-6-sulfonyl chloride was stirred in DCM with aluminium chloride for 10 min, and then 1-Trifluoromethylphenylsulfonyl indoline was added dropwise. The reaction was heated to 70° C. in pressure ampoule overnight. The solvent was evaporated and redissolved in EtOAc and then washed twice with cold water and brine. The combined organic phase was dried over Na2SO4 and the solvent was evaporated under reduced pressure. The crude solid obtained was purified by combi flash column to give the pure product as a white solid: 9 mg, 90% purity, 1.2% yield. Analysis: HPLC–90% purity, 9.32 min.

MS–(ES+) Calcd. for C23H18F3NO6S2 525.52. found 526.51 (MH+).

Example 23

Synthesis of 1,5-bis((2,3-dihydrobenzo[b][1,4]dioxin-6-yl)sulfonyl)indoline

Scheme 25

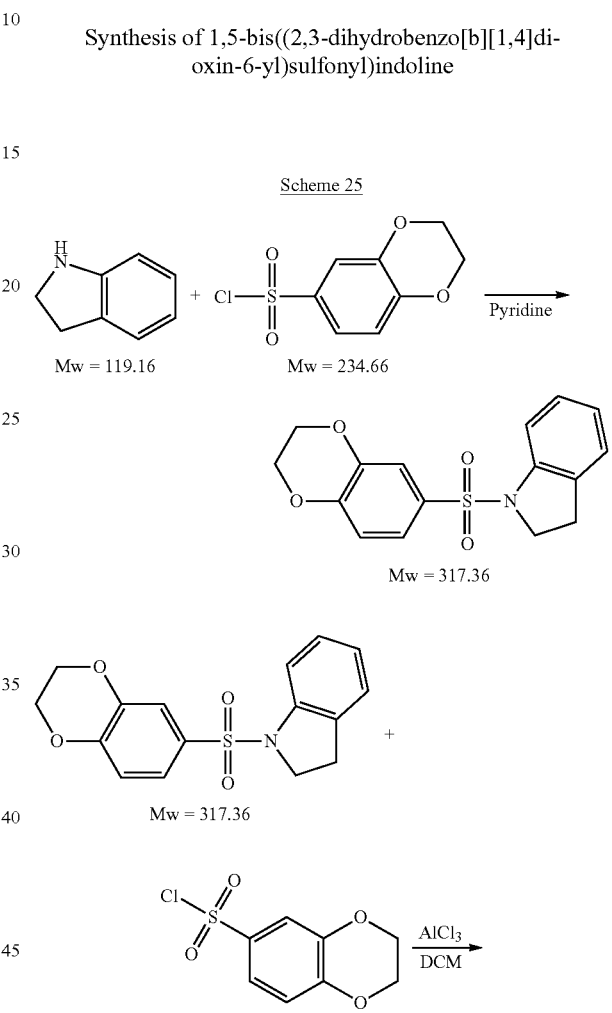

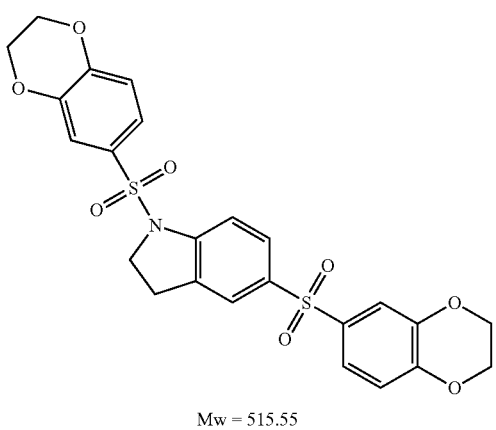

Mw = 515.55

Reagents Table—Step 1

| Reagent/raw material | MW (gr/mole) | Quantity/ mgr | Mmole | Mole ratio |
|---|---|---|---|---|
| Indoline | 119.2 | 0.19 ml | 1.7 | 1.0 |
| 2,3-dihydrobenzo[b][1,4]dioxine-6-sulfonyl chloride | 234.6 | 563 | 2.4 | 1.4 |
| Pyridine | — | 5 ml | — | — |

Procedure:

Indoline was dissolved in dry pyridine. 2,3-dihydrobenzo[b][1,4]dioxine-6-sulfonyl chloride was added dropwise and the reaction mixture was stirred overnight at rt. Intense red color appeared during the reaction. Monitoring by HPLC and LCMS indicated that the reaction was completed. The solvent was evaporated under reduced pressure, then HCl 1N solution and EtOAc were added. The organic layer was separated and the aqueous phase was extracted twice with EtOAc. The combined organic phase was dried over Na2SO4 and the solvent was evaporated under reduced pressure to yield the pure product: 463 mg, 86% yield.

Reagents Table—Step 2

| Reagent/raw material | MW (gr/mole) | Quantity/ mgr | Mmole | Mole ratio |
|---|---|---|---|---|
| 1-((2,3-dihydrobenzo[b][1,4]dioxin-6-yl)sulfonyl)indoline | 317.36 | 463 | 1.4 | 1.0 |
| 2,3-Dihydrobenzo[b][1,4]dioxine-6-sulfonyl chloride | 234.66 | 410 | 1.7 | 1.2 |
| Aluminium chloride | 133.3 | 290 | 2.2 | 1.5 |
| DCM | — | 15 ml | — | — |

Procedure:

2,3-Dihydrobenzo[b][1,4]dioxine-6-sulfonyl chloride was stirred in DCM with aluminium chloride for 10 min, and then 1-((2,3-dihydrobenzo[b][1,4]dioxin-6-yl)sulfonyl)indoline was added dropwise. The reaction was heated to 700 C in pressure ampoule overnight. The solvent was evaporated and redissolved in EtOAc and then washed twice with cold water and brine. The combined organic phase was dried over Na2SO4 and the solvent was evaporated under reduced pressure. The crude solid obtained was purified by combi flash column to give the pure product as a white solid: 150 mg, 97% purity, 20% yield. Analysis: HPLC–97% purity, 8.99 min. MS–(ES+) Calcd. for C24H21NO8S2 515.55. found 516.58 (MH+).

Example 24

Synthesis of 5-((2,3-dihydrobenzo[b][1,4]dioxin-6-yl)sulfonyl)-1-(m-tolylsulfonyl)indoline Scheme 26

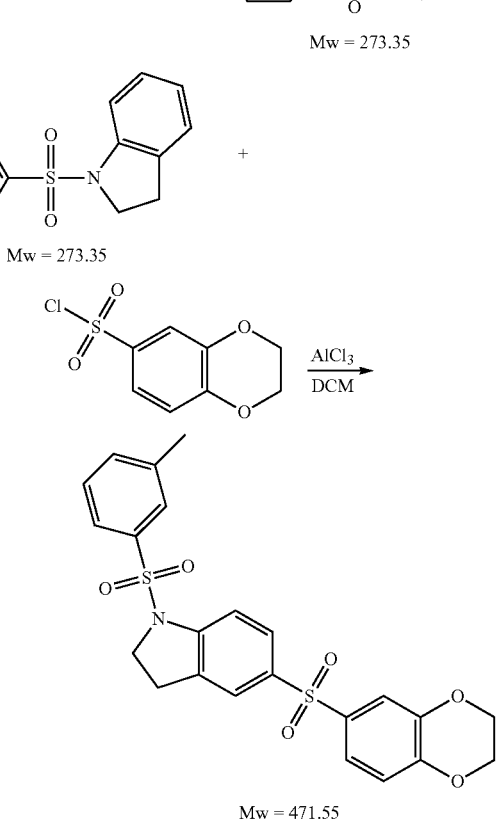

Reagents Table—Step 1

| Reagent/raw material | MW (gr/mole) | Quantity/ mgr | Mmole | Mole ratio |
|---|---|---|---|---|
| Indoline | 119.2 | 0.19 ml | 1.7 | 1.0 |
| 3-Methylbenzene-1-sulfonyl chloride | 190.65 | 458 | 2.4 | 1.4 |
| Pyridine | — | 5 ml | — | — |

Procedure:

Indoline was dissolved in dry pyridine. 3-Methylbenzene-1-sulfonyl chloride was added dropwise and the reaction mixture was stirred overnight at rt. Intense red color appeared during the reaction. Monitoring by HPLC and LCMS indicated that the reaction was completed. The solvent was evaporated under reduced pressure, then HCl 1N solution and EtOAc were added. The organic layer was separated and the aqueous phase was extracted twice with EtOAc. The combined organic phase was dried over $Na_2SO_4$ and the solvent was evaporated under reduced pressure to yield the pure product as a pink solid: 464 mg, 100% yield.

Reagents Table—Step 2

| Reagent/raw material | MW (gr/mole) | Quantity/ mgr | Mmole | Mole ratio |
|---|---|---|---|---|
| 1-(m-tolylsulfonyl)indoline | 273.3 | 464 | 1.7 | 1.0 |
| 2,3-Dihydrobenzo[b][1,4]dioxine-6-sulfonyl chloride | 234.6 | 477 | 2.0 | 1.2 |
| Aluminium chloride | 133.3 | 332 | 2.5 | 1.5 |
| DCM | — | 15 ml | — | — |

Procedure:

2,3-Dihydrobenzo[b][1,4]dioxine-6-sulfonyl chloride was stirred in DCM with aluminium chloride for 10 min, and then 1-(m-tolylsulfonyl)indoline was added dropwise. The reaction was heated to 700 C in pressure ampoule overnight. The solvent was evaporated and redissolved in EtOAc and then washed twice with cold water and brine. The combined organic phase was dried over $Na_2SO_4$ and the solvent was evaporated under reduced pressure. The crude solid obtained was purified by combi flash column to give the pure product as a white solid: 190 mg, 100% purity, 24% yield. Analysis: HPLC–100% purity, 9.34 min. MS–(ES+) Calcd. for C23H21NO6S2 471.55. found 472.55 (MH+).

Example 25

Synthesis of 5-((2,3-dihydrobenzo[b][1,4]dioxin-6-yl)sulfonyl)-4,6-difluoro-1-(methylsulfonyl)indoline Scheme 27

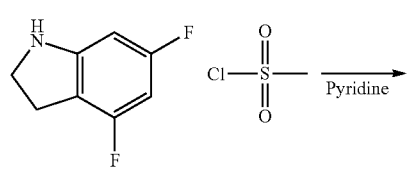

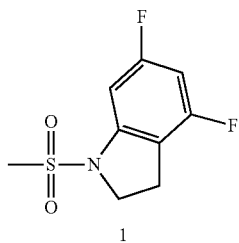

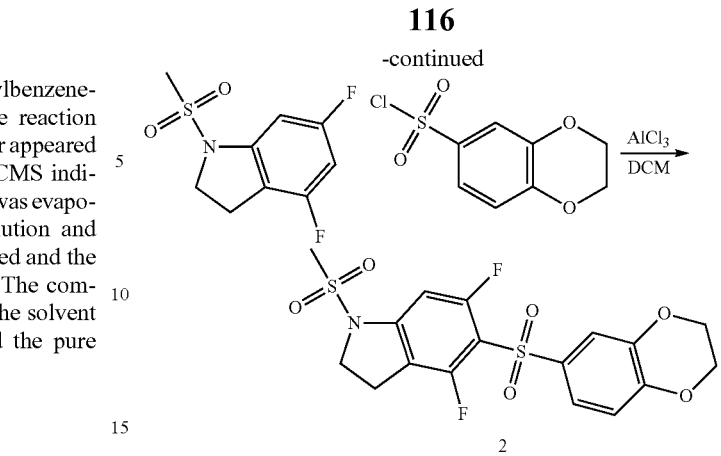

Reagents Table

| Reagent/raw material | MW (gr/mole) | Quantity | moles |
|---|---|---|---|
| 4,6-difluoroindoline | 155.14 | 0.5 g | 3.2 mmol |
| methanesulfonyl chloride | 114.55 | 0.44 g | 3.87 mmol |
| 4,6-difluoro-1-(methylsulfonyl)indoline | 233.24 | 0.572 g | 2.44 mmol |
| 2,3-dihydrobenzo[b][1,4]dioxine-6-sulfonyl chloride | 234.66 | 0.69 g | 2.94 mmol |
| Aluminium chloride | 133.3 | 0.979 | 7.36 mmol |

Procedure:

Synthesis of 1: 4,6-difluoroindoline was dissolved in 5 ml dry pyridine, and methanesulfonyl chloride was added. Reaction mixture was stirred for overnight at RT, intense red color developed. When complete by HPLC and LCMS, solvent was evaporated, and crude was dissolved in EA and washed with HCl 1N, water and brine. Organic phase was evaporated and purified by CombiFlash (PE/EtOAC) yield 0.522 g product 100% pure, (69% yield)

Synthesis of 2: 2,3-dihydrobenzo[b][1,4]dioxine-6-sulfonyl chloride was stirred in dichloromethane with aluminium chloride for 10 min, and then 4,6-difluoro-1-(methylsulfonyl) indoline was added in with stirring. Reaction mixture was heated to 700 C in pressure ampoule for overnight. DCM was evaporated and crude was redissolved in EtOAc and then washed with 2*50 ml cold water and brine. Organic phase dried over $Na_2SO_4$, evaporated and purified on CombiFlash. Product eluted at EtoAc/PE, 21.4 mg, 96% pure, 2% yield.

Analysis: HPLC: rt-8.40 min 96%. MS–431.43 (calc.), 432.43 (MS+H+).

Example 26

Synthesis of 1-(cyclopropylsulfonyl)-5-((2,3-dihydrobenzo[b][1,4]dioxin-6-yl)sulfonyl)indoline Scheme 28

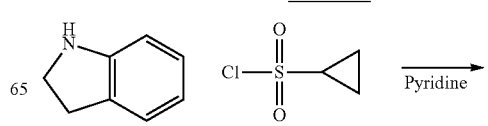

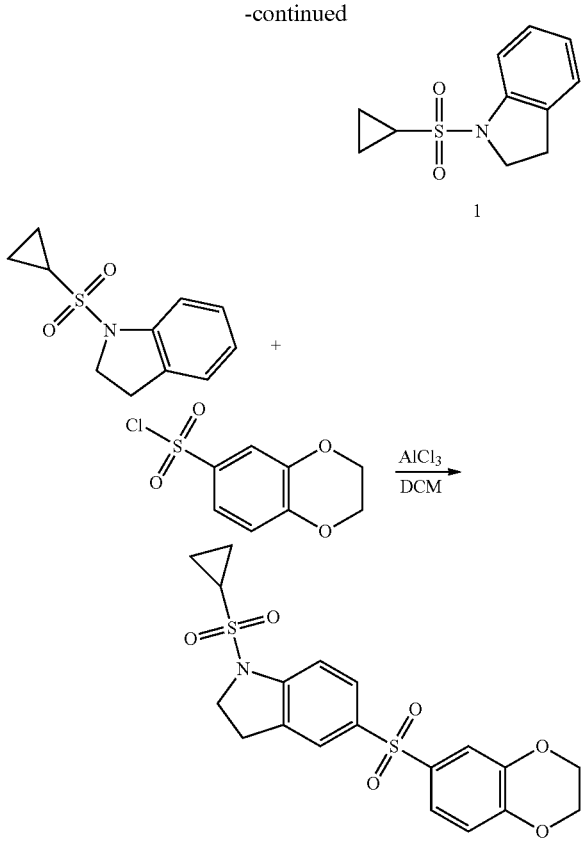

Analysis: HPLC: rt-8.37 min 100%. MS−421.49 (calc.), 422.43 (MS+H⁺)

Example 27

Synthesis of 5-((2,3-dihydrobenzo[α][1,4]dioxin-6-yl)sulfonyl)-1-((3-fluorophenyl)sulfonyl)indoline

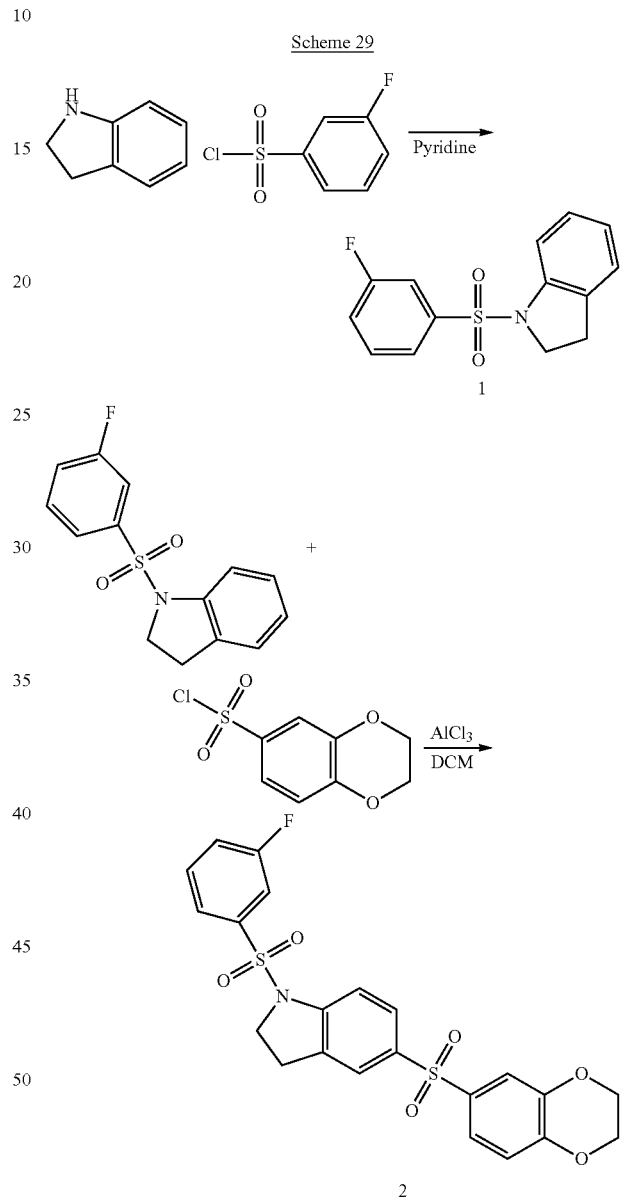

Reagents Table

| Reagent/raw material | MW (gr/mole) | Quantity | moles |
|---|---|---|---|
| Indoline | 119.16 | 0.85 g | 7.1 mmol |
| cyclopropanesulfonyl chloride | 140.59 | 1 g | 7.1 mmol |
| 1-(cyclopropylsulfonyl)indoline | 223.29 | 0.35 g | 1.56 mmol |
| 2,3-dihydrobenzo[b][1,4]dioxine-6-sulfonyl chloride | 234.66 | 0.44 g | 1.88 mmol |
| Aluminium chloride | 133.3 | 0.62 | 4.7 mmol |

Procedure:

Synthesis of 1: Indoline was dissolved in 5 ml dry pyridine, and cyclopropanesulfonyl chloride was added. Reaction mixture was stirred for overnight at RT, intense red color developed. When complete by HPLC and LCMS, solvent was evaporated, and crude was dissolved in EA and washed with HCl 1N, water and brine. Organic phase was evaporated, residue was purified by CombiFlash (PE/EtOAC) yield Product 100% pure, 0.088 g, (22.4% yield)

Synthesis of 2: 2,3-dihydrobenzo[b][1,4]dioxine-6-sulfonyl chloride was stirred in dichloromethane with aluminium chloride for 10 min, and then 1-(cyclopropylsulfonyl)indoline added in with stirring. Reaction mixture was heated to 700 C in pressure ampoule for overnight. DCM was evaporated and redissolved in EtOAc and then washed with 2*50 ml cold water and brine. Organic phase dried over Na₂SO₄, evaporated and purified on CombiFlash. Product eluted at EtOAc/PE, 88.4 mg, 100% pure. yield 13.4%

Reagents Table

| Reagent/raw material | MW (gr/mole) | Quantity | moles |
|---|---|---|---|
| Indoline | 119.16 | 130 g | 1.1 mmol |
| 3-fluorobenzene-1-sulfonyl chloride | 194.61 | 0.3 g | 1.5 mmol |
| 1-((3-fluorophenyl)sulfonyl)indoline | 277.31 | 0.327 g | 1.18 mmol |

| Reagent/raw material | MW (gr/mole) | Quantity | moles |
|---|---|---|---|
| 2,3-dihydrobenzo[b][1,4]dioxine-6-sulfonyl chloride | 234.66 | 0.33 g | 1.41 mmol |
| Aluminium chloride | 133.3 | 0.47 | 3.5 mmol |

Procedure:

Synthesis of 1: Indoline was dissolved in 5 ml dry pyridine, and 3-fluorobenzene-1-sulfonyl chloride was added. Reaction stirred for overnight at RT, intense red color developed. When complete by HPLC and LCMS, solvent was evaporated, crude reaction mixture was dissolved in EA and washed with HCl 1N, water and brine. Organic phase was evaporated and purified by CombiFlash (PE/EtOAC) yield 0.325 g product 100% pure, (100%% yield)

Synthesis of 2: 2,3-dihydrobenzo[b][1,4]dioxine-6-sulfonyl chloride was stirred in dichloromethane with aluminium chloride for 10 min, and then 1-((3-fluorophenyl)sulfonyl)indoline was added in with stirring. Reaction mixture was heated to 700 C in pressure ampoule for overnight. DCM was evaporated and redissolved in EtOAc and then washed with 2*50 ml cold water and brine. Organic phase dried over $Na_2SO_4$, evaporated and purified on CombiFlash. Product eluted at EtoAc/PE, 24 mg, 100% pure, 4.2% yield.

Analysis: HPLC (method Sasha 220 254 280) rt-9.13 min 100%. MS–475.51 (calc.), 476.46 (MS+H+)

Example 28

Synthesis of 1-((2,6-difluorophenyl)sulfonyl)-5-((2,3-dihydrobenzo[b][1,4]dioxin-6-yl)sulfonyl)indoline

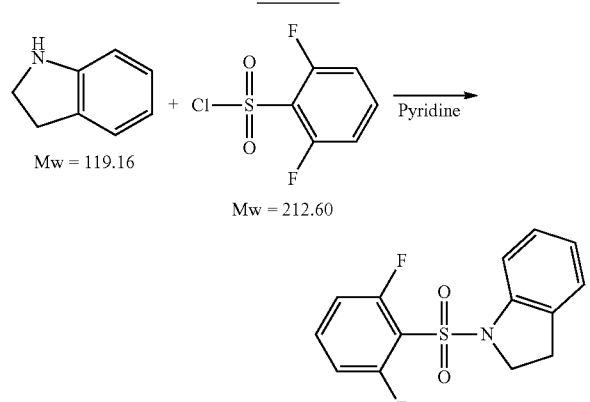

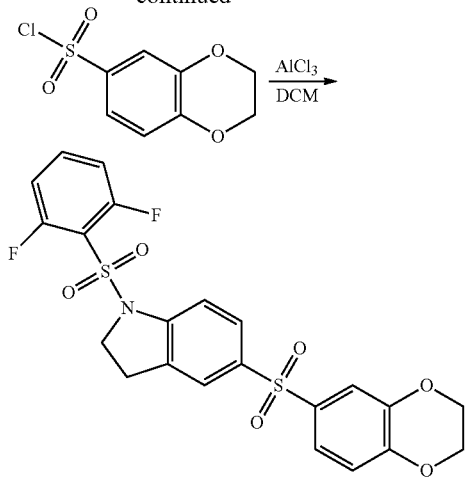

Mw = 493.50

Reagents Table—Step 1

| Reagent/raw material | MW (gr/mole) | Quantity/ mgr | Mmole | Mole ratio |
|---|---|---|---|---|
| Indoline | 119.2 | 0.19 ml | 1.7 | 1.0 |
| 2,6-Difluorobenzene-1-sulfonyl chloride | 212.6 | 510 | 2.4 | 1.4 |
| Pyridine | — | 10 ml | — | — |

Procedure:

Indoline was dissolved in dry pyridine. 2,6-Difluorobenzene-1-sulfonyl chloride was added dropwise and the reaction mixture was stirred overnight at rt. Intense red color appeared during the reaction. Monitoring by HPLC and LCMS indicated that the reaction was completed. The solvent was evaporated under reduced pressure, then HCl 1N solution and EtOAc were added. The organic layer was separated and the aqueous phase was extracted twice with EtOAc. The combined organic phase was dried over $Na_2SO_4$ and the solvent was evaporated under reduced pressure to yield the pure product as a yellow solid: 450 mg, 89% yield.

Reagents Table—Step 2

| Reagent/raw material | W (gr/mole) | Quantity/ mgr | Mmole | Mole ratio |
|---|---|---|---|---|
| 1-((2,6-difluorophenyl)sulfonyl)indoline | 295.3 | 450 | 1.5 | 1.0 |
| 2,3-Dihydrobenzo[b][1,4]dioxine-6-sulfonyl chloride | 234.6 | 422 | 1.8 | 1.2 |
| Aluminium chloride | 133.3 | 300 | 2.25 | 1.5 |
| DCM | — | 10 ml | — | — |

Procedure:

2,3-Dihydrobenzo[b][1,4]dioxine-6-sulfonyl chloride was stirred in DCM with aluminium chloride for 10 min, and then 1-((2,6-difluorophenyl)sulfonyl)indoline was added dropwise. The reaction was heated to 700 C in pressure ampoule overnight. The solvent was evaporated and redissolved in EtOAc and then washed twice with cold water and brine. The combined organic phase was dried over Na2SO4 and the solvent was evaporated under reduced pressure. The crude solid obtained (670 mg) was purified by combi flash column to give the pure product as a yellow solid: 272 mg, 100% purity, 37% yield. Analysis: HPLC–100% purity, 8.85 min. MS–(ES+) Calcd. for C22H17F2NO6S2 493.5. found 494.0 (MH+).

Example 29

Synthesis of 5-((2,3-dihydrobenzo[b][1,4]dioxin-6-yl)sulfonyl)-1-(o-tolylsulfonyl)indoline

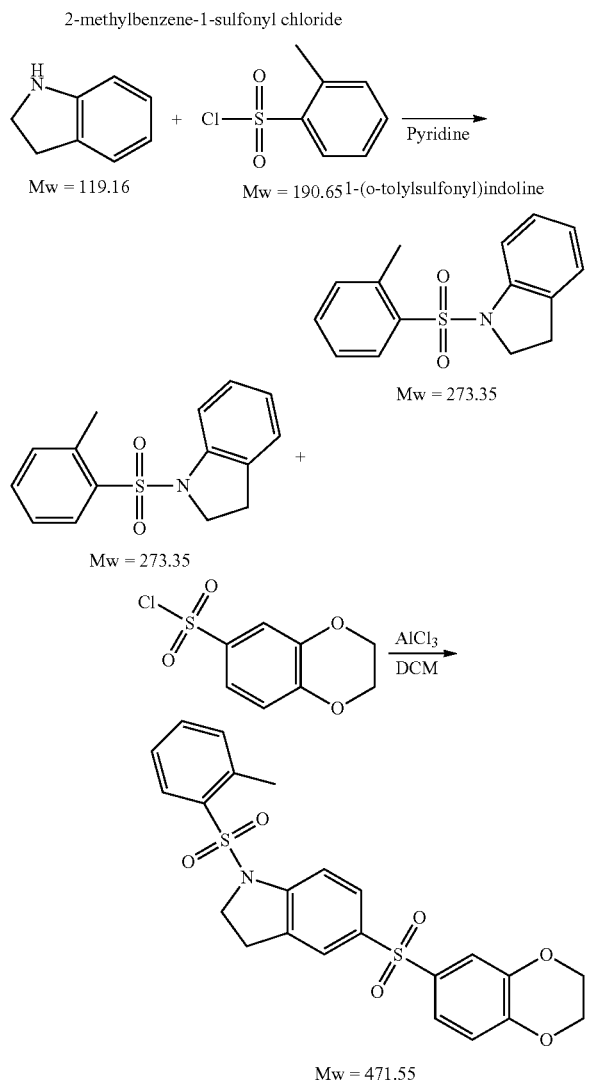

Reagents Table—Step 1

| Reagent/raw material | MW (gr/mole) | Quantity/ mgr | Mmole | Mole ratio |
|---|---|---|---|---|
| Indoline | 119.2 | 0.19 ml | 1.7 | 1.0 |
| 2-Methylbenzene-1-sulfonyl chloride | 190.65 | 458 | 2.4 | 1.4 |
| Pyridine | — | 10 ml | — | — |

Procedure:

Indoline was dissolved in dry pyridine. 2-Methylbenzene-1-sulfonyl chloride was added dropwise and the reaction mixture was stirred overnight at rt. Intense red color appeared during the reaction. Monitoring by HPLC and LCMS indicated that the reaction was completed. The solvent was evaporated under reduced pressure, then HCl 1N solution and EtOAc were added. The organic layer was separated and the aqueous phase was extracted twice with EtOAc The combined organic phase was dried over Na2SO4 and the solvent was evaporated under reduced pressure to yield the pure product: 464 mg, 100% yield.

Reagents Table—Step 2

| Reagent/raw material | MW (gr/mole) | Quantity/ mgr | Mmole | Mole ratio |
|---|---|---|---|---|
| 1-(o-tolylsulfonyl)indoline | 273.3 | 464 | 1.7 | 1.0 |
| 2,3-Dihydrobenzo[b][1,4]dioxine-6-sulfonyl chloride | 234.6 | 477 | 2.0 | 1.2 |
| Aluminium chloride | 133.3 | 332 | 2.5 | 1.5 |
| DCM | — | 10 ml | — | — |

Procedure:

2,3-Dihydrobenzo[b][1,4]dioxine-6-sulfonyl chloride was stirred in DCM with aluminium chloride for 10 min, and then 1-(o-tolylsulfonyl)indoline was added dropwise. The reaction was heated to 700 C in pressure ampoule overnight. The solvent was evaporated and redissolved in EtOAc and then washed twice with cold water and brine. The combined organic phase was dried over Na2SO4 and the solvent was evaporated under reduced pressure. The crude solid obtained (970 mg) was purified by combi flash column to give the pure product: 222 mg, 95% purity, 27% yield. Analysis: HPLC–95% purity, 9.02 min. MS–(ES+) Calcd. for C23H21NO6S2 471.55. found 472.2 (MH+).

Example 30

Synthesis of

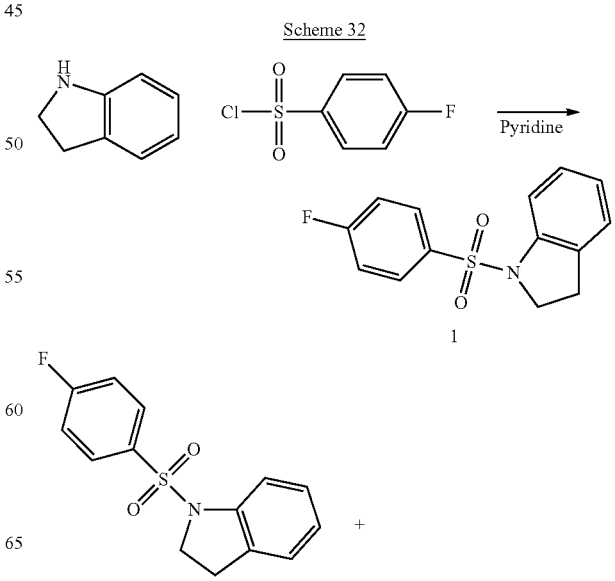

-continued

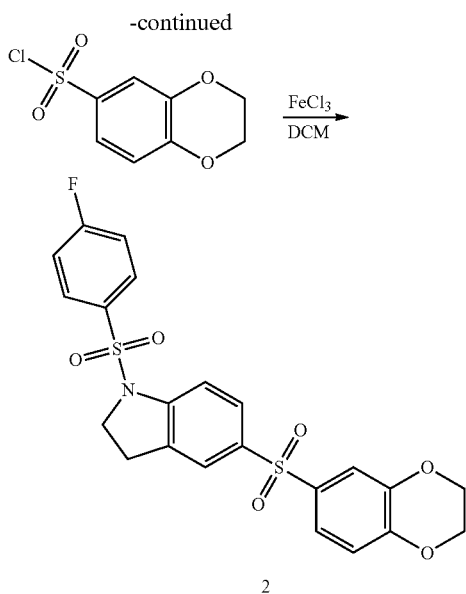

Reagents Table

| Reagent/raw material | MW (gr/mole) | Quantity | moles |
|---|---|---|---|
| Indoline | 119.16 | 0.5 g | 4.2 mmol |
| 4-fluorobenzene-1-sulfonyl chloride | 194.61 | 0.896 g | 4.6 mmol |
| 1-((4-fluorophenyl)sulfonyl)indoline | 277.31 | 0.5 g | 1.8 mmol |
| 2,3-dihydrobenzo[b][1,4]dioxine-6-sulfonyl chloride | 234.66 | 0.47 g | 2 mmol |
| FeCl3 | 126 | 0.69 | 5.5 mmol |

Procedure:

Synthesis of 1: Indoline was dissolved in 5 ml dry pyridine, and 4-fluorobenzene-1-sulfonyl chloride was added. Reaction stirred for overnight at RT, intense red color developed. When complete by HPLC and LCMS, solvent was evaporated, crude reaction mixture was dissolved in EA and washed with HCl 1N, water and brine. Organic phase was evaporated and purified by CombiFlash (PE/EtOAC) yield 1.35 g product 100% pure, (100% yield)

Synthesis of 2: 2,3-dihydrobenzo[b][1,4]dioxine-6-sulfonyl chloride was stirred in dichloromethane with FeCl3 for 20 min, and then 1-((4-fluorophenyl)sulfonyl)indoline was added in with stirring. Reaction mixture was stirred at RT for overnight. DCM was evaporated and redissolved in EtOAc and then washed with 2*50 ml cold water and brine. Organic phase dried over $Na_2SO_4$, evaporated and purified on CombiFlash. Product eluted at EtoAc/PE, 48 mg, 95% pure, 5.5% yield. Analysis: HPLC: rt-8.77 min 95%. MS–475.51 (calc.), 476.0 (MS+H$^+$)

Example 33

PKM2 Enzymatic Activity Assays

Assay Protocol

The ability of several test compounds to activate PKM2 was determined and the results are presented in Table 1 below.

PKM2 performs the following enzymatic reaction, where the PKM2 substrates, PEP (phosphoenolpyruvate) and ADP, are converted to pyruvate and ATP as follows:

PEP+ADP→Pyruvate+ATP.

All of the enzymatic reactions were conducted in duplicates at room temperature for 1 hour in a 50 μL mixture containing: PKM2 assay buffer (50 mM Immidazole, pH 7.2; 7 mM MgCl2; 50 mM KCl; 0.01% Tween; and 0.05% BSA), 0.1 mM ADP, 0.5 mM PEP, 0.1 nM PKM2 enzyme (PKM2, human recombinant (BPS catalog number 50295)) and the indicated test compound.

Fructose 1,6 biphosphate, (FBP (Sigma)) was used as a positive control for activation at concentration of 0.5 mM. After enzymatic reactions, 50 μL of Kinase-Glo® Plus reagent (Promega kit) was added to each well and luminescence was measured using a BioTek Synergy™ 2 microplate reader.

Data Analysis

PKM2 activity assays were performed in duplicates at each concentration. The luminescence data were analyzed using the computer software, GraphPad PRISM®. In the absence of the compound, the luminescence was defined as 0% activity. The percent activity in the presence of each compound was calculated according to the following equation:

% Activity=$[(L-L_b)/(L_t-L_b)-1]\times 100\%$ where L=the luminescence in the presence of the test compound, $L_b$=the luminescence in the absence of PKM2, and $L_t$=the luminescence intensity in the absence of the test compound. The % activity values versus a series of compound concentrations were plotted using non-linear regression analysis of Sigmoidal dose-response curve generated with the equation Y=B+(T−B)/1+10$^{((LogEC50-X)\times Hill\ Slope)}$, where Y=percent activity, B=minimum percent activity, T=maximum percent activity, X=logarithm of compound and Hill Slope=slope factor or Hill coefficient. The $EC_{50}$ value was determined for the indicated compounds as the concentration causing a half-maximal percent activity.

The data is presented whereby the letter "A" means the compound has an $EC_{50}$ between 0.0000001 μM≤1,000 nM, the letter "B" means the compound has an $EC_{50}$ between 1,000 nM≤10,000 nM, the letter "C" means the compound has an $EC_{50}$ between 10,000 nM≤100,000 nM. The letter "D" means the compound $EC_{50}$ was not determined.

It will be recognized by one skilled in the art that the presentation of data is illustrative and in no way intended to limit the scope of the present invention. Furthermore, the letters "A", "B", and "C" are also illustrative and in no way is intended to limit the scope of the present invention. For example, the symbol "C" is not meant to indicate that a compound necessarily lacks activity or utility but rather that its $EC_{50}$ value is between 10,000 nM≤100,000 nM.

TABLE 3

| Compound No. | EC50 |
|---|---|
| 2A | B |
| 3A | A |
| 4A | B |
| 5A | A |
| 22A | A |
| 23A | C |
| 6A | A |
| 7A | B |
| 9A | A |
| 24A | C |
| 10A | B |

TABLE 3-continued

| Compound No. | EC50 |
| --- | --- |
| 11A | A |
| 12A | B |
| 13A | B |
| 14A | A |
| 15A | A |
| 16A | A |
| 18A | A |
| 19A | A |
| 21A | B |
| 26A | D |
| 27A | D |
| 28A | D |
| 29A | D |
| 30A | D |
| 31A | A |
| 32A | A |
| 33A | A |

Example 34

In Vitro Cell Proliferation Assays

Assay Protocol I

Growth inhibitory activity against the human tumor cell lines of compounds of the invention was determined using Promega's CellTiterGlo® assay. The cell lines of interest were placed in a 96-well microculture plate (Costar® white, flat bottom #3917) in a total volume of 90 μL/well. After 24 hours of incubation in a humidified incubator at 37° C. with 5% $CO_2$ and 95% air, 10 μL of serially diluted test compounds in growth medium were added to each well. After 96 total hours of culture in a $CO_2$ incubator, the plated cells and CellTiter-Glo® (Promega # G7571) reagents were brought to room temperature to equilibrate for 30 minutes. 100 μL of CellTiter-Glo® reagent was added to each well. The plate was shaken for 2 minutes and then left to equilibrate for 10 minutes before reading luminescence on the Tecan GENios microplate reader.

Percent inhibition of cell growth was calculated relative to untreated control wells. All tests were performed in triplicate for each concentration level. The $IC_{50}$ value for the test compounds was estimated using Prism 3.03 by curve-fitting the data.

Assay Protocol II

In a second assay to determine the inhibition of cell proliferation by a compound of the invention, cell proliferation of the cell line of interest was measured by a cell proliferation index assay using Fluofarma® based technology. This assay is based on the dilution rate of a fluorescent membrane marker, which is a direct function of the number of cell divisions. Briefly, the assay is performed by loading the cells with a non-toxic fluorescent phospholipid analog before the seeding. The probe inserts stably into the cell membrane, after which the probe does not exchange with neighboring cells or the surrounding medium; however, the probe will be distributed between daughter cells after division. Flow cytometry analysis of the fluorescent probe is performed after the loading of the cells both prior to, as well as after treatment with various concentrations of the test compound. The dilution rate of the fluorescent probe at the single cell level is directly correlated to the number of cell divisions.

Results

The results for the indicated tumor cells lines of inhibition of cellular proliferation by the indicated compounds of the invention are provided below (all results are as measured using Assay Protocol I, except as otherwise noted):

5-((2,3-dihydrobenzo[b][1,4]dioxin-6-yl)sulfonyl)-2-methyl-1-(methylsulfonyl)indoline

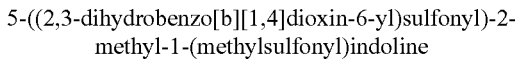

Compound 2A

| Cell line | $IC_{50}$ Compound 2A |
| --- | --- |
| H1299 (Non small cell lung carcinoma cell line) | <10 μM/<40 μM[†] |
| A549 (Non-small cell lung carcinoma cell line) | <50 μM |
| HT-29 (Colorectal cancer cell line) | >100 μM |
| Colo-205 (Colorectal cancer cell line) | <30 μM |
| HeLa (Cervical cancer cell line) | <60 μM |
| 786-O (Renal cancer cell line) | <30 μM |

[†]As measured by Assay Protocol II.

Figure 2:
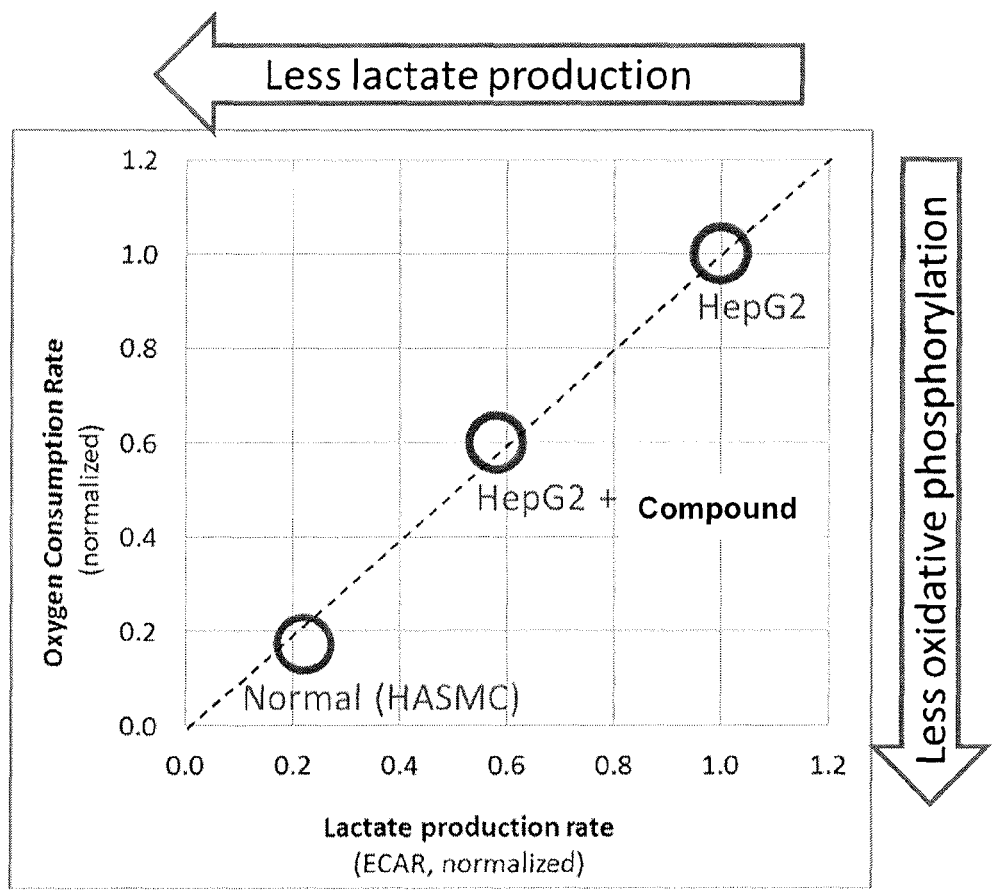
FIG. 2 shows that HepG2 cancer cells (hepatocellular carcinoma cells) treated with the test compound 5-((2,3-dihydrobenzo[b][1,4]dioxin-6-yl)sulfonyl)-2-methyl-1-(methylsulfonyl)indoline become less metabolically active—in the direction of normal cellular metabolism (human aortic smooth muscle cells (HASMC).

Bioenergetic studies were performed using XF24 analyzer (Seahorse Bioscience). Oxygen Consumption Rate (OCR), a measure of mitochondrial oxydative phosphorylation, and Extra-Cellular Acidification Rate (ECAR), which represents glycolysis, were recorded over an 8 hour period for cells treated with various test compounds at 100 μM. The results for 5-((2,3-dihydrobenzo[b][1,4]dioxin-6-yl)sulfonyl)-2-methyl-1-(methylsulfonyl)indoline are shown in FIG. 2. As shown in FIG. 2, HepG2 cancer cells (hepatocellular carcinoma cells) treated with 5-((2,3-dihydrobenzo[b][1,4]dioxin-6-yl)sulfonyl)-2-methyl-1-(methylsulfonyl)indoline become less metabolically active—in the direction of normal cellular metabolism (human aortic smooth muscle cells (HASMC).

Figure 3:
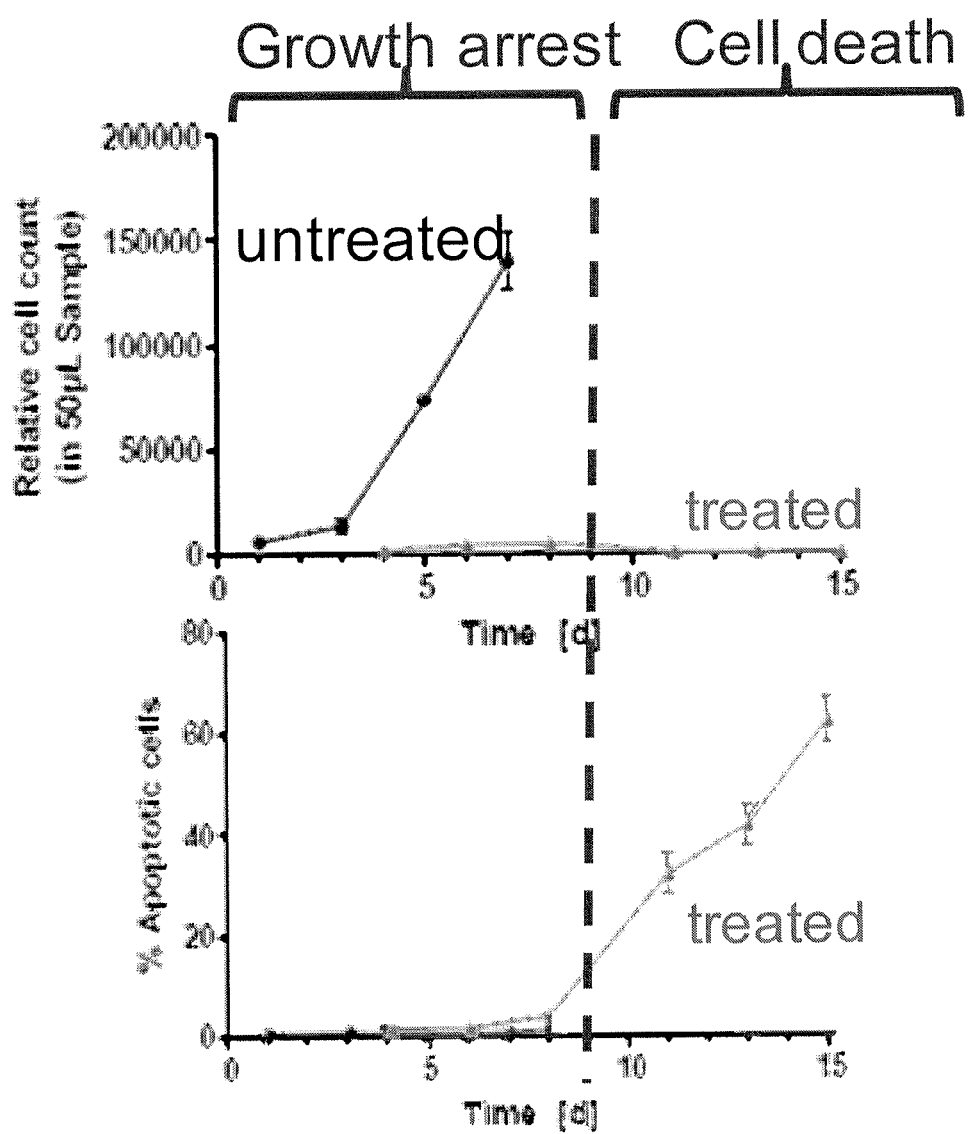
FIG. 3 shows plots of cell counts (top panel) or percent of cells that have undergone apoptosis (bottom panel) as a function of time after treatment with the compound 5-((2,3-dihydrobenzo[b][1,4]dioxin-6-yl)sulfonyl)-2-methyl-1-(methylsulfonyl)indoline.

Additionally, the effect of 5-((2,3-dihydrobenzo[b][1,4]dioxin-6-yl)sulfonyl)-2-methyl-1-(methylsulfonyl)indoline on cell proliferation and apoptosis was measured and the results are shown in FIG. 3. As shown in FIG. 3, treatment with the compound induces a period of growth arrest, i.e., a cytostatic effect, which is later followed by apoptosis. The apoptosis analysis (caspase 3/7 assay) indicates that by day 15, up to 60% of cells underwent apoptosis.

5-((2,3-dihydrobenzo[b][1,4]dioxin-6-yl)sulfonyl)-2-(methylsulfonyl)isoindoline

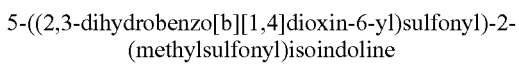

Compound 6A

| Cell line | $IC_{50}$ Compound 6A |
| --- | --- |
| H1299 (Non-small cell lung carcinoma cell line) | <20 μM[†] |

[†]As measured by Assay Protocol II.

5-((2,3-dihydrobenzo[b][1,4]dioxin-6-yl)sulfonyl)-1-(methylsulfonyl)indoline

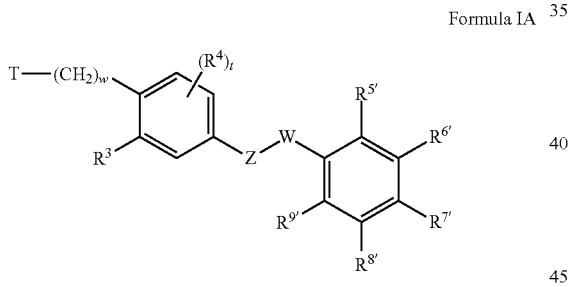

Compound 11A

| Cell line | IC$_{50}$ Compound 11A |
|---|---|
| H1299 (Non-small cell lung carcinoma cell line) | <20 μM |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

What is claimed is:

1. A compound of Formula IA:

$$T-(CH_2)_w \text{—Ar}(R^4)_t \text{—} Z \text{—} W \text{—Ar}(R^{5'}, R^{6'}, R^{7'}, R^{8'}, R^{9'})$$

Formula IA or a salt, solvate, hydrate, or prodrug thereof, wherein:
Z is $SO_2$;
W is absent;
T is selected from the group consisting of $NR^2COR^1$ and $NR^2S(O)_2R^1$;
$R^1$ is selected from the group consisting of a linear or branched $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ cycloalkenyl, heterocycloalkyl, aryl and heteroaryl,
wherein said alkyl, alkenyl, alkynyl, cycloalkyl, cycloalkenyl, heterocycloalkyl, aryl and heteroaryl are unsubstituted or substituted with one or more $R^c$,
$R^c$ is independently at each occurrence selected from the group consisting of linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, aryloxy, linear or branched $C_1$-$C_6$ haloalkoxy, linear or branched $C_1$-$C_6$ alkylsulfonyl, linear or branched $C_1$-$C_6$ thioalkyl, thioaryl, $C_3$-$C_8$ cycloalkyl, $C_3$-$C_8$ cycloalkenyl, aryl, heteroaryl, heterocycloalkyl, hydroxyl, cyano, nitro, halogen, $COR^d$, $COOR^d$, $CONR^dR^e$, $NHCOR^d$, and $NR^dR^e$;
$R^d$ and $R^e$ are, each independently selected from the group consisting of linear or branched, $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ cycloalkenyl, heterocycloalkyl, aryl, and heteroaryl;
$R^2$ and $R^3$, together with the atoms to which they are attached, form a five to seven membered heterocycloalkyl or heteroaryl ring containing one nitrogen atom, wherein said ring is unsubstituted or substituted with one or more $R^m$,
$R^m$ is selected from the group consisting of halogen, linear or branched $C_1$-$C_6$ alkyl, linear or branched $C_2$-$C_6$ alkenyl, linear or branched $C_2$-$C_6$ alkynyl, linear or branched $C_1$-$C_6$ alkoxy, linear or branched $C_1$-$C_6$ haloalkyl, benzyloxy, $NR^dR^e$, $NHCOR^d$, and $SO_2R^d$;
$R^4$ is selected from the group consisting of halogen, linear or branched $C_1$-$C_6$ alkyl, linear or branched $C_2$-$C_6$ alkenyl, linear or branched $C_2$-$C_6$ alkynyl, and heteroalkyl, wherein said alkyl, alkenyl, alkynyl, and heteroalkyl are unsubstituted or substituted with one or more $R^f$,
$R^f$ is independently at each occurrence selected from the group consisting of linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, aryloxy, linear or branched $C_1$-$C_6$ haloalkoxy, linear or branched $C_1$-$C_6$ alkylsulfonyl, linear or branched, $C_1$-$C_6$ thioalkyl, thioaryl, $C_3$-$C_8$ cycloalkyl, $C_3$-$C_8$ alkenyl, aryl, heteroaryl, heterocycloalkyl, hydroxyl, cyano, amino, nitro, halogen, $COR^g$, $COOR^g$, $CONR^gR^h$, $NHCOR^g$, and $NR^gR^h$;
$R^g$ and $R^h$ are, each independently selected from a group consisting of hydrogen, linear or branched $C_1$-$C_6$ alkyl, linear or branched $C_2$-$C_6$ alkenyl, linear or branched $C_2$-$C_6$ alkynyl, $C_3$-$C_8$ cycloalkyl, $C_3$-$C_8$ cycloalkenyl, heterocycloalkyl, aryl and heteroaryl;
t is 0, 1, 2 or 3;
$R^{5'}$, $R^{8'}$ and $R^{9'}$ are, each independently, selected from hydrogen, linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, linear or branched $C_1$-$C_6$ alkoxy, benzyloxy, aryloxy, linear or branched $C_1$-$C_6$ haloalkoxy, linear or branched $C_1$-$C_6$ alkylsulfonyl, linear or branched $C_1$-$C_6$ thioalkyl or thioaryl, $C_3$-$C_8$ cycloalkyl, $C_3$-$C_8$ cycloalkenyl, aryl, heteroaryl, heterocycloalkyl, hydroxyl, cyano, amino, nitro, halogen, $COR^i$, $COOR^i$, $CONR^iR^j$, $NHCOR^i$, and $NR^iR^j$;
$R^i$ and $R^j$ are, each independently, hydrogen or a group selected from a linear or branched $C_1$-$C_6$ alkyl, linear or branched $C_2$-$C_6$ alkenyl, linear or branched $C_2$-$C_6$ alkynyl, linear or branched $C_1$-$C_6$ haloalkyl, $C_3$-$C_8$ cycloalkyl, $C_3$-$C_8$ cycloalkenyl, or heterocycloalkyl, aryl and heteroaryl, wherein said alkyl, alkenyl, alkynyl, cycloalkyl, cycloalkenyl, heterocycloalkyl, aryl, and heteroaryl are unsubstituted or substituted with one or more $R^k$,
$R^k$ is selected from halogen or hydroxyl;
$R^{6'}$ and $R^{7'}$ together with the atoms to which they are attached, form a 6 membered heterocycloalkyl ring consisting of four carbon atoms and two oxygen atoms, wherein said heterocycloalkyl ring is unsubstituted or substituted with one or more $R^{m1}$ selected from $C_1$-$C_6$alkyl and $S(O)_p(C_1$-$C_6$ alkyl);

w is 0 or 1, and p is 0, 1, or 2.

2. The compound according to claim 1 of Formula IIA:

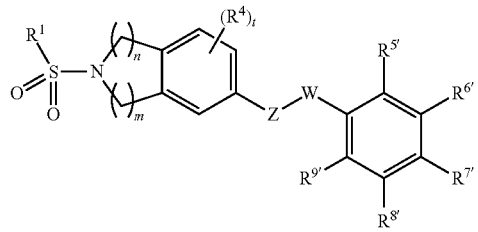

(IIA)

or a salt, solvate, hydrate or prodrug thereof, wherein:
m is 0, 1, 2, 3, or 4;
n is 0, 1, 2, 3 or 4, thereby forming a five to seven membered heteroaryl or a five to seven membered heterocycloalkyl ring, wherein the five to seven membered heteroaryl or heterocycloalkyl ring is unsubstituted or substituted with one or more $R^m$,
$R^m$ is linear or branched $C_1$-$C_6$ alkyl.

3. The compound according to claim 1 of Formula IIB:

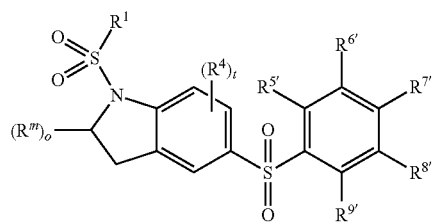

(IIB)

or a salt, solvate, hydrate, or prodrug thereof and wherein o is 0 or 1.

4. The compound according to claim 1 of Formula IID:

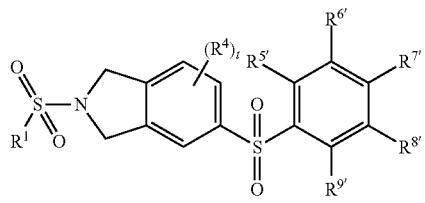

(IID)

or a salt, solvate, hydrate, or prodrug thereof.

5. The compound according to claim 1 or a salt, solvate, hydrate, or prodrug thereof, wherein $R^{6'}$ and $R^{7'}$ together with the atoms to which they are attached form a 1,4-dioxane ring.

6. The compound according to claim 5 or a salt, solvate, hydrate, or prodrug thereof, wherein remaining $R^{8'}$ $R^{5'}$ and $R^{9'}$ are each hydrogen.

7. The compound according to claim 1 or a salt, solvate, hydrate, or prodrug thereof, wherein $R^1$ is selected from $C_1$-$C_6$ alkyl, $C_2$-$C_6$ alkenyl, $C_2$-$C_6$ alkynyl, $C_1$-$C_6$ haloalkyl, aryl, heteroaryl, $C_3$-$C_8$ cycloalkyl, and $C_3$-$C_8$ cycloalkenyl.

8. The compound according to claim 7 or a salt, solvate, hydrate, or prodrug thereof, wherein $R^1$ is selected from $C_1$-$C_6$ alkyl and aryl, wherein said aryl is unsubstituted or substituted with one or more $R^c$.

9. The compound according to claim 1 or a salt, solvate, hydrate, or prodrug thereof, wherein t is 0.

10. A compound selected from

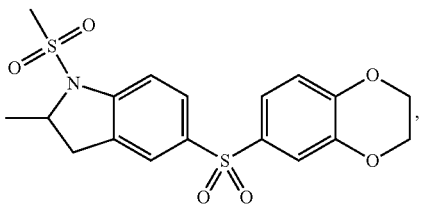

(2A)

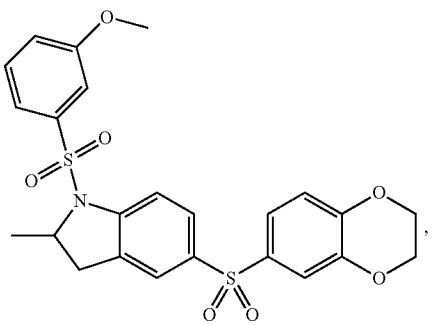

(3A)

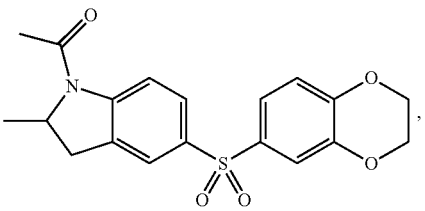

(4A)

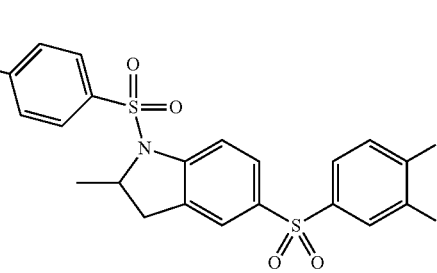

(5A)

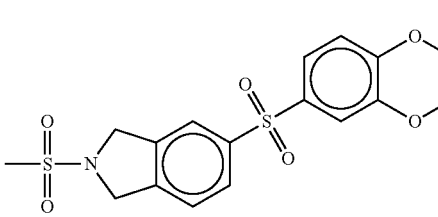

(6A)

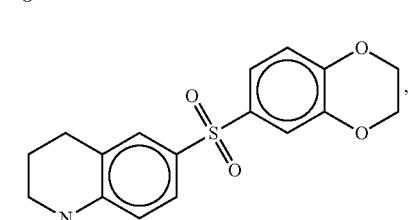

(7A)

(9A)
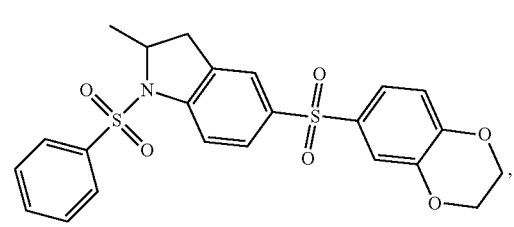
(11A)
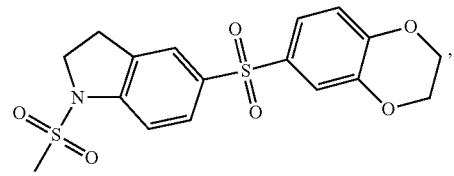
(13A)
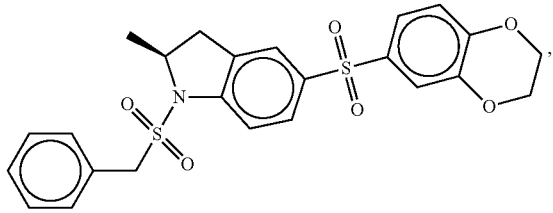
(14A)
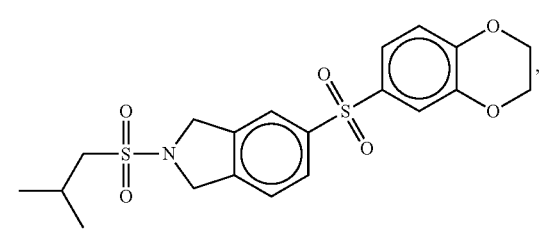
(15A)
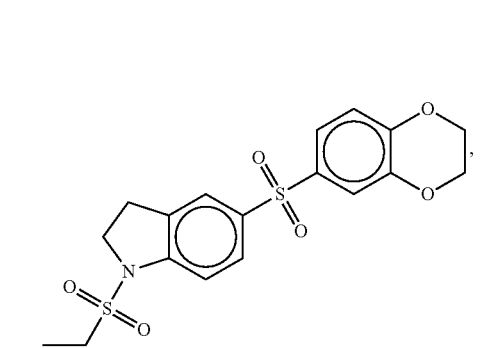
(16A)
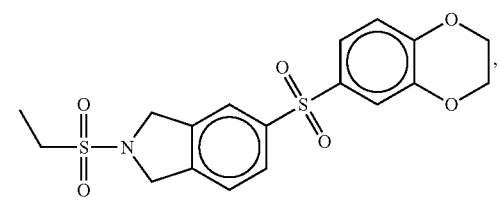
(17A)
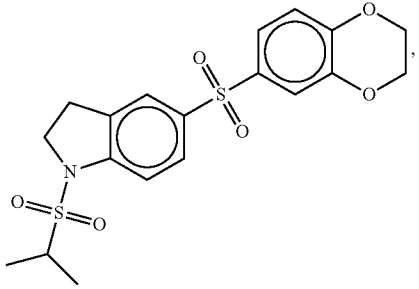
(18A)
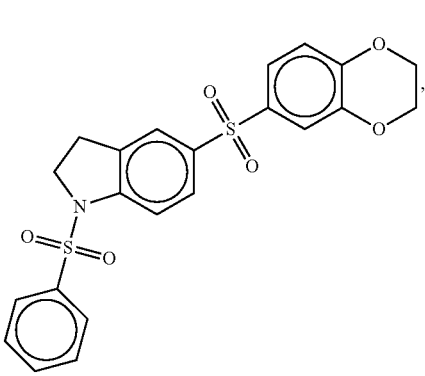
(19A)
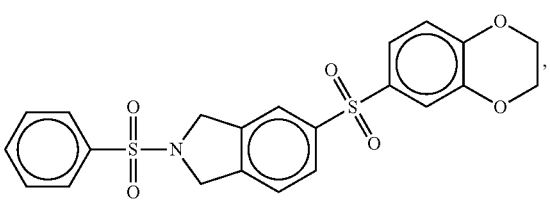
(21A)
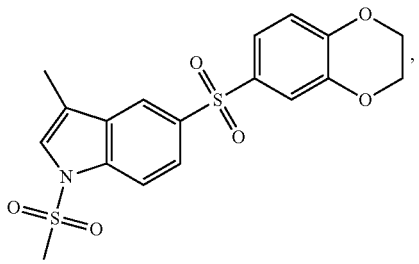
(22A)
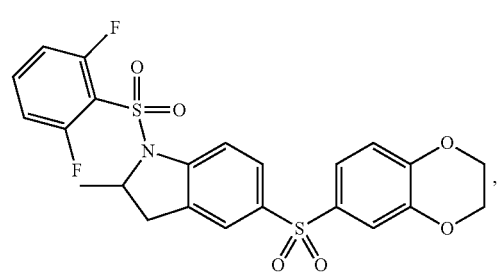

-continued
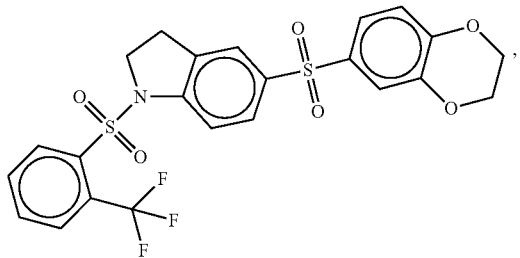
(29A)
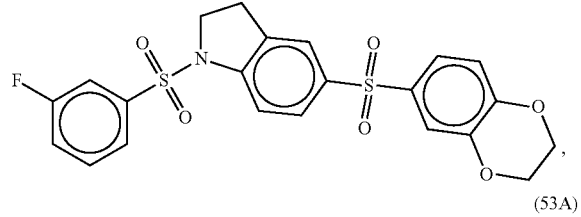
(33A)
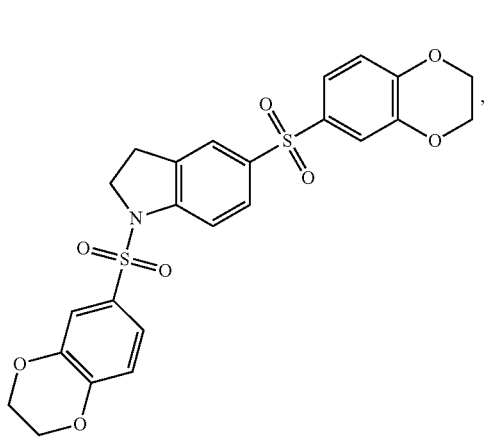
(30A)
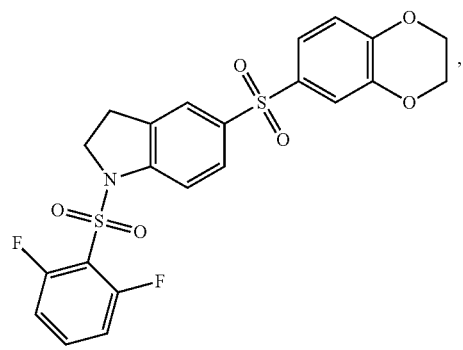
(53A)
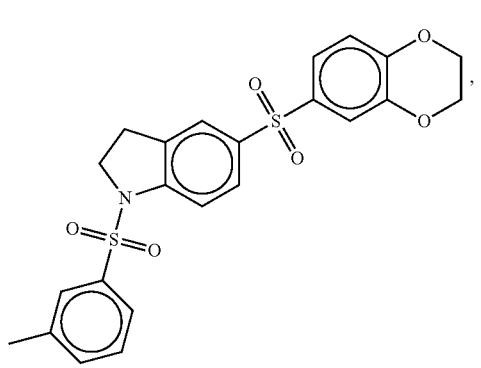
(31A)
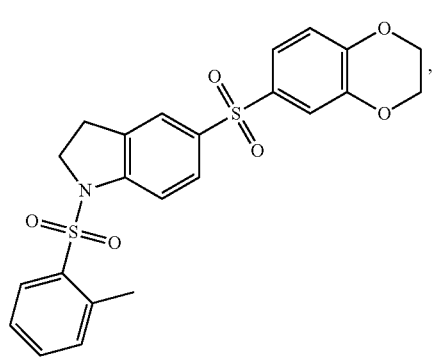
(54A)
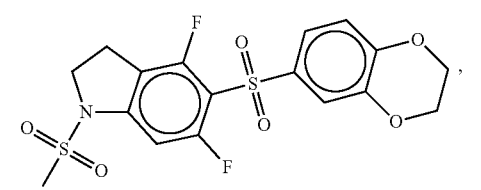
(31A)
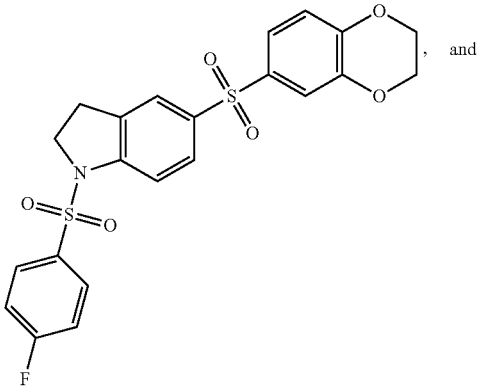
(55A) and
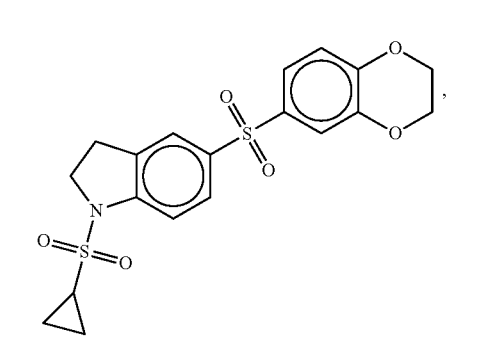
(32A)
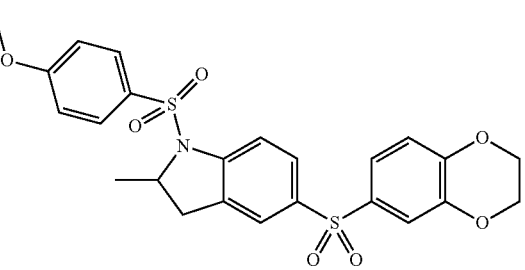
(56A)
or a salt, solvate, hydrate, or prodrug thereof.

11. A pharmaceutical composition comprising a compound according to claim 1 or a salt, solvate, hydrate, or prodrug thereof and at least one pharmaceutically acceptable carrier or excipient.

12. The compound of claim 3, wherein o is 0.

13. The compound of claim 3, wherein o is 1 and $R^m$ is $CH_3$.

14. The compound of claim 3, wherein t is 0.

15. The compound of claim 3, wherein $R^1$ is selected from $C_1$-$C_6$ alkyl, $C_1$-$C_6$ haloalkyl, aryl, heteroaryl, and $C_3$-$C_8$ cycloalkyl.

16. The compound of claim 15, wherein $R^1$ is selected from methyl, ethyl, propyl, isopropyl, butyl, and isobutyl.

17. The compound of claim 15, wherein $R^1$ is aryl, wherein said aryl is unsubstituted or substituted with one or more $R^c$ selected from methyl, $OCH_3$, F, Cl, and $CF_3$.

18. The compound of claim 3, wherein $R^{6'}$ and $R^{7'}$ together with the atoms to which they are attached form a 1,4-dioxane ring.

19. The compound of claim 18, wherein $R^{5'}$, $R^{8'}$, and $R^{9'}$ are each hydrogen.

20. The compound of claim 2, wherein $R^{6'}$ and $R^{7'}$ together with the atoms to which they are attached form a 1,4-dioxane ring.

* * * * *